(12) United States Patent
Schneider et al.

(10) Patent No.: US 10,667,806 B2
(45) Date of Patent: *Jun. 2, 2020

(54) APPLICATOR INSTRUMENTS WITH RECONFIGURABLE HANDLES FOR DISPENSING SURGICAL FASTENERS

(71) Applicant: Ethicon, Inc., Somerville, NJ (US)

(72) Inventors: Jared Schneider, Union, NJ (US); Jianxin Guo, Livingston, NJ (US); Michael Cardinale, Morristown, NJ (US); Simon Cohn, Lebanon, NJ (US); Mark D. Kenyon, Ringoes, NJ (US); Doug Souls, Andover, NJ (US); Danial Paul Ferreira, Woodbridge, CT (US); Xuelin Guo, Livingston, NJ (US); Lindsay Epstein, Belle Mead, NJ (US)

(73) Assignee: Ethicon, Inc., Somerville, NJ (US)

( * ) Notice: Subject to any disclaimer, the term of this patent is extended or adjusted under 35 U.S.C. 154(b) by 360 days.

This patent is subject to a terminal disclaimer.

(21) Appl. No.: 15/493,875

(22) Filed: Apr. 21, 2017

(65) Prior Publication Data

US 2018/0153543 A1 Jun. 7, 2018

Related U.S. Application Data

(60) Provisional application No. 62/431,355, filed on Dec. 7, 2016.

(51) Int. Cl.
*A61B 17/068* (2006.01)
*A61B 17/064* (2006.01)
(Continued)

(52) U.S. Cl.
CPC ...... *A61B 17/064* (2013.01); *A61B 17/00234* (2013.01); *A61B 17/0682* (2013.01);
(Continued)

(58) Field of Classification Search
CPC .................................................. A61B 17/064
(Continued)

(56) References Cited

U.S. PATENT DOCUMENTS 3,740,994 A 6/1973 DeCarlo
4,127,227 A 11/1978 Green
(Continued)

FOREIGN PATENT DOCUMENTS

EP 0598529 5/1994
EP 2090254 8/2009
(Continued)

OTHER PUBLICATIONS

International Search Report issued in the corresponding International Application No. PCT/US2017/061264, dated Apr. 20, 2018, 4 pages.

(Continued)

*Primary Examiner* — Chelsea E Stinson

(57) ABSTRACT

An applicator instrument having a reconfigurable handle for dispensing surgical fasteners includes a housing having a proximal end and a distal end, an elongated shaft extending from the housing, a handle coupled with the proximal end of the housing, and a trigger coupled with the handle. The applicator instrument has a firing system including an energy storing assembly that is disposed within the housing, and a gear train disposed within the handle and coupled with the trigger. The trigger is squeezed for commencing a firing cycle and storing energy in the energy storing assembly. The applicator instrument includes a handle reconfiguration actuator having a first position for locking the handle in place relative to the housing and a second position for enabling the handle to rotate relative to the housing between a pistol configuration and an in-line configuration. The applicator instrument dispenses surgical fasteners with the (Continued)

handle in the pistol configuration, the in-line configuration, and at angles located between the pistol and in-line configurations.

19 Claims, 56 Drawing Sheets

(51) Int. Cl.
| | |
|---|---|
| A61B 34/37 | (2016.01) |
| A61B 17/00 | (2006.01) |
| A61B 17/072 | (2006.01) |
| A61F 2/02 | (2006.01) |
| A61B 34/30 | (2016.01) |
| A61B 90/92 | (2016.01) |
| A61B 17/29 | (2006.01) |
| A61B 90/00 | (2016.01) |

(52) U.S. Cl.
CPC ........ *A61B 17/07207* (2013.01); *A61B 34/37* (2016.02); *A61F 2/02* (2013.01); *A61B 90/92* (2016.02); *A61B 2017/003* (2013.01); *A61B 2017/0053* (2013.01); *A61B 2017/00314* (2013.01); *A61B 2017/00327* (2013.01); *A61B 2017/00407* (2013.01); *A61B 2017/0688* (2013.01); *A61B 2017/291* (2013.01); *A61B 2017/2923* (2013.01); *A61B 2017/2925* (2013.01); *A61B 2017/2927* (2013.01); *A61B 2034/306* (2016.02); *A61B 2090/0808* (2016.02)

(58) Field of Classification Search
USPC ........................................... 227/175.2, 176.1
See application file for complete search history.

(56) References Cited

U.S. PATENT DOCUMENTS

| | | | |
|---|---|---|---|
| 4,152,920 A | 5/1979 | Green | |
| 4,325,376 A | 4/1982 | Klieman et al. | |
| 4,471,780 A | 9/1984 | Menges et al. | |
| 4,478,220 A | 10/1984 | DiGiovanni et al. | |
| 4,951,860 A | 8/1990 | Peters et al. | |
| 5,174,487 A | 12/1992 | Rothfuss et al. | |
| 5,190,560 A | 3/1993 | Woods | |
| 5,203,864 A | 4/1993 | Phillips | |
| 5,290,297 A | 3/1994 | Phillips | |
| 5,443,197 A | 8/1995 | Malis et al. | |
| 5,465,895 A * | 11/1995 | Knodel ............ | A61B 17/07207 227/176.1 |
| 5,470,010 A | 11/1995 | Rothfuss et al. | |
| 5,582,616 A | 12/1996 | Bolduc et al. | |
| 5,601,573 A | 2/1997 | Fogelberg et al. | |
| 5,680,981 A | 10/1997 | Mililli et al. | |
| 5,704,534 A | 1/1998 | Huitema et al. | |
| 5,810,882 A | 9/1998 | Bolduc et al. | |
| 5,830,221 A | 11/1998 | Stein et al. | |
| 5,833,700 A | 11/1998 | Fogelberg et al. | |
| 5,878,193 A | 3/1999 | Wang et al. | |
| 5,921,997 A | 7/1999 | Fogelberg et al. | |
| 6,132,368 A | 10/2000 | Cooper | |
| 6,319,258 B1 | 11/2001 | McAllen et al. | |
| 6,457,625 B1 * | 10/2002 | Tormala ............... | A61B 17/064 227/177.1 |
| 6,551,333 B2 | 4/2003 | Kuhns et al. | |
| 6,626,916 B1 | 9/2003 | Yeung et al. | |
| 6,702,737 B2 | 3/2004 | Hino et al. | |
| 7,485,124 B2 | 2/2009 | Kuhns et al. | |
| 7,524,320 B2 | 4/2009 | Tierney et al. | |
| 7,533,790 B1 | 5/2009 | Knodel et al. | |
| 7,758,612 B2 | 7/2010 | Shipp | |
| 8,091,755 B2 | 1/2012 | Kayan et al. | |
| 8,241,320 B2 | 8/2012 | Lyons et al. | |
| 8,418,908 B1 | 4/2013 | Beardsley | |
| 8,474,679 B2 | 7/2013 | Felix | |
| 8,579,920 B2 | 11/2013 | Nering et al. | |
| 8,690,889 B2 | 4/2014 | Colesanti et al. | |
| 8,728,098 B2 | 5/2014 | Daniel et al. | |
| 8,728,099 B2 | 5/2014 | Cohn et al. | |
| 8,789,739 B2 | 7/2014 | Swensgard | |
| 8,894,669 B2 | 11/2014 | Nering et al. | |
| 8,920,439 B2 | 12/2014 | Cardinale et al. | |
| 8,986,287 B2 * | 3/2015 | Park ................... | A61B 17/2909 606/1 |
| 9,038,880 B1 | 5/2015 | Donohoe | |
| 9,055,945 B2 | 6/2015 | Miksza et al. | |
| 9,119,629 B2 | 9/2015 | Cardinale et al. | |
| 9,144,369 B2 | 9/2015 | Ostrovsky et al. | |
| D744,646 S | 12/2015 | Nering et al. | |
| 9,198,561 B2 | 12/2015 | Smith et al. | |
| 9,204,783 B2 | 12/2015 | Kappel et al. | |
| 9,211,134 B2 | 12/2015 | Stroup et al. | |
| 9,289,225 B2 | 3/2016 | Shelton, IV et al. | |
| 9,351,751 B2 | 5/2016 | Malkowski | |
| 2002/0068947 A1 | 6/2002 | Kuhns et al. | |
| 2002/0128669 A1 | 9/2002 | Field et al. | |
| 2003/0009195 A1 | 1/2003 | Field et al. | |
| 2005/0149064 A1 | 7/2005 | Peterson et al. | |
| 2006/0074028 A1 | 4/2006 | He et al. | |
| 2007/0021737 A1 | 1/2007 | Lee | |
| 2007/0088390 A1 | 4/2007 | Paz et al. | |
| 2007/0287993 A1 | 12/2007 | Hinman et al. | |
| 2008/0281332 A1 | 11/2008 | Taylor | |
| 2009/0088792 A1 | 4/2009 | Hoell, Jr. et al. | |
| 2010/0001036 A1 | 1/2010 | Marczyk et al. | |
| 2010/0191282 A1 | 7/2010 | Harris et al. | |
| 2010/0292712 A1 | 11/2010 | Nering et al. | |
| 2011/0079627 A1 | 4/2011 | Cardinale et al. | |
| 2011/0082472 A1 | 4/2011 | Harris et al. | |
| 2011/0208169 A1 | 8/2011 | Nash | |
| 2012/0080495 A1 | 4/2012 | Holcomb et al. | |
| 2012/0109186 A1 | 5/2012 | Parrott | |
| 2012/0209254 A1 * | 8/2012 | Park ................... | A61B 17/2909 606/1 |
| 2013/0023868 A1 | 1/2013 | Worrell et al. | |
| 2013/0021817 A1 | 8/2013 | Miksza et al. | |
| 2013/0218177 A1 | 8/2013 | Miksza et al. | |
| 2013/0301091 A1 | 11/2013 | Martinez | |
| 2013/0304091 A1 | 11/2013 | Straehnz et al. | |
| 2014/0005662 A1 | 1/2014 | Shelton | |
| 2014/0276965 A1 | 9/2014 | Ranucci et al. | |
| 2014/0379001 A1 | 12/2014 | Cohn et al. | |
| 2015/0001272 A1 | 1/2015 | Sniffin et al. | |
| 2015/0080919 A1 | 3/2015 | Nering et al. | |
| 2015/0265262 A1 | 9/2015 | Dewaele et al. | |
| 2016/0262738 A1 | 9/2016 | Altman | |
| 2016/0287256 A1 | 10/2016 | Marczyk | |
| 2018/0153547 A1 * | 6/2018 | Cohn ................. | A61B 17/0682 |
| 2018/0153550 A1 * | 6/2018 | Souls ................ | A61B 17/0682 |

FOREIGN PATENT DOCUMENTS

| | | |
|---|---|---|
| EP | 2606838 | 6/2013 |
| WO | 2009058671 | 5/2009 |
| WO | 2012040593 | 3/2012 |
| WO | 2013151858 | 10/2013 |
| WO | 2016061291 | 4/2016 |

OTHER PUBLICATIONS

Written Opinion of the International Searching Authority issued in the corresponding International Application No. PCT/US2017/061264, dated Apr. 20, 2018, 6 pages.

* cited by examiner

APPLICATOR INSTRUMENTS WITH RECONFIGURABLE HANDLES FOR DISPENSING SURGICAL FASTENERS

CROSS-REFERENCE TO RELATED APPLICATIONS

The present patent application claims benefit of U.S. Provisional Application Ser. No. 62/431,355, filed Dec. 7, 2016, and is related to U.S. patent application Ser. No. 15/372,241, filed Dec. 7, 2016, entitled "SURGICAL FASTENERS FOR MESH AND TISSUE FIXATION", the disclosures of which are hereby incorporated by reference herein. The present patent application is also related to U.S. patent application Ser. No. 15/493,898, filed Apr. 21, 2017, U.S. patent application Ser. No. 15/493,929, filed Apr. 21, 2017, U.S. patent application Ser. No. 15/493,957, filed Apr. 21, 2017, U.S. patent application Ser. No. 15/493,981, filed Apr. 21, 2017, and U.S. patent application Ser. No. 15/494,012, filed Apr. 21, 2017, all commonly assigned to Ethicon, Inc., the disclosures of which are hereby incorporated by reference herein.

BACKGROUND OF THE INVENTION

Field of the Invention

The present patent application is generally related to medical devices, and is more specifically related to medical devices that dispense surgical fasteners for securing prosthetic devices to tissue.

Description of the Related Art

A hernia is a condition where a small loop of bowel or intestine protrudes through a weak place or defect within the abdominal muscle wall or groin of a patient. This condition commonly occurs in humans, particularly males. Hernias of this type may result from a congenital defect whereby the patient is born predisposed with this condition, prior abdominal surgery, or may be caused by straining or lifting heavy objects. Heavy lifting may be known to create a large amount of stress upon the abdominal wall and can cause a rupture or tearing at a weak point of the abdominal muscle to create the defect or opening. In any case, the patient may be left with an unsightly bulge of intestinal tissue protruding through the defect, which may result in pain, reduced lifting abilities, and in some cases, impaction of the bowel, or possibly other complications if the flow of blood is cut off to the protruding tissue.

A common solution to the above-described problem may be surgery. During a surgical procedure, the defect is accessed and carefully examined, either through an open incision or endoscopically through an access port such as a trocar. In either case, careful examination is required due to the network of vessels and nerves which exist in the area of a typical defect, which requires a surgeon to conduct a hernia repair with great skill and caution. Within this area can be found vascular structures such as gastric vessels, the external iliac vessels, and the inferior epigastric vessels, as well as reproductive vessels such as the vas deferens extending through the inguinal floor.

Once the surgeon is familiar with the anatomy of a patient, the surgeon carefully places the viscera back into the patient's abdomen through the defect. Repairing the defect can involve closure of the defect with sutures or fasteners but generally involves placing a surgical prosthetic such as a mesh patch over the defect, and attaching the mesh patch to the abdominal wall or inguinal floor with conventional suture or with surgical fasteners. The mesh patch acts as a barrier and prevents expulsion of bowel through the defect. Suturing of the mesh patch to the inguinal floor can be well suited to open procedures but can be much more difficult and time consuming with endoscopic procedures. With the adoption of endoscopic surgery, endoscopic surgical instruments that apply surgical fasteners can be used. However, the tissue of the inguinal floor may offer special challenges to the surgeon when a needle or fastener is used to penetrate structures such as Cooper's ligament.

At present, there are a variety of surgical instruments and fasteners available for the surgeon to use in an endoscopic or open procedure to attach the mesh patch to the abdominal wall or inguinal floor. One of the earliest types of endoscopic surgical instruments used is a surgical stapler. A plurality or stack of these unformed staples may be generally contained within a stapling cartridge in a serial fashion, and may be sequentially advanced or fed within the instrument by a spring mechanism. A secondary valving or feeding mechanism may be employed to separate the distal-most staple from the stack, to hold the remainder of the spring loaded stack, and may be used to feed the distal-most staples into the staple forming mechanism. Feeding mechanisms of this type are found in U.S. Pat. No. 5,470,010 to Rothfuss et al., and in U.S. Pat. No. 5,582,616, also to Rothfuss et al.

Another hernia mesh attachment instrument uses a helical wire fastener that resembles a small section of spring. Multiple helical wire fasteners may be stored serially within the 5 mm shaft, and may be corkscrewed or rotated into tissue. A load spring may be used to bias or feed the plurality of helical fasteners distally within the shaft. A protrusion extends into the shaft to possibly prevent the ejection of the stack of fasteners by the load spring and may permit passage of a rotating fastener. Instruments and fasteners of these types are found in U.S. Pat. No. 5,582,616 to Bolduc et al., U.S. Pat. No. 5,810,882 to Bolduc et al., and in U.S. Pat. No. 5,830,221 to Stein et al.

Whereas the above surgical instruments may be used for hernia fastening applications, they use a spring mechanism to feed a plurality of fasteners through the surgical instrument. Spring mechanisms typically use a long soft coil spring to push a stack of fasteners through a guide or track within the shaft of the surgical instrument. These types of feeding mechanisms may be generally simple and reliable, but may require an additional secondary valving mechanism or protrusion to separate and feed one fastener from the stack.

Other surgical fasteners may be used for hernia mesh attachment but utilize either a reloadable single shot instrument or a rotary magazine that holds a small number of fasteners. These types of surgical fastening instruments can be found in U.S. Pat. Nos. 5,203,864 and 5,290,297, both to Edward Phillips. These instruments have not gained acceptance by the surgical community, possibly due to their single shot capabilities and the large size of the rotary magazine, which can restrict such an instrument to an open procedure.

Whereas all the above surgical instruments may be used for hernia fastening applications, they either use a spring mechanism to feed the plurality of fasteners through the surgical instrument, or a rotary magazine in lieu of a feeding mechanism. Other types of surgical fasteners may be available, such as surgical clips, and they can utilize feeding mechanisms that do not require the use of a spring to feed the clips distally. A reciprocating feeding mechanism is described in U.S. Pat. Nos. 5,601,573; 5,833,700; and 5,921, 997 to Fogelberg et al. The Fogelberg et al. references teach a clip applier with a feeding mechanism that utilizes a reciprocating feed bar to feed a serial stack of clips. A feeder shoe may operably engage with and move with the distally moving feed bar and may slidingly engage with the proximally moving feed bar. Thus, the feeder shoe may index or push the stack of clips distally with the distally moving feed bar and remains stationary relative to the proximally moving feed bar. A valving mechanism may be also required to separate the distal-most clip from the stack and to hold the stack stationary as the distal-most clip may be applied onto a vessel. Whereas the Fogelberg et al. references teach a reciprocating feeding mechanism with a single reciprocating member, they do not teach the use of the clip applier in the attachment of hernia mesh, nor do they teach the individual driving or feeding of each clip by a moving member.

U.S. Pat. No. 3,740,994 to DeCarlo Jr. discloses a reciprocating feeding mechanism that indexes a plurality of staples or clips, and readies them for discharge by reciprocating one of a pair of opposing leaf spring assemblies. The staples reside serially within a guide rail with a fixed leaf spring assembly extending into the plane of the guide rail. A reciprocating leaf spring assembly may extend inwardly towards the fixed leaf spring assembly. As the reciprocating leaf spring assembly moves distally, each of individual leaf springs of the assembly may engage a staple and move it distally. The distally moving staples deflect the local individual leaf springs of the fixed leaf spring assembly, and the deflected leaf springs may return to the un-deflected position after passage of the staple. As the moving leaf spring assembly moves proximally, the leaf springs of the fixed leaf spring assembly hold the staples stationary and prevent proximal movement thereof. A secondary guide rail and valving mechanism may be provided to separate a single staple from the stack for forming and can hold the stack of staples stationary as the single clip is formed.

Additionally, similar feeding mechanisms are disclosed in U.S. Pat. No. 4,478,220 to DiGiovanni et al. and U.S. Pat. No. 4,471,780 to Menges et al. Both of these related patents teach a reciprocating feeding mechanism that uses one fixed member and one reciprocating member to feed or index a plurality of clips distally. Angled flexible fingers may be hingedly attached to the reciprocating member and operatively engage the clips when moving distally, and slidingly engage with the clips when moving proximally. The angled flexible fingers within the fixed member deflect out of the way when the clips move distally and spring up to stop proximal movement of the clip after the clip has passed. A secondary valving mechanism is also disclosed.

Commonly assigned U.S. Pat. No. 7,485,124, the disclosure of which is hereby incorporated by reference herein, teaches a device for delivering a plurality of individual surgical fasteners. In one embodiment, the delivery device includes a drive mechanism having distal and proximal ends. The drive mechanism has a moving member and a fixed opposing member, whereby the moving member is moveable proximally and distally with respect to the delivery device. The moving member has a sharpened distal end for piercing tissue. The device includes at least one surgical fastener located between the first and the second members. Each of the at least one surgical fasteners has a proximal end and a distal end. The device also has an actuator having at least two sequential positions. A first position for moving the moving member distally and piercing tissue, and a second position for moving the moving member proximally, thereby deploying the distal end of the fastener.

Tacks for fixing meshes used laparoscopically have generally been made of metal, such as stainless steel, nitinol, or titanium. The metal tacks were necessary to provide for sufficient holding strength, penetration of various prosthetic meshes, and for ease of manufacture. Until recently, there were no absorbable tacks available on the market, and surgeons could only use absorbable sutures in order to provide a fixation means that did not permanently stay in the body. However, using sutures is exceedingly difficult for laparoscopic procedure, and so they are generally not used unless the repair is done in an open fashion. With surgical trends leading to more minimally invasive techniques with minimum foreign body accumulation, an absorbable tack with minimum profile that can be applied laparoscopically is needed.

Commonly assigned U.S. Pat. No. 8,920,439, the disclosure of which is hereby incorporated by reference herein, discloses an applicator instrument for dispensing surgical fasteners having an elongated shaft with a proximal shaft section and a distal shaft section. The applicator instrument has an articulation controller coupled with the distal shaft section for selectively changing the angle between the distal shaft section and the proximal shaft section. The articulation controller has at least one flexible linkage extending through the shaft and has a proximal end connected with an actuator and a distal end connected with the distal shaft section. The actuator is mounted on a housing for sliding between proximal and distal ends of the housing for moving the at least one flexible linkage in proximal and distal directions. Surgical fasteners are disposed within elongated shaft for being dispensed one at a time from the distal end of the elongated shaft.

In spite of the above advances, intra-operative conditions during laparoscopic surgery remain challenging for the surgeon. There is a need for flexibility, both with respect to surgeon ergonomics and fastener options. Regarding ergonomics, there remains a need for applicator instruments for dispensing surgical fasteners that have improved ergonomics, that enable ipsillateral (same side) mesh tensioning, and that provide maneuverability both inside and outside of a body cavity. There also remains a need for applicator instruments for dispensing surgical fasteners that have an optimal distal shaft strength when the shaft is articulated, and that provide pre-defined articulation angles for simplifying the device complexity and the user experience. There also remains a need for applicator instruments that have improved ergonomics for accommodating a diverse range of trocar placements, including both midline and lateral trocar placements. In addition, there is a need for tailored fastener solutions to accommodate the diverse needs of patients. Moreover, related to this need, there is a need to reduce procedural costs and increase flexibility during surgical procedures.

SUMMARY OF THE INVENTION

In one embodiment, an applicator instrument having a reconfigurable handle for dispensing surgical fasteners preferably includes a housing, an elongated shaft extending from a distal end of the housing, a handle coupled with a proximal end of the housing, a trigger coupled with the handle, a firing system disposed within the housing, the firing system including an energy storing assembly, and a gear train disposed within the handle and coupled with the trigger. In one embodiment, the trigger is squeezable for storing energy in the energy storing assembly. In one embodiment, the applicator instrument preferably includes a handle reconfiguration actuator having a first position for locking the handle in place relative to the housing and a second position for enabling the handle to rotate relative to the housing between a pistol configuration and an in-line configuration.

In one embodiment, the elongated shaft desirably has a proximal end secured to the distal end of the housing, a distal end, and a longitudinal axis extending between the proximal and distal ends thereof. In one embodiment, the handle has a longitudinal axis that is orthogonal to the longitudinal axis of the elongated shaft when the handle is in the pistol configuration and the longitudinal axis of the handle is generally parallel to the longitudinal axis of the elongated shaft when the handle is in the in-line configuration.

In one embodiment, when the handle reconfiguration actuator is in the first position, the handle is coupled with the firing system in the housing. In one embodiment, when the handle reconfiguration actuator is in the second position, the handle is decoupled from the firing system in the housing for enabling the handle to rotate relative to the housing.

In one embodiment, the trigger is coupled with the handle and moves simultaneously with the handle as the handle rotates between the pistol configuration and the in-line configuration.

In one embodiment, the proximal end of the housing has a concave surface and a distal end of the handle has a convex surface that matches the curve of the concave surface for guiding rotation of the handle between the pistol and in-line configurations.

In one embodiment, the proximal end of the housing comprises a series of spaced reconfiguration notches that are arrayed in an arc-shaped pattern and that are utilized for positioning the handle at different angles relative to the housing.

In one embodiment, the applicator instrument desirably has a slider that extends between the handle reconfiguration actuator and the reconfiguration notches at the proximal end of the housing. In one embodiment, the slider has a proximal end that is engaged by the handle reconfiguration actuator and a distal end that is adapted to be seated in the reconfiguration notches.

In one embodiment, when the handle reconfiguration actuator is in the second position, an underside of the handle reconfiguration actuator applies a force on the slider that move the distal end of the slider away from one of the reconfiguration notches for enabling the handle to be rotated relative to the housing. In one embodiment, when the handle reconfiguration actuator is in the first position, the underside of the handle reconfiguration actuator removes the force on the slider so that the distal end of the slider may be seated within one of the reconfiguration notches for locking the position of the handle relative to the housing.

In one embodiment, the applicator instrument desirably includes a slider return spring in contact with the slider that normally urges the distal end of the slider to be seated within one of the reconfiguration notches. In one embodiment, the slider return spring is compressed by the force applied by the underside of the handle reconfiguration actuator when the handle reconfiguration actuator is in the second position.

In one embodiment, the gear train preferably has a drive gear having a major face, a raised ring on the major face, and a ring opening formed in the raised ring to define a non-continuous portion of the raised ring and a closed portion of the raised ring.

In one embodiment, the drive gear has an interruption in the gear tooth pattern. When the trigger is open, the drive gear is disengaged from a mating gear, preventing trigger rotation when the handle is reconfigured.

In one embodiment, the handle reconfiguration actuator desirably includes a locking projection that extends from an underside of the handle reconfiguration actuator.

In one embodiment, when the handle reconfiguration actuator is in the second position for rotating the handle relative to the housing, the locking projection of the handle reconfiguration actuator desirably extends into the ring opening of the raised ring on the drive gear for blocking rotation of the drive gear, which, in turn, prevents further squeezing of the trigger toward the handle.

In one embodiment, when the trigger is squeezed for commencing a firing cycle, the closed portion of the raised ring on the drive gear blocks the handle reconfiguration actuator from being moved into the second position so that the handle may not be rotated relative to the housing after commencement of the firing cycle.

In one embodiment, a cartridge containing a plurality of stacked surgical fasteners is inserted into the housing for providing surgical fasteners adapted to be dispensed from a distal end of the elongated shaft.

In one embodiment, an articulating lever is provided on the housing and coupled with the elongated shaft for moving the distal end of the elongated shaft between a straight configuration and an articulated configuration.

In one embodiment, an applicator instrument having a reconfigurable handle for dispensing surgical fasteners includes a housing having a proximal end and a distal end, an elongated shaft extending from the distal end of the housing, a handle coupled with the proximal end of the housing, a trigger coupled with the handle, a firing system disposed within the housing, the firing system including an energy storing assembly, and a gear train disposed within the handle and coupled with the trigger, whereby the trigger is squeezable for storing energy in the energy storing assembly.

In one embodiment, the proximal end of the housing has a concave surface and a series of spaced reconfiguration notches that are utilized for positioning the handle at different angular configurations relative to the proximal end of the housing. In one embodiment, a distal end of the handle has a convex surface that matches the curve of the concave surface of the housing for guiding rotation of the handle relative to the proximal end of the housing.

In one embodiment, a handle reconfiguration actuator is provided on the handle. In one embodiment, the handle reconfiguration actuator has a first position for locking the handle in place in one of the reconfiguration notches and a second position for enabling the handle to rotate to the different angles relative to the housing.

In one embodiment, when the handle reconfiguration actuator is in the second position, the handle is rotatable between a pistol configuration and an in-line configuration.

In one embodiment, the gear train preferably includes a drive gear having a major face, a raised ring on the major face, and a ring opening formed in the raised ring to define a non-continuous portion of the raised ring and a closed portion of the raised ring.

In one embodiment, the handle reconfiguration actuator includes a locking projection that extends from an underside of the handle reconfiguration actuator. In one embodiment, when the handle reconfiguration actuator is in the second position for rotating the handle relative to the housing, the locking projection of the handle reconfiguration actuator extends into the ring opening of the raised ring on the drive gear for blocking rotation of the drive gear, which, in turn, prevents further squeezing of the trigger toward the handle.

When the trigger is in this position, the drive gear is disengaged from its mating gear.

In one embodiment, when the trigger is squeezed for commencing a firing cycle, the closed portion of the raised ring on the drive gear blocks the handle reconfiguration actuator from being moved into the second position so that the handle may not be rotated relative to the housing after commencement of the firing cycle. When the trigger is squeezed, the drive gear is engaged with its mating gear.

In one embodiment, a method of using an applicator instrument having a reconfigurable handle for dispensing surgical fasteners preferably includes providing an applicator instrument including a housing, an elongated shaft extending from the housing, a handle coupled with a proximal end of the housing, a trigger coupled with the handle, a firing system including an energy storing assembly disposed within the housing, and a gear train disposed within the handle and coupled with the trigger.

In one embodiment, the method includes providing a handle reconfiguration actuator on the handle having a first position for locking the handle in place relative to the housing and a second position for rotating the handle relative to the housing.

In one embodiment, the method preferably includes moving the handle reconfiguration actuator into the second position and rotating the handle into a first angular configuration relative to the housing, and after rotating the handle into the first angular configuration, moving the handle reconfiguration actuator into the first position for locking the handle in place in the first angular configuration.

In one embodiment, the method includes with the handle locked in place in the first angular configuration, squeezing the trigger for storing energy in the energy storing assembly of the firing system. In one embodiment, after squeezing and releasing the trigger, the handle reconfiguration actuator is moved into the second position and the handle is rotated from the first angular configuration into a second angular configuration relative to the housing. In one embodiment, with the handle in the second angular configuration, the handle reconfiguration actuator is moved to the first position for locking the handle in place in the second angular configuration.

In one embodiment, a method includes inserting a cartridge containing a plurality of stacked surgical fasteners into the housing, and with the handle in the second angular configuration, squeezing the trigger for dispensing a first surgical fastener of the stacked surgical fasteners from a distal end of the elongated shaft. In one embodiment, after dispensing the first surgical fastener, the handle is moved into another angular configuration and the trigger is squeezed for dispensing a second surgical fastener of the stacked surgical fasteners from the distal end of the elongated shaft.

In one embodiment, a method preferably includes providing an articulation lever on the housing that is coupled with the elongated shaft for moving the distal end of the elongated shaft between a straight configuration and an articulated configuration, and with the elongated shaft in the straight configuration and the handle in the first angular configuration, squeezing the trigger for dispensing a surgical fastener.

In one embodiment, a method may include engaging the articulation lever for moving the distal end of the elongated shaft into the articulated configuration and again squeezing the trigger with the handle in the first angular configuration for dispensing a surgical fastener from the distal end of the articulated elongated shaft.

In one embodiment, a method desirably includes moving the handle into the second angular configuration and again squeezing the trigger for dispensing a surgical fastener from the distal end of the articulated elongated shaft, and engaging the articulation lever for moving the distal end of the elongated shaft into the straight configuration and again squeezing the trigger with the handle in the second angular configuration for dispensing a surgical fastener from the distal end of the straight elongated shaft.

In one embodiment, an applicator instrument for dispensing surgical fasteners during surgical procedures has a reconfigurable handle that may be moved between a pistol configuration, an in-line configuration, and an inverted pistol. The applicator instrument having a reconfigurable handle is particularly useful during laparoscopic procedures such as hernia repair procedures where ergonomics and instrument maneuverability are critical.

In one embodiment, the applicator instrument includes a distal housing assembly, a proximal handle assembly, a pivoting connection between the distal housing assembly and the proximal handle assembly, and a locking element for securing the distal housing assembly and the proximal handle assembly at a plurality of angular positions relative to each other In one embodiment, the locking element includes a button located on the proximal handle assembly that may be engaged for enabling the proximal handle assembly to be pivoted about the distal housing assembly. The proximal handle assembly is reconfigurable so that it may be placed in a plurality of positions relative to the housing assembly, including a pistol configuration, an in-line configuration, or an inverted pistol configuration. In one embodiment, the proximal handle assembly can be adjusted through a range of angles between 90 and 180 degrees.

In one embodiment, the applicator instrument desirably includes a gear train that is used to actuate a firing system for dispensing surgical fasteners. In one embodiment, the gear train preferably includes a first portion of a gear train located in the proximal handle assembly, which is configured to engage a second portion of a gear train located in the distal housing assembly in order to actuate the firing system. In one embodiment, at least one gear in the distal housing assembly is concentric with the axis of rotation of the reconfiguration pivot.

In one embodiment, the proximal handle assembly has a trigger that may be squeezed for activating the gear train. In one embodiment, during reconfiguration of the proximal handle assembly relative to the distal housing assembly, the gear train in the proximal handle assembly is disengaged from the gear/gear train in the distal housing assembly to allow for the reconfiguration while not affecting the stroke of the trigger/gear train.

In one embodiment, when the trigger has been squeezed to commence a firing cycle, the reconfiguration button is blocked to prevent reconfiguration of the proximal handle assembly relative to the distal housing assembly during the firing cycle.

In one embodiment, when the reconfiguration button is depressed for changing the angle of the proximal handle assembly relative to the distal housing assembly, the trigger or gear train is blocked to prevent firing of the applicator instrument prior to completing the reconfiguration of the proximal handle assembly.

Although the present invention is not limited by any particular theory of operation, it is believed that providing applicator instruments having reconfigurable handles will improve the ergonomics of surgical procedures and improve the maneuverability of the instruments. For example, a pistol configuration may be preferred for Totally Extra-Peritoneal (TEP) Inguinal repair procedures because the trocars are typically placed near the patient's midline and the surgeon is typically postured to hold instruments above the patient. In contrast, either a pistol or in-line configuration may be preferred for Trans-Abdominal Pre-Peritoneal (TAPP) inguinal and ventral repairs. For both of these repairs, the trocars are typically placed near the patient's side (i.e., lateral placement) and the surgeon will be working across the patient's body. On the contra-lateral side, either a pistol or in-line configuration may be advantageous. However, on the ipsilateral side, an in-line position provides the benefit of allowing the surgeon to maintain a neutral wrist position while leveraging the device to provide preload to the distal end just before firing.

Thus, in one embodiment, a single applicator instrument having a reconfigurable handle may be used for midline and lateral trocar placements, providing versatility and improved ergonomics.

In one embodiment, a cartridge contains a plurality of surgical fasteners that are stacked atop one another within the cartridge and urged toward a lower end of the cartridge by a spring. In one embodiment, an applicator may be used with different cartridges having different types of surgical fasteners. In one embodiment, an applicator instrument may have a cartridge receiving port that is located at the proximal end of the applicator instrument that is adapted to receive the different cartridges. In one embodiment, with an elongated shaft of the applicator instrument remaining inside a patient, the different cartridges may be exchanged between firing cycles so that a first type of surgical fastener may be fired during a first firing cycle and a second type of surgical fastener may be fired during a second firing cycle. The ability to change cartridges without removing the distal end of the applicator instrument from the patient preferably enhances efficiency, safety and maintains sterile conditions.

In one embodiment, there is no reconfigurable handle. Instead, the distal housing assembly is docked directly to the arm of a surgical robot. The surgical robot then controls the articulating and firing functions through a standard interface on the robotic arm. The user can still change the cartridge and attach new cartridges to the housing assembly. In this manner, the instrument can be re-loaded or used to deliver a variety of surgical fasteners without changing the applicator instrument attached to the robotic arm.

In one embodiment, the proximal handle assembly has a reconfiguration button having a reconfiguration slider coupled therewith that is configured to engage reconfiguration notches located on the distal housing assembly. In one embodiment, when the reconfiguration button is depressed, the reconfiguration slider is moved away from engagement with one of the reconfiguration slots so that the proximal handle assembly may be pivoted relative to the distal housing assembly. When the reconfiguration button is released, a slider spring normally urges the slider to return to a locked position. In one embodiment, during reconfiguration of the handle, the gear train between the handle and the housing is decoupled.

In one embodiment, when the reconfiguration button is depressed, the deployed reconfiguration button blocks activation of the trigger or commencement of a firing cycle. Thus, in one embodiment, the applicator instrument may not be fired as the position of the handle is being reconfigured.

In one embodiment, when the trigger is squeezed for moving the gear train or commencing a firing cycle, the deployed trigger prevents a handle reconfiguration actuator (e.g., a depressible element or button) from being moved (e.g., depressed). Thus, in one embodiment, the position of the handle may not be reconfigured as the applicator instrument is being fired or after the commencement of a firing cycle.

In one embodiment, an applicator instrument for dispensing surgical fasteners engages a single surgical fastener from a location at or near the proximal end of the instrument and advances the surgical fastener to the distal end of the instrument. In one embodiment, a driving element, such as a spring, provides a pre-determined force, resulting in a consistent delivery of the surgical fastener. Over the course of the firing, this force accelerates the fastener, increasing its velocity and momentum allowing it to penetrate various meshes and tissues.

In one embodiment, the applicator instrument for delivering surgical fasteners preferably includes an elongated member, such as an elongated shaft, having a proximal end and a distal end, a surgical fastener (e.g., a tissue fastener or surgical staple) located adjacent the proximal end of the elongated member, and a mechanism for transporting the surgical fastener from the proximal end of the elongated member to the distal end of the elongated member and into tissue.

In one embodiment, the applicator instrument preferably includes a cartridge holding one or more surgical fasteners. In one embodiment, a plurality of surgical fasteners are stacked atop or adjacent one another within a spring-loaded cartridge. In one embodiment, the cartridge may be positioned adjacent the proximal end of the elongated member.

In one embodiment, the applicator instrument preferably includes an element for engaging a single surgical fastener held by the cartridge so that the singulated surgical fastener may be engaged by a firing system and/or advanced toward the distal end of the elongated member. In one embodiment, the single surgical fastener may be stripped from the bottom of a stack of surgical fasteners.

In one embodiment, the applicator instrument desirably has a flexible member having a distal end for transporting the surgical fastener from the proximal end of the elongated member to the distal end of the elongated member. In one embodiment, the flexible member may be made of plastic, metal, other suitable materials, and/or combinations thereof. In one embodiment, the flexible member may be planar in cross section, or curved in cross section for enhancing the column strength of the flexible member.

In one embodiment, the flexible member has a distal end that pushes the surgical fastener in a distal direction. In one embodiment, the flexible member preferably has a proximal end that may be retracted and stored in a coiled manner (e.g., on a storage reel). In one embodiment, the flexible member may have features for engaging with a drive wheel. These features may be holes, pockets, or protrusions. In one embodiment, the one or more drive wheels may have surfaces designed to frictionally engage with the flexible member.

In one embodiment, the applicator instrument desirably has a drive wheel (e.g., cogged wheel or friction wheel) that engages a section of the flexible member that is proximal to the distal end of the flexible member. In one embodiment, the drive wheel may be driven by a constant torque spring, a torsion spring, an electrically powered motor, mechanically, electrically, electro-mechanically, and/or pneumatically, or a combination of the above. In one embodiment, the drive wheel may be driven by an external element, for example, by rotary motion from the arm of a robotic surgery system or by compressed air. In one embodiment, the drive wheel may be driven by a stored energy system such as a pre-wound spring.

In one embodiment, the flexible member may be directly connected to a constant torque spring and wound onto the same reel that is coupled with the constant torque spring, therefore not requiring a drive wheel component. In one embodiment, the flexible member and the constant torque spring may be layered together on the same coil.

In one embodiment, a spring such as a power spring or a constant torque spring may be connected to the proximal end of the flexible member to aid in retracting the flexible member from an extended position to a retracted position, and to provide tension to prevent billowing of the flexible member away from the reel during operation. In one embodiment, billowing is preferably minimized to reduce drag or losses in the system. In one embodiment, the constant torque spring or torsion spring desirably stores energy in response to squeezing a trigger or actuator coupled with the handle of the applicator instrument.

In one embodiment, the applicator instrument may have a positive stop coupled with or that contacts the flexible member or the drive wheel to limit or control distal movement of the flexible member. In one embodiment, a positive stop may be located at the distal end of the elongated member or in the housing portion of the applicator instrument, or both. A distal stop provides the benefit of precisely controlling the expulsion distance that the surgical fastener extends from the distal end of the device. A stop in the housing end of the device can engage directly with the flexible member, a storage member, or a drive wheel. If engaged with the drive wheel, it can provide the benefit of reducing compressive loads on the flexible member when left in the ready to fire position with the flexible member extended. Alternatively, a stop in the housing end of the device may engage with the storage reel or flexible member to prevent over-rotation of the storage reel and subsequent damage to the proximal end of the flexible member. For either proximal stop, it is critical to delay the engagement of the stop until after the surgical fastener has sufficient stroke to embed into tissue. This also provides time for the length of the flexible member to compress, dampening the impact at the proximal stop.

In one embodiment, the flexible member is capable of elastically compressing and buckling within the constraints of a guide member, which preferably limits the force or stroke that may be applied to the surgical fastener.

In one embodiment, a cartridge may have tissue fasteners stacked at any angle within a magazine (e.g. horizontal, vertical or any angle in between), relative to the orientation of the elongated shaft.

In one embodiment, surgical fasteners may be singulated or stripped from the cartridge utilizing the flexible member. In one embodiment, a distal end of the flexible member includes a protruding portion (e.g., a solid or compressible fin) that pushes/strips a single surgical fastener from the cartridge to singulate the surgical fastener and move it into a cannula for delivery. In one embodiment, an insertion tool or insertion guide is affixed to the distal end of the flexible member. In one embodiment, the insertion tool is a feature of the flexible member, such that the flexible member and the insertion tool are a single component. The insertion tool may include the fin or a stripper ramp that engages a surgical fastener for stripping the surgical fastener from the bottom of a surgical fastener stack.

In one embodiment, a dual path arrangement is utilized for advancing a surgical fastener toward a distal end of the elongated member. In one embodiment, the dual path arrangement includes a first path in which the distal end of the flexible member strips off a single tissue fastener, and positions the tissue fastener in a staging position on a second path. A section of the flexible member proximal to the distal end of the flexible member drops down to the second path for subsequent deployment of the tissue fastener.

In one embodiment, a rotary motion element may be used to strip a single surgical fastener from a cartridge and place the surgical fastener in a staging position for being engaged by a distal end of the flexible member.

In one embodiment, an applicator instrument for dispensing surgical fasteners preferably includes a user actuated trigger that drives a gear train to rotate a storage reel, which, in turn, retracts a flexible member from a distal end of a cannula onto the storage reel. In one embodiment, the storage reel for the flexible member is a proximal storage reel located at the proximal end of the distal housing assembly of the instrument.

In one embodiment, retraction of the flexible member also rotates a drive wheel through a cogged interface or friction interface between the flexible member and the drive wheel. The rotation of the drive wheel winds a constant torque spring from a spool onto the drive wheel for storing energy in the constant torque spring. When the flexible member reaches a pre-determined retracted position behind a surgical fastener cartridge located in the housing or the handle, the gear train disengages and the portion of the constant torque spring that was wound onto the drive wheel unwinds back to the spool, which, in turn, rotates the drive wheel. The rotation of the drive wheel pulls the flexible member off the storage reel and drives the flexible member distally through the cogged interface and the flexible member strips a tissue fastener from the cartridge and pushes the tissue fastener to the distal end of the cannula (e.g., elongated shaft) and into tissue.

In one embodiment, the applicator instrument may have a drive train that is directly connected to the drive wheel to wind the constant torque spring from the spool onto the drive wheel. In this embodiment, it is preferable to utilize a power spring or other means to wind and manage the flexible member as it is urged proximal onto the storage reel.

In one embodiment, the flexible member and surgical fastener may be continually accelerated as the surgical fastener is pushed down the length of the elongated shaft. This acceleration increases the velocity and momentum of the fastener, flexible member, and drive wheel system. A minimum velocity and inertia are necessary to allow the fastener to pierce meshes and abdominal wall tissue.

In one embodiment, the flexible member is adapted to push the tissue fastener via geometry that engages with the tissue fastener or via one or more flat contact surfaces.

In one method of dispensing a surgical fastener, similar to a "bow and arrow" method, the flexible member may be assembled at the distal end of the elongated member and, during the firing stroke, be drawn back to the handle to engage and deliver the tissue fastener. In this embodiment, the flat flexible member remains in a flat configuration during storage, reducing the likelihood that the flexible member will take a permanent set. In one method of dispensing a surgical fastener, referred to as a "coiled snake" method, the flexible member may start in the handle and during the firing stroke, experience a force to deliver the tissue fastener to the distal end of the elongated member, and then return back to the handle.

In one embodiment, the flexible member may be pulled from and return to a reel located in the handle. In one embodiment, the reel may have a power spring or the flexible member may be self-coiling to help retract the flexible member and to provide tension to prevent billowing of the flexible member away from the reel during operation. In one embodiment, the drive system may be spring powered, electrically powered, air powered, hydraulically powered, etc.

The flexible member may be fed through a straight cannula, a curved cannula, or through a cannula with an articulating end.

In one embodiment, an applicator instrument having an articulating distal end may have a bi-stable configuration that utilizes an over-center spring to bias the system toward no articulation of the elongated shaft or full articulation of the elongated shaft. The bi-stable configuration prevents the distal end of the elongate shaft from existing in an intermediate state where the articulation is not as stable.

In one embodiment, the applicator instrument has a user interface (e.g, an articulation control lever) that is in a first position (e.g., horizontal) when the shaft is not articulated and a second position (e.g., vertical) when the shaft is fully articulated, thereby mirroring the configuration of the articulated end of the shaft. The user interface for controlling articulation preferably provides the user with visual feedback regarding the configuration of the articulated end of the shaft when the shaft is inserted into a trocar and is not visible. Although the present invention is not limited by any particular theory of operation, it is believed that the bi-stable configuration provides a user experience that guides the user toward one of the two articulation positions and does not allow the user to leave the articulation of the shaft in an intermediate, state. It is also considered that a bi-stable system will reduce the mental task load of the surgeon and simplify the user experience by simplifying the articulation control to a simple toggle.

In one embodiment, an applicator instrument maintains the integrity of a quantity of surgical fasteners during handling and allows the surgical fasteners to be removed one at a time for implantation by the instrument. In one embodiment, a protruding portion of a flexible member pushes a single tissue fastener from a cartridge to singulate the surgical fastener and move it into a cannula for delivery from a distal end of an elongated shaft. In one embodiment, surgical fasteners are stacked in the cartridge and a constant force spring is used to move the fasteners toward a staging location in the cartridge. In one embodiment, the surgical fasteners are desirably restricted and only allowed to move in a direction toward the staging location in the cartridge. The staging location in the cartridge preferably allows a single surgical fastener in the staging location to move in a direction parallel to the flexible member and then transition into the cannula.

In one embodiment, the distal end of the flexible member includes an insertion tool having a protruding portion shaped like a "shark fin" that is configured to engage with the back of a surgical fastener in the staging location of the cartridge and push the surgical fastener into the cannula for delivery into tissue. In one embodiment, the channel through the cannula has a relief groove for the fin.

In one embodiment, a cartridge containing surgical fasteners may have one or more orientation indicators that direct a user as to the correct orientation for inserting the cartridge into the applicator instrument. In one embodiment, the cartridge may have Poke-a-Yoke features so that the cartridge cannot be inserted incorrectly. In one embodiment, the cartridge may have a color indicator that indicates the type of surgical fasteners loaded into the cartridge. In one embodiment, the color indicator may be printed onto a label placed on the cartridge or the color indicator may be the color of the material used to make the cartridge. In one embodiment, the cartridge may have a snap feature that provides tactile feedback that the cartridge is fully/properly inserted into the applicator instrument. In one embodiment, the applicator instrument may have a cartridge release that may be engaged for locking or inserting the cartridge into the housing of the applicator instrument or unlocking and removing the cartridge from the housing of the applicator instrument. In one embodiment, the cartridge release may be on the cartridge itself.

In one embodiment, an applicator instrument has a cartridge system that utilizes a single linear path to strip a surgical fastener from the cartridge and place the stripped surgical fastener into a proper location for being delivered from a distal end of the instrument.

In one embodiment, prior to firing the applicator instrument, surgical fasteners are stacked in a cartridge. A pusher is staged distal to the surgical fastener, an elevator is aligned with the lower end of the cartridge, and a slide is in a proximal-most position. During a first stage of a firing cycle, as a user squeezes a trigger, the pusher pushes a single surgical fastener out of the cartridge and into the elevator, and the slide moves distally. During a second stage of the firing cycle, as the users fully squeezes the trigger, the pusher stops moving once the surgical fastener is fully loaded into the elevator, and the elevator moves down into alignment with the path of the distal end of the flexible member, on top of a lower guide. During a third stage of a firing cycle, the slide is in a distal-most position, the elevator is all the way down, and the flexible member moves along the lower guide for delivering the surgical fastener down the elongated shaft.

In one embodiment, an applicator instrument for dispensing surgical fasteners has a cartridge system whereby the flexible member utilizes a first path to strip a surgical fastener from the cartridge and advance the surgical fastener to the distal end of the elongated shaft, and utilizes a second, different path for returning the flexible member to a location that is proximal to the cartridge (e.g., a "Racetrack" path).

In one embodiment, an applicator instrument may have a cartridge system that utilizes a rotary motion member to strip/singulate a surgical fastener and place the surgical fastener into a proper location for being engaged by a distal end of the flexible member. As a result of using a rotary motion element, surgical fasteners may be stacked inside the cartridge in any orientation relative to the path of the flexible member. In one embodiment, the rotary motion may rotate a surgical fastener through any angle necessary to bring it in-line with the distal end of the flexible member (e.g., 90 degree rotation).

In one embodiment, a cartridge system that stores surgical fasteners in a rotary drum may be side loaded onto an applicator instrument or may be top loaded onto the applicator instrument.

In one embodiment, an applicator instrument for dispensing surgical fasteners has an elongated shaft that may be articulated for moving between a straight configuration and an articulated, curved, or angled configuration. In one embodiment, the articulating shaft provides a high level of cannula rigidity in both the articulated configuration and the straight configuration, especially where high axial/lateral forces or pressure is exerted on the distal tip of the cannula during tack/strap application in hernia fixation or whenever a counter pressure on the cannula tip is applied (e.g., during mesh manipulation with the distal end of the instrument).

In one embodiment, an applicator instrument for dispensing surgical fasteners has an articulating shaft. The articulating instrument preferably includes an elongated shaft having a proximal end, a distal end, and a longitudinal axis extending between the proximal and distal ends. The applicator instrument preferably has a handle attached to the proximal end of the shaft, a cam assembly attached to the handle, at least one segmented member on the distal end of the elongated shaft, and at least one band having a proximal end and a distal end. In one embodiment, the distal end of the band is attached to the at least one segmented member at the distal end of the elongated shaft, and the proximal end of the band is adjustably attached to the cam assembly such that rotation of the cam assembly results in movement of the band along the longitudinal axis of the shaft resulting in articulation of the segmented member.

In one embodiment, the proximal end of the band is attached to a yoke, which, in turn, is attached to the cam assembly. In one embodiment, the yoke can pivot around a central axis in response to movement of the cam assembly.

In one embodiment, an articulation system preferably includes two bands, each having one end attached to the at least one segmented member on opposite sides of the at least one segmented member and the respective proximal ends of the bands are attached to the rotatable yoke.

In one embodiment, a proximal end of an upper band is connected with a first slider, and the first slider is connected with the rotatable yoke. In one embodiment, a proximal end of a lower band is connected with a second slider, and the second slider is connected with the rotatable yoke. The connection distance between the first and second sliders and the yoke may be adjusted for controlling the tension applied onto the upper and lower bands.

In one embodiment, the first slider is adjusted in a proximal direction to impart a first tension on the upper band. Similarly, the second slider is adjusted in a proximal direction to impart a second tension on the lower band. In one embodiment, the second tension on the lower band is less than the first tension on the upper band.

In one embodiment, the cam engages a spring that normally urges the cam into one of two stable positions, a stable first position or a stable second position. In one embodiment, moving the cam to the second position increases the tension on the upper band while reducing the force on the lower band, which results in articulation of the at least one articulating segment at the distal end of the elongated shaft.

In one embodiment, at least one articulating segment is rotatably attached to the distal end of the elongated shaft so that rotation of the shaft is limited or controlled by features on the at least one articulating segment. In one embodiment, when the cam is in the second position, rotation of the distal end of the shaft is limited to a pre-defined angle by features on the at least one articulating segment. In one embodiment, the pre-defined rotation is preferably 60 degrees or any value between 0 and 90 degrees.

In one embodiment, an applicator instrument for dispensing surgical fasteners has an articulating shaft. In one embodiment, the applicator instrument includes a proximal shaft section having a proximal end, a distal end, and a longitudinal axis, and a handle attached to the proximal end of the proximal shaft section. The instrument preferably includes segmented members coupled with the distal end of the proximal shaft section. Each pair of segmented members accommodates a specific rotation limit. The instrument preferably has two articulation bands disposed within the segmented members. In one embodiment, a cam system is moved from a first position into a second position to tension the upper band while simultaneously releasing the lower band to force the segmented members into the articulated configuration. In one embodiment, the cam system is moved from the second position back to the first position to tension the lower band while simultaneously releasing the upper band to return the segmented members to a non-articulated position (e.g., straight).

In one embodiment, an over-center spring element automatically forces the articulating, segmented members into either the articulated or straight configuration. In one embodiment, the articulation system includes adjustment mechanisms for adjusting the level of tension applied to the upper and lower bands to provide appropriate tension that keeps the shaft at proper rigidity in both the articulated and straight configurations.

In one embodiment, the upper and lower band members may be attached to respective upper and lower sliders that may move axially for adjusting the respective tensions in the upper and lower bands and the rigidity of the segmented cannula. In one embodiment, the movement of the upper and lower sliders may be synchronized by coupling the sliders with a yoke giving a center of rotation located halfway between the upper and lower articulation bands. In one embodiment, the yoke is driven by a cam member that rotates back and forth (e.g., 90 degrees rotation). In one embodiment, the cam has a spiral slot which engages with a feature on the yoke. When the cam member reaches its limits of travel, the slope of the spiral slot is sufficiently steep (i.e. <10 degrees) to prevent back drive, i.e. the addition of external loads to the distal end of the articulating cannula is unable to force the cam member to rotate.

In one embodiment, the tension forces on the two bands may be adjusted by adjusting the distance between the sliders and rotating yoke.

In one embodiment, the articulating segmented members have a pin-less design, which reduces the risk of foreign matter (e.g., a pin) from falling into the abdominal cavity due to pin failure.

In one embodiment, the segmented members preferably have a channel or conduit for the surgical fasteners and the flexible member to pass through for firing a surgical fastener.

In one embodiment, the adjacent links of the segmented members are adapted to pivot relative to each other for articulating the segmented member. In one embodiment, each link has interlocking structures (e.g., wings) that maintain the rigidity and solid state of the segmented members when in the articulated or straight positions. In one embodiment, the interlocking structures fully restrict five degrees of freedom and only allow a limited range of rotation around one axis. In one embodiment, the links of the segmented members have pass ways or slots for receiving the upper and lower articulation bands.

In one embodiment, the distal ends of the upper and lower articulations bands are welded, joined, attached, hooked, crimped, or pinned onto a distal-most member of the series of segmented members.

In one embodiment, springs may be added to the tensioning adjustment means for tension force relief in the event excessive force is accidentally applied to the distal end of the articulating cannula. As such, less force would be required to displace the distal end of the articulating cannula assembly, resulting in less stress on the articulation bands.

In one embodiment, providing an applicator instrument having an articulating shaft provides many benefits. In one embodiment, providing an articulating shaft improves ergonomics during hernia surgery, enables ipsillateral (same side) mesh manipulation and fixation (reducing the required number of trocars), enhances maneuverability both inside and outside the body cavity, improves visualization of the fixation site, and reduces the length of surgical procedures.

In one embodiment, the articulation system requires only a one quarter turn (¼) of the cam or articulation lever(s) for fully articulating the shaft, and only a one quarter return to return the shaft to a straight position/configuration.

In one embodiment, the articulation system provides a high degree of tension and rigidity, prevents cannula deformation during application, and prevents cannula angle change when the shaft is in the articulated position to provide for tip stability and accurate placement for the fixation of surgical fasteners.

These and other preferred embodiments of the present patent application will be described in more detail herein.

BRIEF DESCRIPTION OF THE DRAWING

FIGS. 6B and 6B-1 show perspective views of the handle reconfiguration actuator and the slider of FIG. 6A with the handle reconfiguration actuator depressed for changing the position of the reconfigurable handle relative to the housing.

FIGS. 14A and 14A-1 show a magnified view of the firing system shown in FIG. 13B.

FIGS. 14B and 14B-1 show the firing system of FIGS. 14A and 14A-1 during later stages of the firing cycle after a surgical fastener has been stripped from a cartridge.

FIGS. 26A-26B, 26B-1, and 26C show a cartridge system of an applicator instrument having a racetrack element, in accordance with one embodiment of the present patent application.

DETAILED DESCRIPTION OF PREFERRED EMBODIMENTS

Figure 1A:
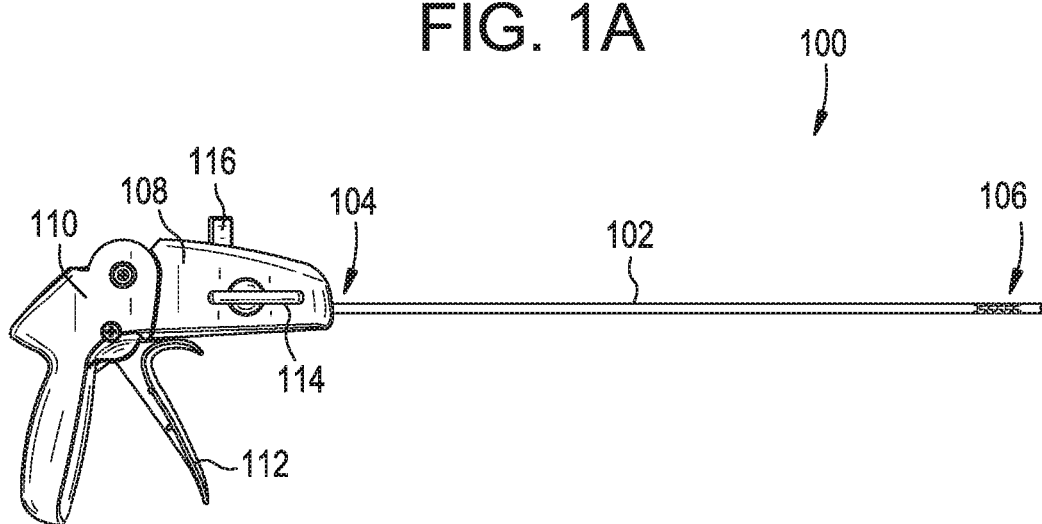
FIG. 1A shows an applicator instrument for dispensing surgical fasteners having an elongated shaft, a housing connected to a proximal end of the elongated shaft, and a reconfigurable handle pivotally connected with the housing, the reconfigurable handle being in a pistol configuration, in accordance with one embodiment of the present patent application.

Referring to FIG. 1A, in one embodiment, an applicator instrument 100 for dispensing surgical fasteners preferably includes an elongated shaft 102 having a proximal end 104 and a distal end 106. In one embodiment, surgical fasteners are advanced from the proximal end 104 to the distal end 106 of the elongated shaft 102 for dispensing the surgical fasteners one at a time from the distal end 106 of the shaft. In one embodiment, the distal end 106 of the elongated shaft 102 is capable of being articulated, as will be described in more detail herein.

In one embodiment, the applicator instrument 100 includes a housing 108 and a reconfigurable handle 110 that is coupled with a proximal end of the housing 108. The applicator instrument 100 includes a trigger 112 that may be squeezed toward the reconfigurable handle 110 for dispensing a surgical fastener from the distal end 106 of the elongated shaft 102.

In one embodiment, the applicator instrument 100 includes an articulation lever 114 that is accessible on the housing 108. The articulation lever 114 is desirably movable between a first position whereby the distal end 106 of the elongated shaft 102 is in a straight configuration, and a second position whereby the distal end 106 of the elongated shaft 102 is in an articulated configuration. The articulation lever 114 may be horizontal in the first position and vertical in the second position to provide a visual indicator as to whether the distal end of the elongated shaft is straight or articulated.

In one embodiment, the housing 108 of the applicator instrument 100 is adapted to receive a cartridge 116 that contains a plurality of surgical fasteners. In one embodiment, the surgical fasteners within the cartridge 116 are stacked atop one another and the cartridge is spring-loaded for urging the stacked surgical fasteners to move toward one end of the cartridge (e.g., in a downward direction). As will be described in more detail herein, the applicator instrument 100 preferably includes a flexible member that strips a single surgical fastener located at a lower end of a stack of surgical fasteners and pushes the surgical fastener through the elongated shaft 102 for being dispensed from the distal end 106 of the elongated shaft. In one embodiment, the flexible member serves as a structure for firing or dispensing a surgical fastener from a distal end of the elongated shaft.

Figure 1B:
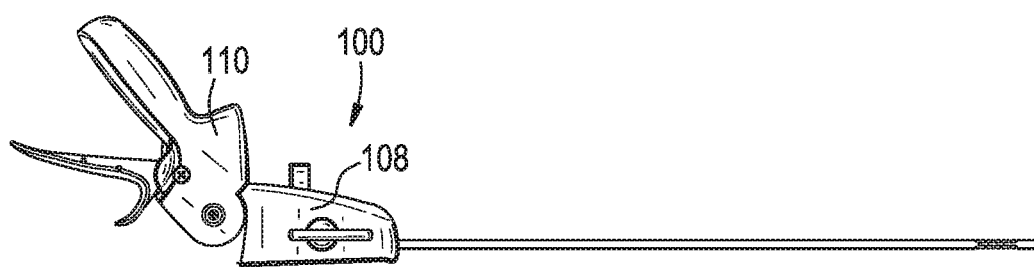
FIG. 1B shows the applicator instrument of FIG. 1A with the reconfigurable handle where the trigger is in a position in-line with the elongated shaft.

In one embodiment, the applicator instrument 100 may be placed in either a pistol configuration or an in-line configuration, or at a plurality of positions located between the pistol and in-line configurations. FIG. 1A shows the applicator instrument 100 with the handle 110 in a pistol configuration. Referring to FIG. 1B, in one embodiment, the handle 110 may be selectively rotated relative to the housing 108 for placing the handle in an in-line configuration. The ability to move the handle between a pistol configuration, an in-line configuration, and any intermediate positions/angles between the pistol and in-line configurations may be particularly useful during various types of surgical procedures (e.g., hernia repair procedures) where ergonomics and instrument maneuverability are critical. In one embodiment, the handle 110 may be locked at a range of different angular orientations relative to the housing 108. In one embodiment, the handle may be rotated beyond the pistol or in-line configurations. In one embodiment, as the position of the handle is being reconfigured, a gear train in the handle 110 is preferably disengaged from a firing system in the housing so that reconfiguring the handle does not affect the trigger, the gear train, or the firing system.

Figure 2A:
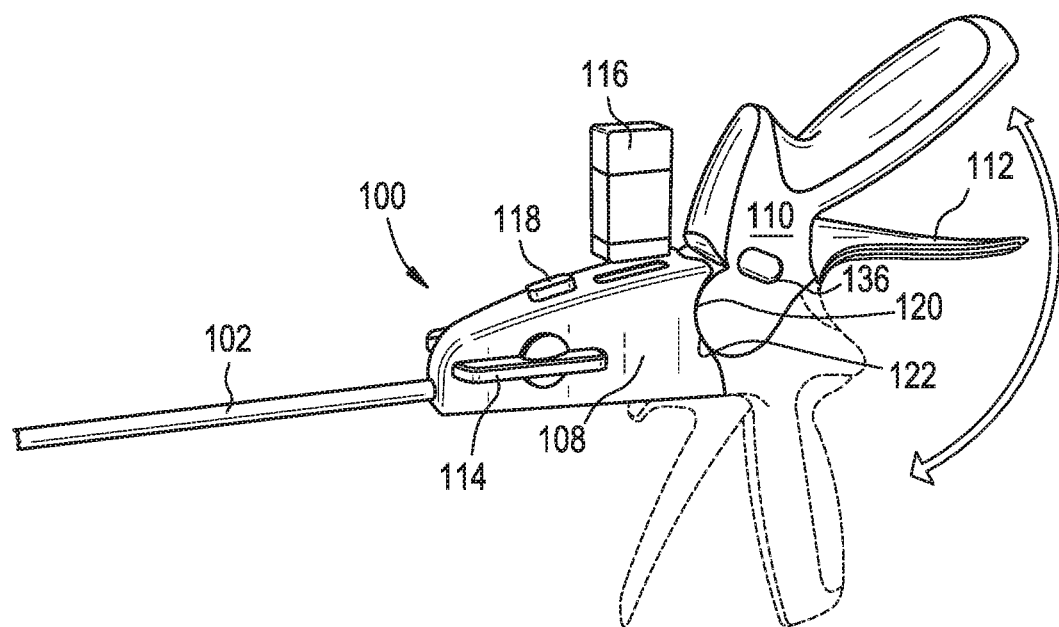
FIG. 2A shows a range of motion for the reconfigurable handle between the pistol configuration of FIG. 1A and the in-line configuration of FIG. 1B.

Referring to FIG. 2A, in one embodiment, the handle 110 of the applicator instrument 100 is reconfigurable so that it may be positioned in either the pistol configuration or an in-line configuration. In one embodiment, the handle 110 may also be positioned at intermediate locations between the pistol configuration and the in-line configuration. In one embodiment, the trigger 112 is coupled to the handle 110 and moves with the handle as it rotates relative to the housing 108 between the pistol configuration and the in-line configuration.

In one embodiment, the lower end of the cartridge 116 that contains a stack of surgical fasteners is inserted into an opening in the housing 108. In one embodiment, the lower end of the cartridge 116 forms a snap-fit connection with the housing 108. In one embodiment, a cartridge release button 118 may be depressed for removing the cartridge 116 from its snap-fit connection with the housing 108. The cartridge release button 118 may be on either the cartridge 116 or the housing 108. In one embodiment, an applicator instrument does not have a cartridge release button on the housing and a release element is provided on the cartridge that is inserted into the housing 108. In one embodiment, a proximal end 120 of the housing 108 has a concave surface and a distal end 122 of the handle 110 has a convex surface that guides movement of the handle 110 relative to the housing 108 as it rotates between the in-line and the pistol configuration.

Figure 2B:
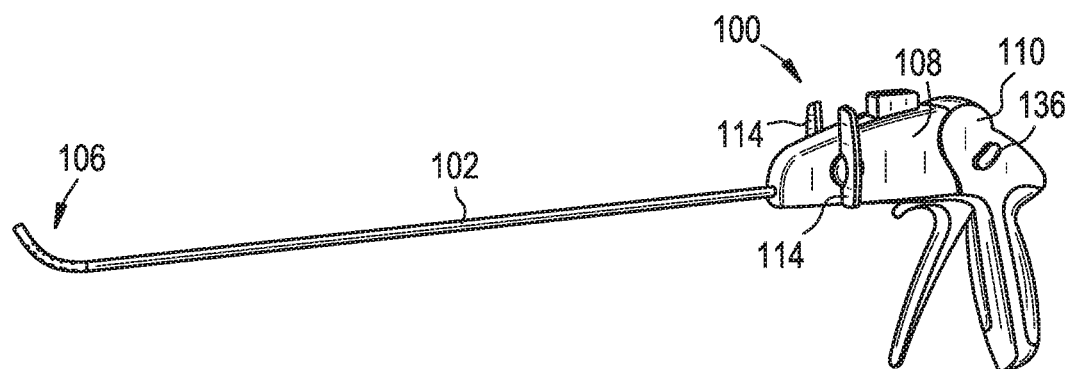
FIG. 2B shows the applicator instrument of FIG. 2A with the reconfigurable handle in the pistol configuration and the distal end of the elongated shaft in an articulated configuration.

Referring to FIGS. 2A and 2B, in one embodiment, the applicator instrument 100 preferably includes the elongated shaft 102 that projects from a distal end of the housing 108. The articulation lever 114 may be rotated from the first position (i.e., horizontal) shown in FIG. 2A, whereby the distal end of the elongated shaft is straight, and the second position (i.e., vertical) FIG. 2B whereby the distal end 106 of the elongated shaft 102 is in an articulated configuration. In one embodiment, the distal end 106 of the elongated shaft 102 may be moved between the straight configuration and the articulated configuration with the handle 110 in either the in-line configuration (FIG. 2A) or the pistol configuration (FIG. 2B). A reconfiguration button 136 may be engaged for moving the handle 110 between the pistol and in-line configurations. The position of the handle may be locked in place by releasing the reconfiguration button 136.

Figure 3:
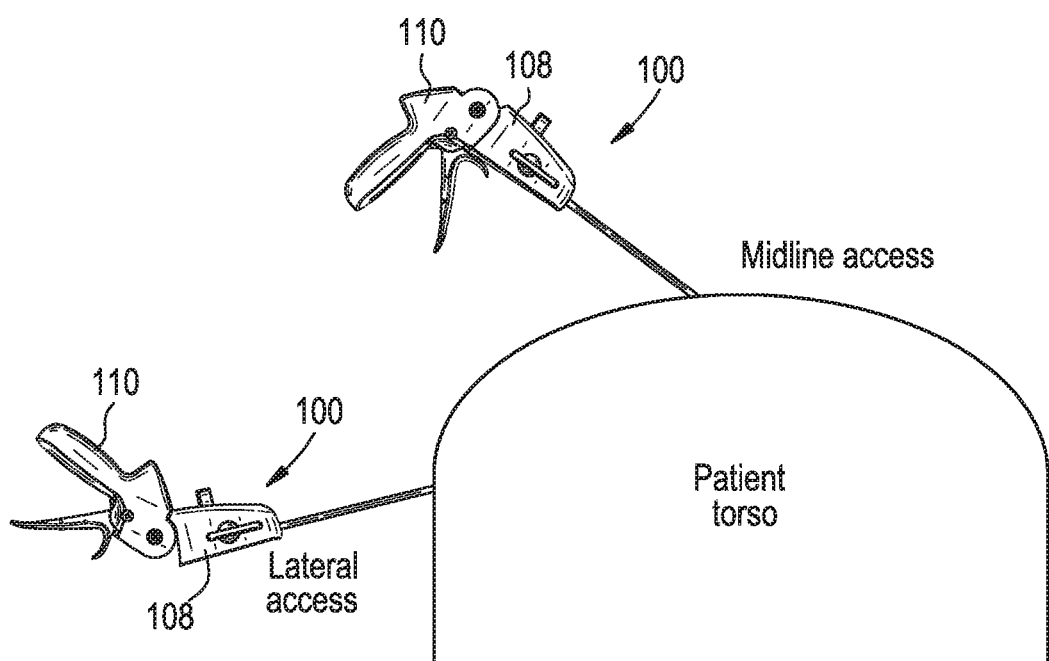
FIG. 3 shows the applicator instrument of FIGS. 1A and 1B used for lateral access and midline access on a patient, in accordance with one embodiment of the present patent application. Lateral access is typical for a ventral or TAPP inguinal repair. Midline access is typical for a TEP inguinal repair.

Referring to FIG. 3, in one embodiment, the position of the handle 110 relative to the housing 108 may be selectively reconfigured for improving ergonomics and instrument maneuverability during a surgical procedure. In one embodiment, when the applicator instrument 100 is used for transabdominal pre-peritoneal (TAAP) inguinal and ventral repairs, a lateral access approach into the patient may be utilized. For lateral access, in order to improve ergonomics and instrument maneuverability, the handle 110 may be placed in the in-line configuration relative to the housing 108. Depending on the location of the target fixation site relative to the trocar, other handle positions may be used, as necessary. In contrast, for totally extra-peritoneal (TEP) inguinal repairs, where trocars are placed near the patient's mid-line, the handle 110 of the applicator instrument 100 may be placed in the pistol configuration relative to the housing 108 for improving ergonomics and instrument maneuverability. Depending on the location of the target fixation site relative to the trocar, other handle positions may be used, as necessary. Although the present invention is not limited by any particular theory of operation, it is believed that providing applicator instruments for dispensing surgical fasteners that have reconfigurable handles, with one or more positions between the pistol and in-line configurations, dramatically improves the maneuverability and ergonomics of the applicator instruments when used during laparoscopic procedures. Of particular benefit is the ability to achieve a neutral wrist angle for the surgeon. Reconfigurable handles also enable more accurate placement of surgical fasteners, reduced fatigue, and enhanced accuracy when affixing surgical fasteners. Moreover, reconfigurable handles enable a surgeon to maintain the entire applicator instrument within a sterile field so that a surgeon may avoid moving any portion of the applicator instrument outside the sterile field as the surgeon maneuvers the applicator instrument into different orientations.

Figure 4A:
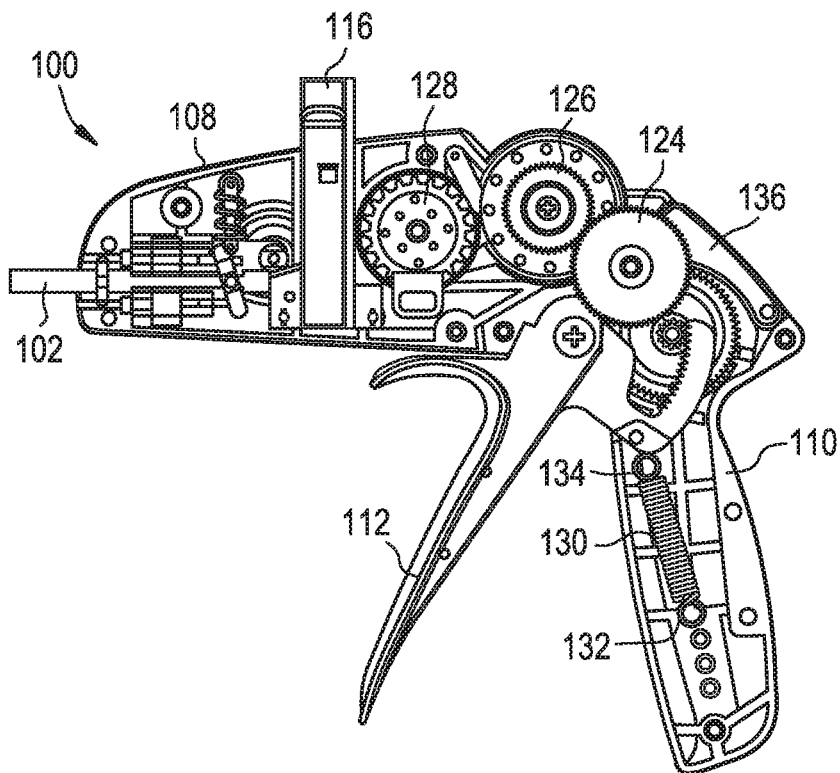
FIG. 4A shows a cross-sectional view of the applicator instrument of FIGS. 1A and 1B with the reconfigurable handle in the pistol configuration.

Referring to FIG. 4A, in one embodiment, the applicator instrument 100 preferably includes the housing 108 and the reconfigurable handle 110 coupled with a proximal end of the housing. The applicator instrument 100 includes the elongated shaft 102 that extends distally from a distal end of the housing 108. In one embodiment, the applicator instrument includes a gear train 124 that extends between the trigger 112 in the handle 110 and the housing 108 for activating a firing system to dispense a surgical fastener. In one embodiment, the applicator instrument has a firing system that meshes with the gear train 124. In one embodiment, the firing system preferably includes a storage reel 126 for storing a flexible member used to dispense a surgical fastener from a distal end of the elongated shaft 102, a drive wheel 128 that engages the flexible member for driving the flexible member toward the distal end of the elongated shaft 102 for dispensing a surgical fastener, and a constant torque spring for storing energy used to drive the drive wheel 128.

In one embodiment the housing 108 has an opening adapted to receive a cartridge 116 containing a plurality of surgical fasteners stacked in the cartridge. The surgical fasteners within the cartridge 116 are adapted to be dispensed one at a time from the distal end of the elongated shaft 102. During a firing cycle, each time the trigger 112 is squeezed toward the handle 110, a firing cycle commences for firing a single surgical fastener from the distal end of the elongated shaft 102. In one embodiment, the applicator instrument 100 includes a trigger return spring 130 having a lower end 132 connected with the handle 110 and an upper end 134 connected with the trigger 112. In one embodiment, the trigger return spring 130 normally urges the trigger to return to the open position shown in FIG. 4A.

In one embodiment, an applicator instrument may be capable of receiving different cartridges containing surgical fasteners having different properties. In one embodiment, the different properties for the surgical fasteners may relate to the material, absorption time, size, length, width, leg length, barb length, number of barbs on a leg, curved legs, straight legs, color, opacity, cartridge quantity, etc. In one embodiment, a first cartridge may contain surgical fasteners having a first property (e.g., legs having a first length) and a second cartridge may contain surgical fasteners having a second property (e.g., legs having a longer second length) that is different than the first property. The first cartridge may be inserted into the applicator instrument for dispensing the first surgical fasteners into the patient. After completing the fixation necessary with the first surgical fasteners, the first cartridge may be decoupled from the applicator instrument and replaced by the second cartridge for dispensing the second surgical fasteners into the patient. A portion of the applicator instrument (e.g., the elongated shaft), may remain inside the patient as the cartridges are changed, which preferably minimizes the time required to perform a surgical procedure and enhances sterile conditions. After exchanging cartridges, the applicator device is immediately ready to use the second set of surgical fasteners. Additional cartridges having additional properties may be used during a single surgical procedure. In one embodiment, multiple surgical fastener types may be provided in a single cartridge.

Figure 4B:
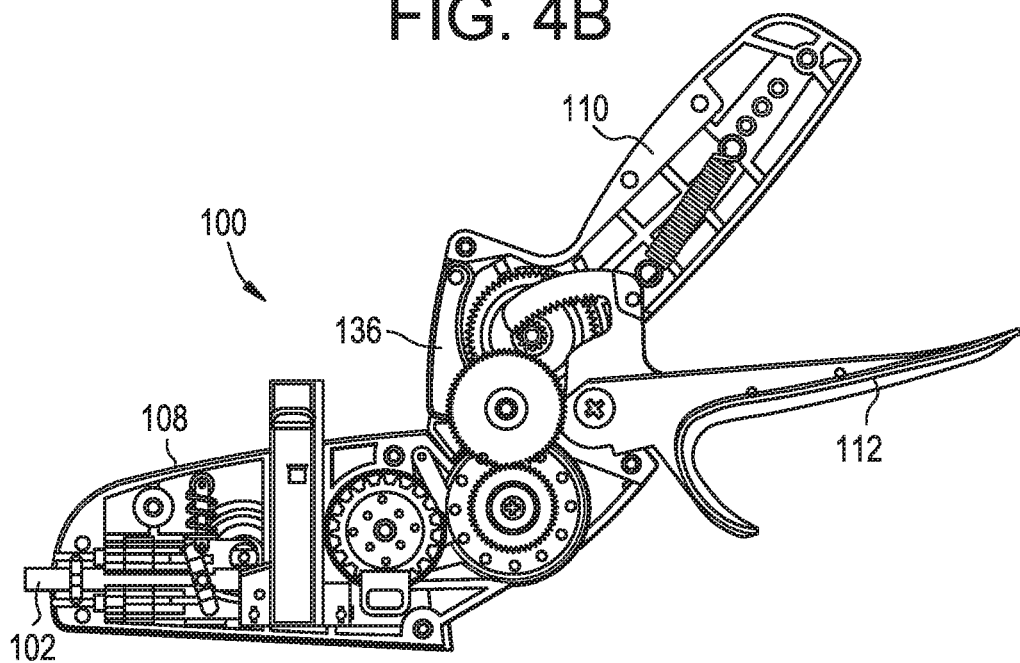
FIG. 4B shows a cross-sectional view of the applicator instrument of FIGS. 1A and 1B with the reconfigurable handle in the in-line configuration.

In one embodiment, the applicator instrument 100 preferably includes a handle reconfiguration actuator 136 (e.g., a depressible button) that is provided on the reconfigurable handle 110. In FIG. 4A, the handle reconfiguration actuator 136 is depressed so that the handle 110 may be rotated between the pistol configuration shown in FIG. 4A and the in-line configuration shown in FIG. 4B. Referring to FIGS. 4A and 4B, in one embodiment, the trigger 112 is coupled with the reconfigurable handle 110 so that the trigger rotates with the handle as it moves between the pistol configuration and the in-line configuration.

In one embodiment, the handle 110 may be rotated relative to the housing 108 when the handle reconfiguration actuator 136 is depressed or moved. When the handle reconfiguration actuator 136 is not depressed, the handle 110 is locked in place relative to the housing 108 and may not move between the pistol and in-line configurations. In one embodiment, the gear train extends between the handle and the housing in order to actuate the firing system. The handle includes the trigger 112 for activating the gear train 124. When the trigger is pulled, the gear train 124 is activated for commencing a firing cycle and allowing a surgical fastener to be dispensed from a distal end of the elongated shaft 102. In one embodiment, the gear train 124 is initially disengaged when the trigger 112 is open. In one embodiment, when the trigger 112 is actuated (e.g., squeezed), the gear train 124 engages the firing system. Because the gear train 124 is initially disengaged, the handle 110 can be reconfigured between the pistol configuration and the in-line configuration without affecting the stroke of the trigger/gear train. In one embodiment, a one-way bearing meshes the gear train with the firing system during a first stage of a firing cycle, and the one-way bearing decouples the gear train from the firing system during a later stage of the firing cycle. In another embodiment, when the handle reconfiguration actuator 136 is depressed for rotating the handle 110, a portion of the gear train located in the handle 110 is disengaged, allowing for the reconfiguration of the handle relative to the housing and not affecting the stroke of the trigger/gear train. In one embodiment, when the trigger 112 is squeezed for activating a firing cycle, the handle reconfiguration actuator 136 is blocked from being depressed so as to prevent reconfiguration of the handle relative to the housing during a firing cycle. In one embodiment, when the handle reconfiguration actuator 136 is depressed, the trigger and/or gear train 124 is blocked to prevent firing of a surgical fastener prior to completing the reconfiguration of the handle relative to the housing.

Figure 5:
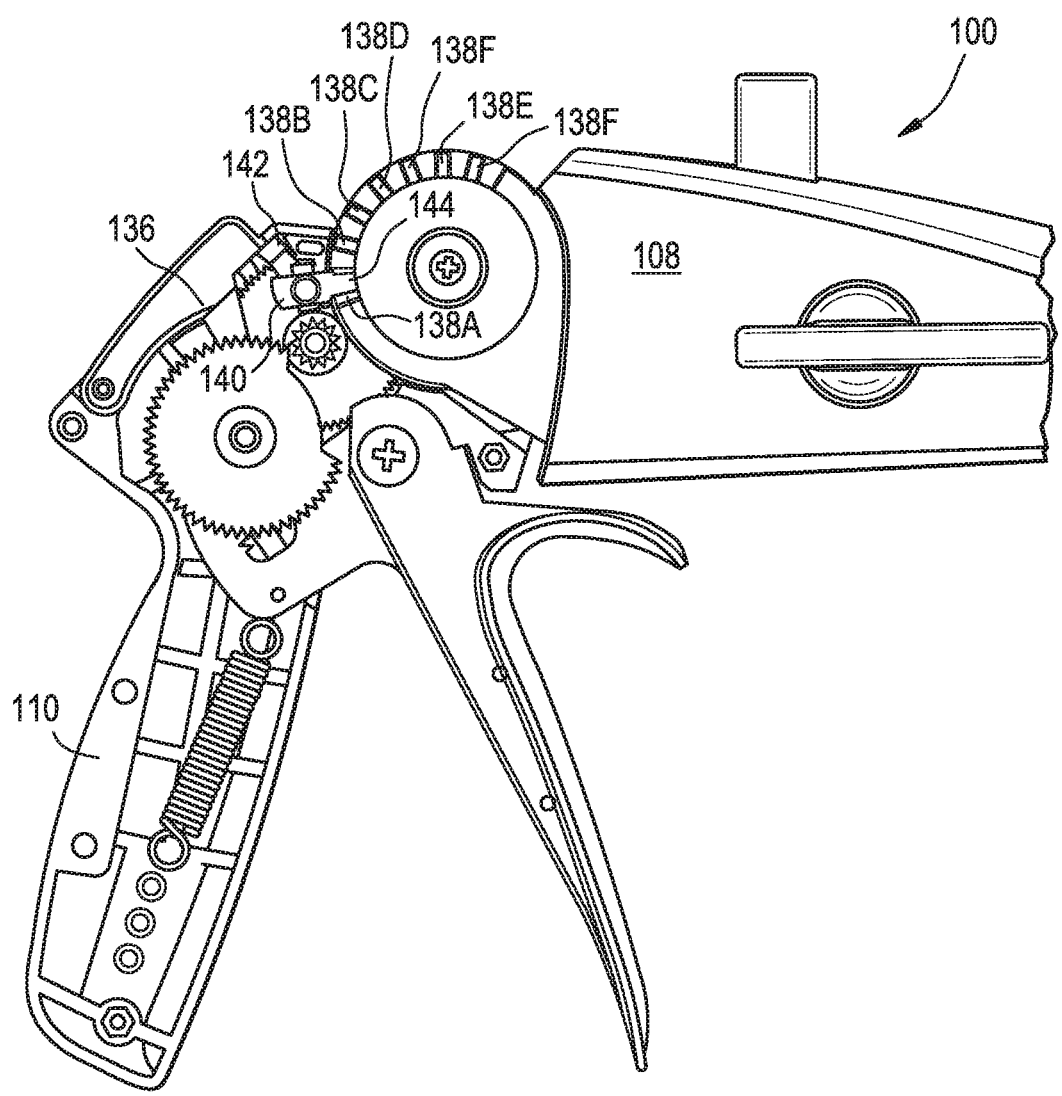
FIG. 5 shows the reconfiguration mechanism and pivotal connection between housing and a reconfigurable handle of an applicator instrument, in accordance with one embodiment of the present patent application.

Referring to FIG. 5, in one embodiment, a proximal end of the housing 108 includes a series of spaced reconfiguration notches 138A-138G that are utilized for positioning the handle 110 at different configurations/angles relative to the housing 108. In one embodiment, the reconfiguration notches 138A-138G are arrayed in an arc-shaped pattern at the proximal end of the housing 108. In one embodiment, the applicator instrument 100 includes a slider 140 that extends between the handle reconfiguration actuator 136 and the reconfiguration notches 138A-138G at the proximal end of the housing 108. The slider 108 includes a proximal end 142 that is engaged by an underside of the handle reconfiguration actuator 136 and a distal end 144 that is adapted to be seated within the reconfiguration notches 138A-138G. In one embodiment, when the handle reconfiguration actuator 136 is depressed, the distal end 144 of the slider 140 disengages from one of the reconfiguration notches 138A-138G, which enables the handle 110 to be rotated relative to the housing 108. When the handle reconfiguration actuator 136 is released, the distal end 144 of the slider 140 is seated within one of the reconfiguration notches 138A-138G for locking the position of the handle 110 relative to the housing 108 so that the handle may not be pivoted relative to the housing.

Figure 6A:
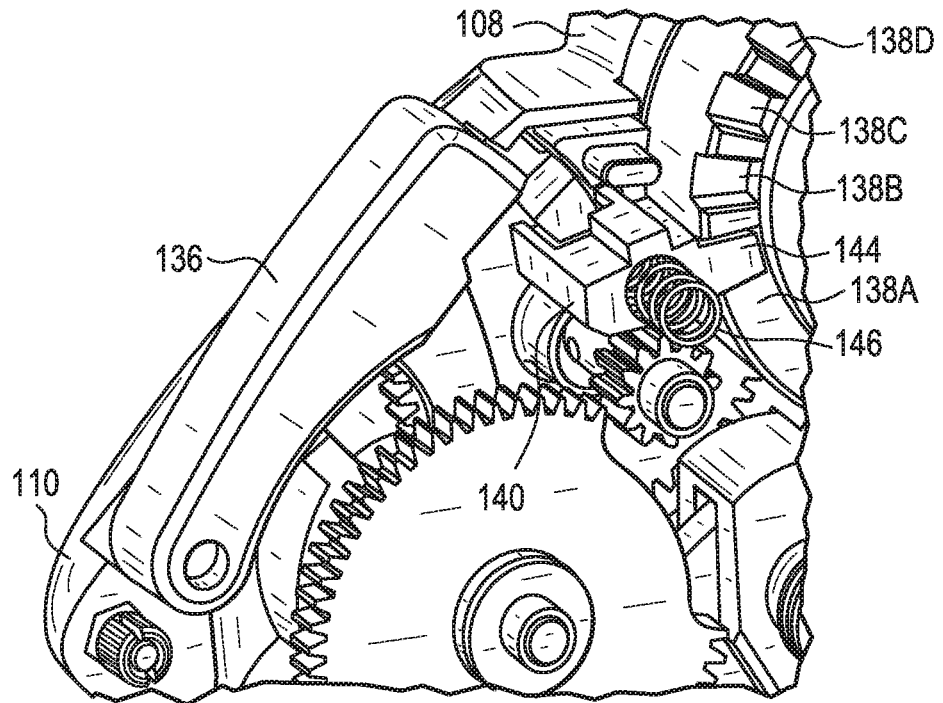
FIGS. 6A and 6A-1 show perspective views of a handle reconfiguration actuator and a slider used for changing the position of a reconfigurable handle relative to a housing, in accordance with one embodiment of the present patent application.
Figures 1, 6A:
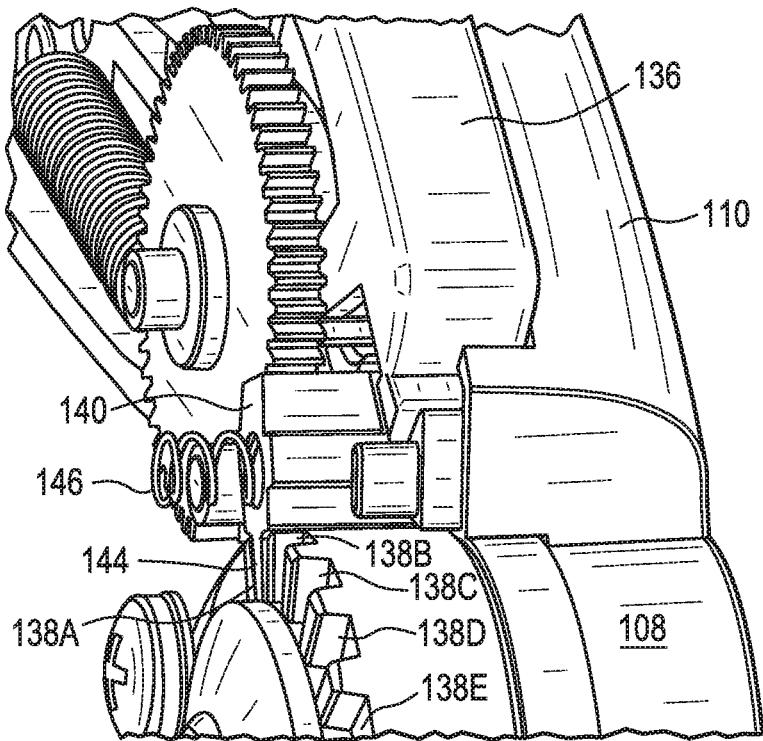

Referring to FIGS. 6A and 6A-1, in one embodiment, when the handle reconfiguration actuator 136 is in an extended, undepressed position, the distal end 144 of the slider 140 sits within the reconfiguration notch 138A for locking the position of the handle 110 relative to the housing 108. A slider return spring 146 normally urges the distal end 144 of the slider 140 to be seated within one of the reconfiguration notches 138A-138G (FIG. 5).

Figure 6B:
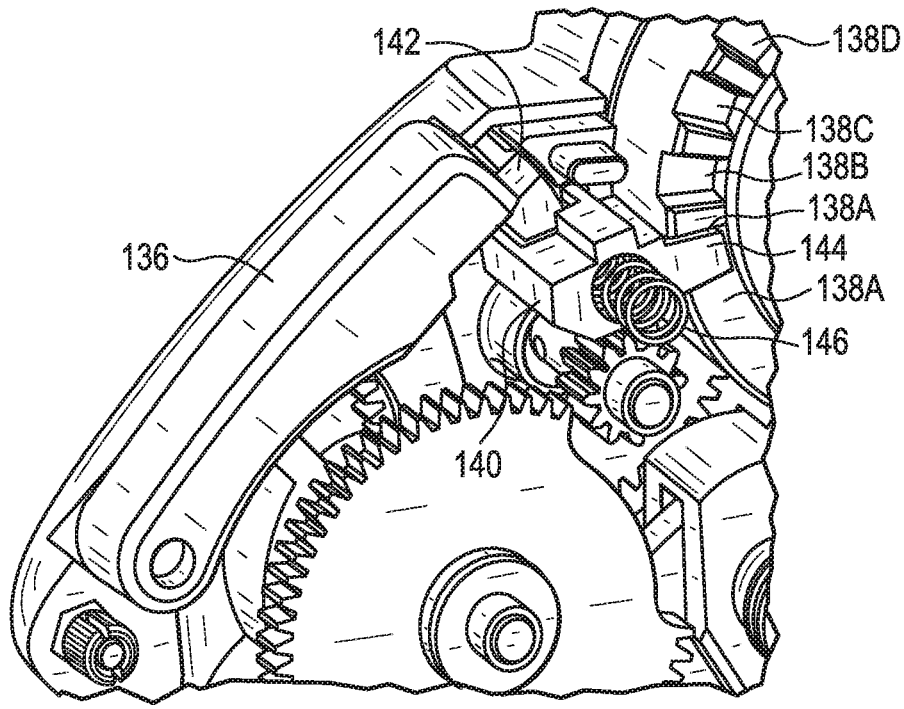
Figures 1, 6B:
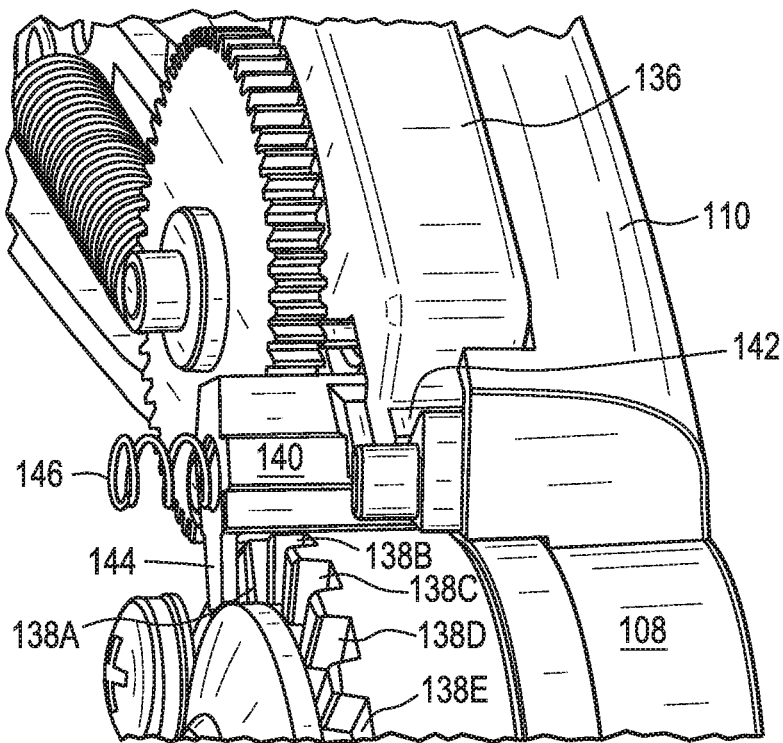

Referring to FIGS. 6B and 6B-1, when the handle reconfiguration actuator 136 is depressed, and underside of the handle reconfiguration actuator engages the proximal end 142 of the slider 140 for overcoming the force of slider return spring 146 and shifting the distal end 144 of the slider 140 away from the reconfiguration notch 138A. As the distal end 144 of the slider 140 moves away from the reconfiguration notch 138A, the slider return spring 146 is compressed. With the handle reconfiguration actuator 136 depressed, the handle 110 may be rotated relative to the housing 108 for aligning the distal end 144 of the slider 140 with any one of the other reconfiguration notches 138A-138G (FIG. 5). When the handle 110 has been positioned at a desired configuration relative to the housing 108, the handle reconfiguration actuator 136 may be released, whereupon the slider return spring 146 urges the slider 140 and the distal end 144 of the slider 140 back into engagement with one of the reconfiguration notches 138A-138G on the housing 108 for locking the handle in place. The handle 110 is locked in place relative to the housing 108 as long as the distal end 144 of the slider 140 is seated in one of the reconfiguration notches 138A-138G (FIG. 5).

Figure 7:
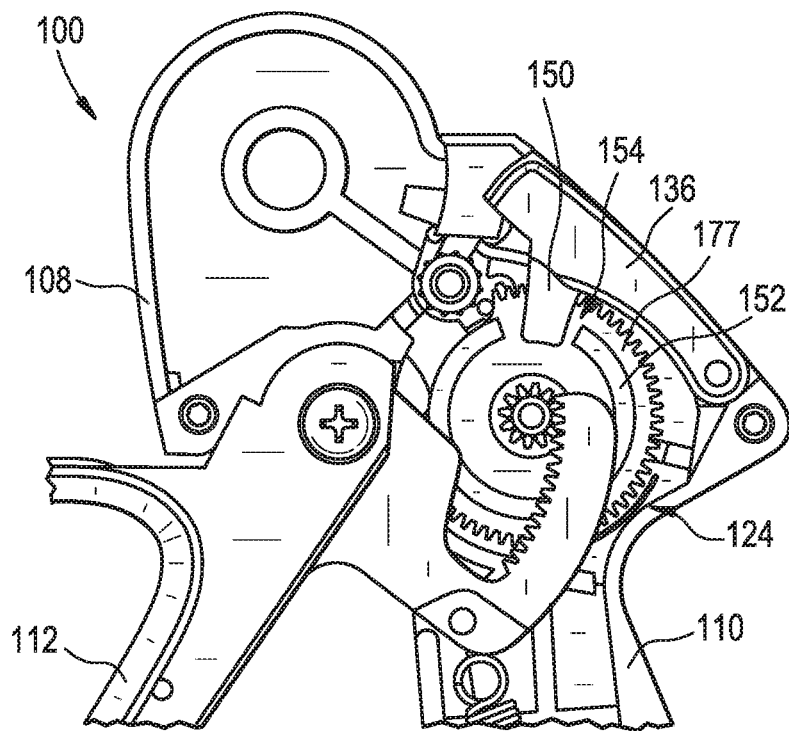
FIG. 7 shows a cross-sectional view of an applicator instrument including a positive stop provided on a gear for preventing squeezing of a trigger when a handle reconfiguration actuator is depressed, in accordance with one embodiment of the present patent application.

Referring to FIG. 7, in one embodiment, the handle reconfiguration actuator 136 has a locking projection 150 that extends from an underside thereof. In one embodiment, the gear train 124 preferably has a drive gear 177 having a raised ring 152 that projects above a major face of the drive gear. The raised ring 152 on the drive gear 177 is not continuous and includes a ring opening 154 that is normally aligned with the locking projection 150 of the handle reconfiguration actuator 136 when the trigger 112 is in an extended/open position. In one embodiment, when the handle reconfiguration actuator 136 is depressed for changing the configuration of the handle 110 relative to the housing 108, the locking projection 150 extends into the ring opening 154 of the raised ring 152 of the drive gear 177, which blocks the trigger 112 from being pulled toward the handle 110. Thus, the firing system including the gear train 124 of the applicator instrument may not be activated when the handle reconfiguration actuator 136 is depressed for reconfiguring the position of the handle 110 relative to the housing 108.

Figure 8:
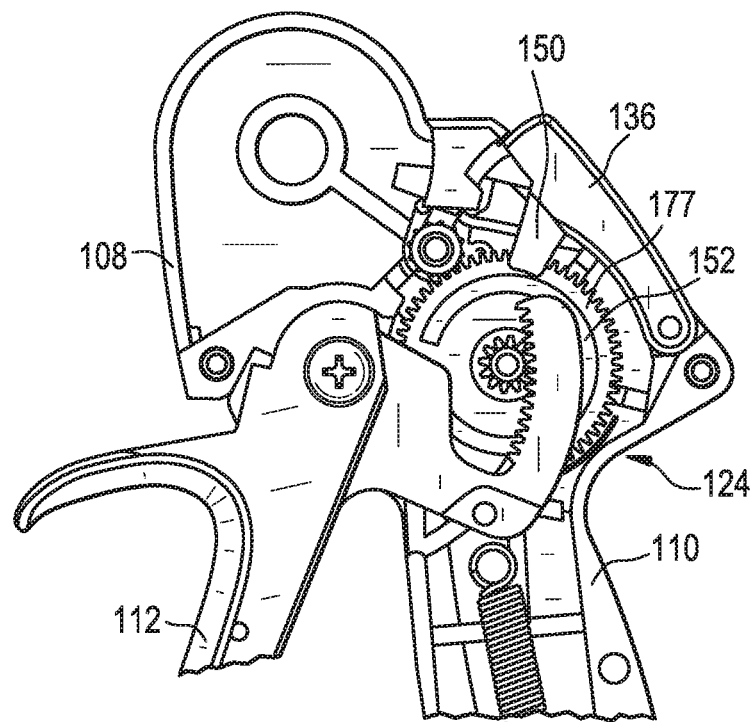
FIG. 8 shows a cross-sectional view of an applicator instrument including a positive stop provided on a gear for preventing the handle reconfiguration actuator from being depressed after the trigger has been squeezed for commencing a firing cycle.

Referring to FIG. 8, in one embodiment, when the trigger 112 is squeezed toward the handle 110 for commencing a firing cycle, the handle reconfiguration actuator 136 may not be depressed for reconfiguring the position of the handle 110 relative to the housing 108. In one embodiment, the drive gear 177 includes the raised ring 152 projecting from a major face thereof. As the trigger 112 is pulled toward the handle 110, the drive gear 177 rotates in a counterclockwise direction so that the closed portion of the raised ring 152 is aligned with the locking projection 150 extending from an underside of the handle reconfiguration actuator 136. As a result, the handle reconfiguration actuator 136 is blocked from being depressed by the engagement of the locking projection 150 with the outer perimeter of the raised ring 152 of the drive gear 177.

Figure 9A:
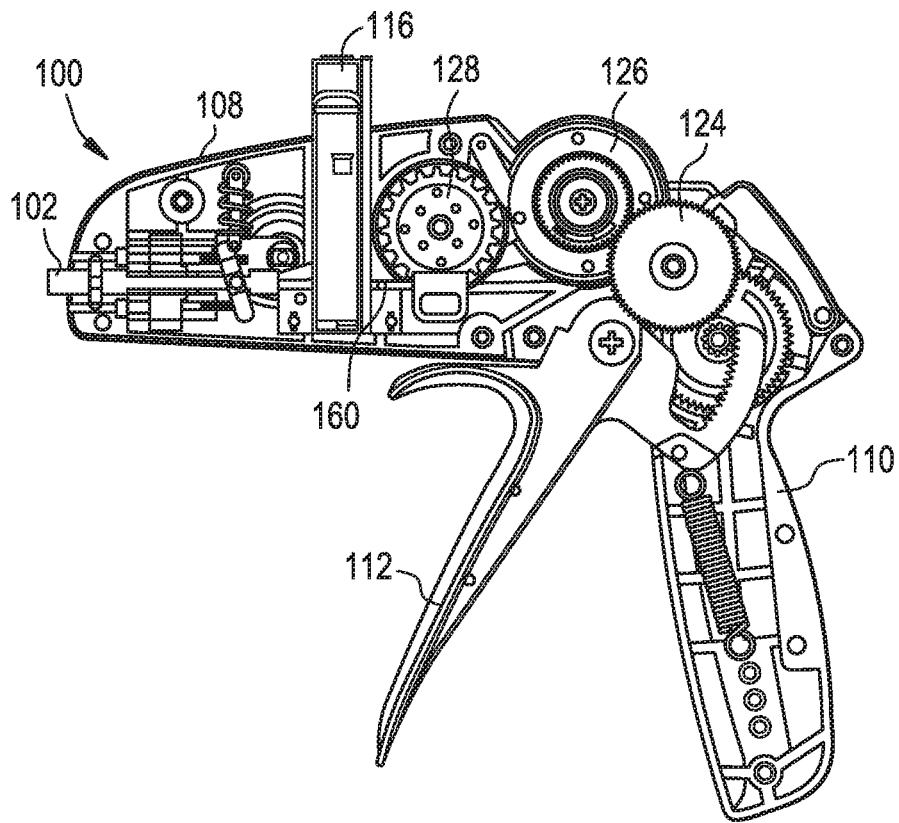
FIG. 9A shows a cross-sectional view of an applicator instrument for dispensing surgical fasteners, in accordance with one embodiment of the present patent application.
Figure 9B:
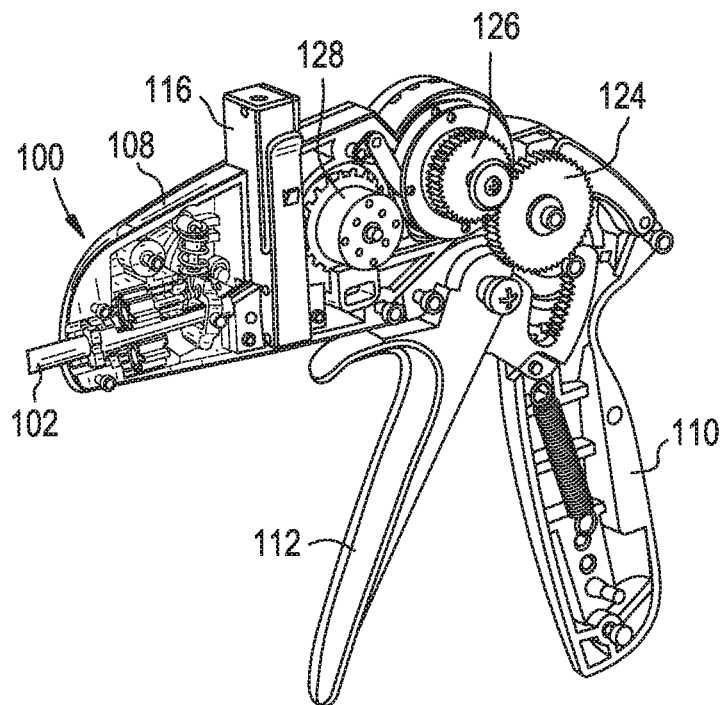
FIG. 9B shows a perspective view of the applicator instrument of FIG. 9A.

Referring to FIGS. 9A and 9B, in one embodiment, an applicator instrument 100 for dispensing surgical fasteners includes a housing 108 and a handle 110 that may be reconfigured relative to the housing 108 for moving the handle 110 between a pistol configuration and an in-line configuration. The applicator instrument 100 includes a firing system for dispensing a surgical fastener from a distal end of an elongated shaft 102 that projects from a distal end of the housing 108. In one embodiment, the firing system is activated by a trigger 112 that may be squeezed toward the handle 110. In one embodiment, the firing system includes a gear train 124 that extends between the trigger 112 and the housing 108. In one embodiment, portions of the gear train may be disposed within both the handle 110 and the housing 108. The firing system for the applicator instrument 100 desirably includes a storage reel 126 that is adapted to store a flexible member 160 and a drive wheel 128 that engages the flexible member 160 for driving the flexible member toward the distal end of the elongated shaft 102. The flexible member preferably engages surgical fasteners for dispensing the surgical fasteners from the distal end of the elongated shaft. A cartridge 116 containing a plurality of surgical fasteners may be inserted into an opening in the housing 108 to provide surgical fasteners for the firing system. In one embodiment, a plurality of surgical fasteners are arrayed in a stack within the cartridge 116 and a lower-most one of the surgical fasteners in the stack is dispensed from a distal end of the elongated shaft 102 each time the trigger 112 is squeezed for activating a firing cycle. A distal-most end of the flexible member is adapted to strip the lower-most surgical fastener from the stack of surgical fasteners within the cartridge 116 and advance the singulated surgical fastener toward the distal end of the elongated shaft 102 for dispensing the surgical fastener from the applicator instrument. In one embodiment, the storage reel 126 rotates in a counterclockwise direction for winding the flexible member 160 onto the storage reel. During the firing cycle, the storage reel 126 rotates in a clockwise direction as the flexible member is driven in a distal direction by the drive wheel 128, also rotating in a clockwise direction.

Figure 10A:
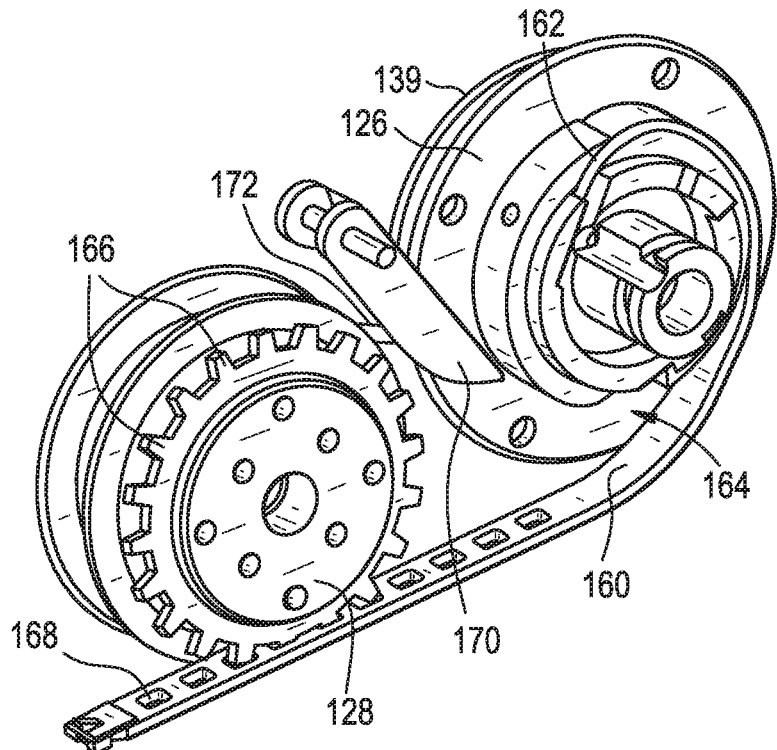
FIGS. 10A and 10B show a flexible member, a storage reel and a drive wheel of an applicator instrument for dispensing surgical fasteners, in accordance with one embodiment of the present patent application.
Figure 10B:
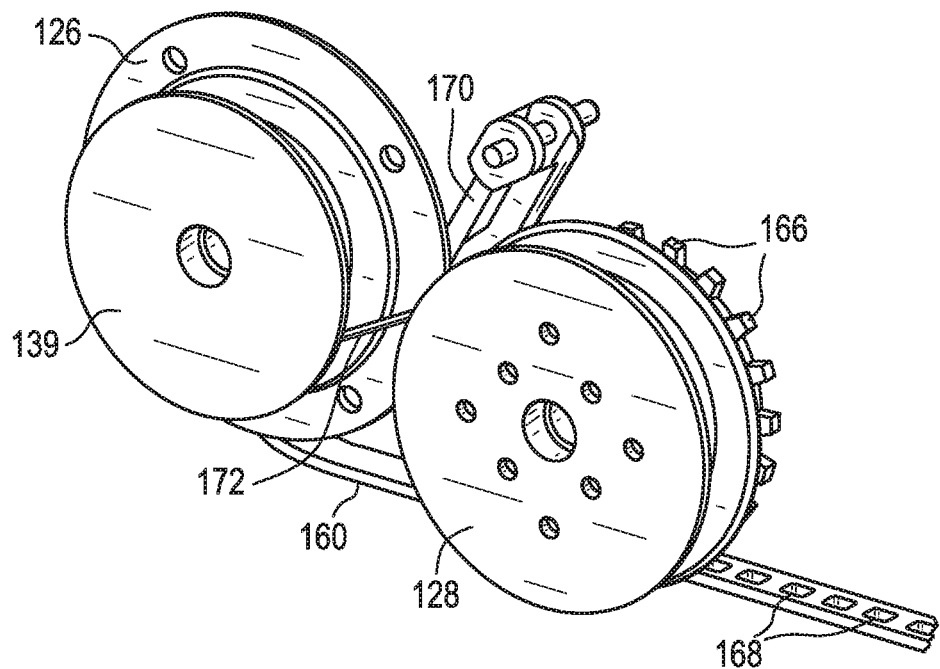

Referring to FIGS. 10A and 10B, in one embodiment, the flexible member 160 has a proximal end 162 that is attached to the storage reel 126. When the storage reel 126 rotates in a counterclockwise direction, the flexible member 160 is wound about the storage wheel. When the storage wheel 126 rotates in a clockwise direction, the flexible member 160 is unwound from the storage reel 126 so that it may be advanced toward the distal end of the elongated shaft. In one embodiment, the storage reel 126 has a notch 164 (FIG. 10A) formed in the outer perimeter thereof. In one embodiment, the notch 164 may be engaged by a pivoting stop 170 located in the housing for preventing further clockwise rotation of the storage reel.

In one embodiment, the drive wheel 128 has a plurality of gear teeth 166 that project from an outer perimeter thereof that engage a series of openings 168 formed in the flexible member 160. In one embodiment, when the drive wheel 128 rotates in a clockwise direction (from the perspective shown in FIG. 10A), the teeth 166 engage the openings 168 on the flexible member 160 for driving the flexible member towards the distal end of the elongated shaft. In one embodiment, a constant torque spring 172 is connected between a spool 139 and the drive wheel 128. In one embodiment, retraction of the flexible member 160 rotates the drive wheel 128 in a counterclockwise direction (from the perspective shown in FIG. 10A), which, in turn, winds the constant torque spring 172 from the spool 139 onto the drive wheel 128. This action stores potential energy as the constant torque spring 172 wants to return to the spool 139.

Figure 11:
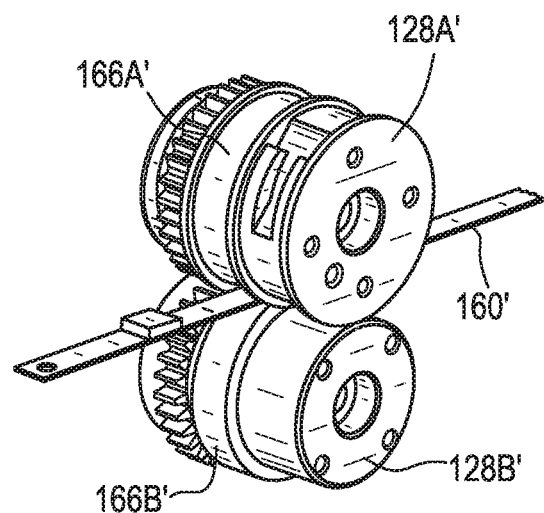
FIG. 11 shows a flexible member and friction drive wheels of an applicator instrument for dispensing surgical fasteners, in accordance with one embodiment of the present patent application.

Referring to FIG. 11, in one embodiment, rather than using the cogged drive wheel shown in FIG. 10, the firing system may include a pair of friction wheels 128A', 128B' having opposing friction surfaces 166A' that engage top and bottom surfaces of a flexible member 160' for driving the flexible member 160' toward a distal end of an elongated shaft. In one embodiment, the pair of friction wheels are geared to each other to reduce the potential for slippage.

Figure 12:
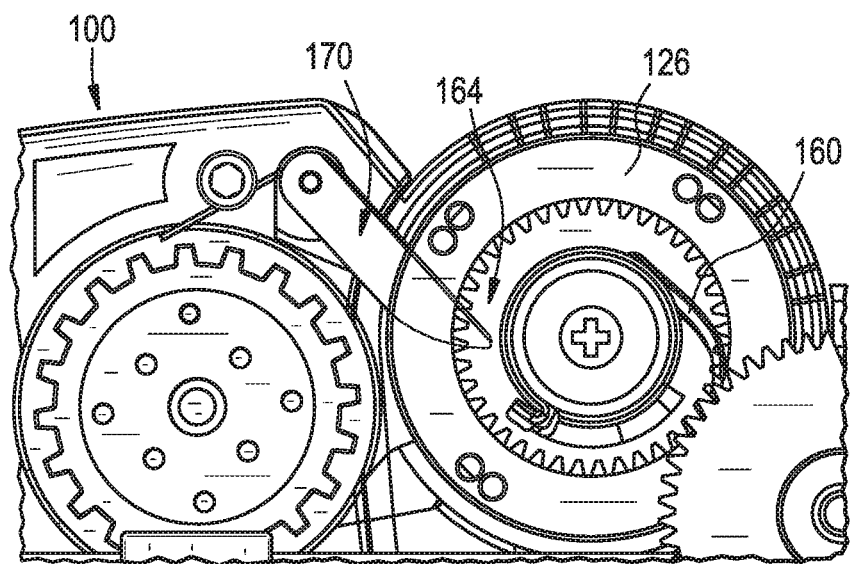
FIG. 12 shows a cross-sectional view of an applicator instrument for dispensing surgical fasteners including a storage reel, a drive wheel, and a proximal positive stop for halting rotation of the storage reel, in accordance with one embodiment of the present patent application.

Referring to FIG. 12, in one embodiment, the applicator instrument 100 includes the proximal, pivoting stop 170 adapted to engage the notch 164 formed on the outer perimeter of the storage reel 126. The proximal positive stop 170 engages the notch 164 for preventing further clockwise rotation of the storage reel 126 so as to halt further distal movement of the flexible member 160 (FIG. 10A) toward the distal end of the elongated shaft. In one embodiment, as the flexible member 160 is wound onto the storage reel 126, the proximal positive stop 170 is adapted to pivot away from the outer perimeter of the storage reel 126 when the storage reel is rotated in a counterclockwise direction, however, as the flexible member is driven toward the distal end of the elongated shaft, the proximal stop 170 is adapted to pivot into engagement with the notch 164 of the storage reel 126 for halting further clockwise rotation of the storage reel 126.

Figure 13A:
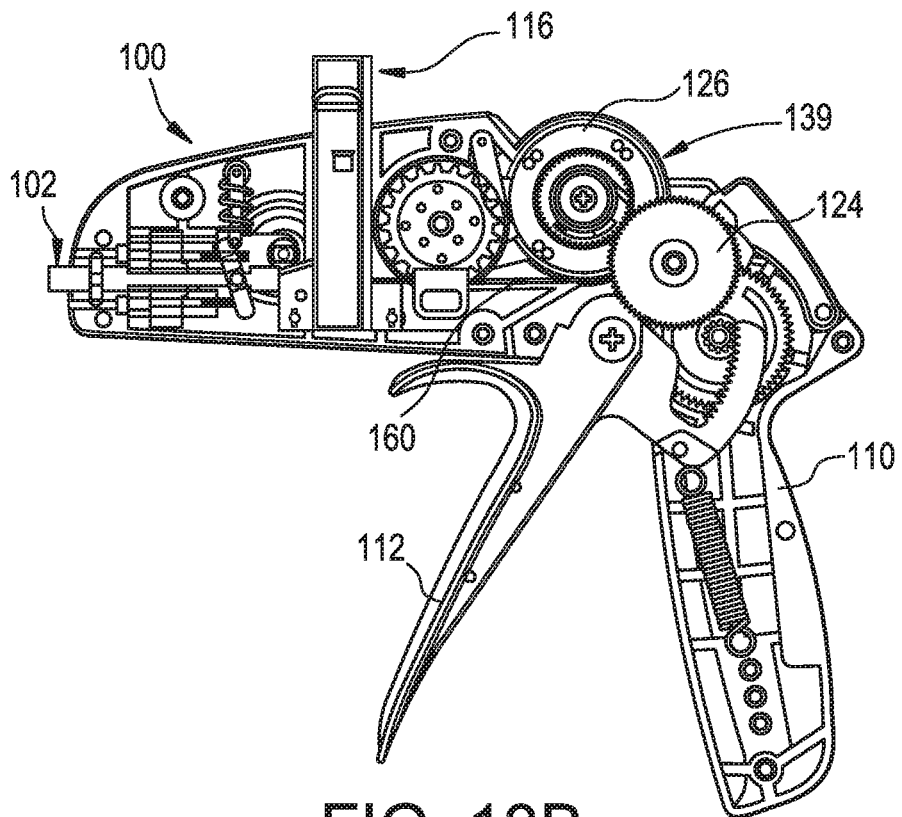
FIG. 13A shows a cross-sectional view of an applicator instrument for dispensing surgical fasteners prior to the commencement of a firing cycle, in accordance with one embodiment of the present patent application.

Referring to FIG. 13A, in one embodiment, at the commencement of a firing cycle, the trigger 112 is in an extended position, away from the handle 110. The flexible member 160 preferably extends to the distal end of the elongated shaft 102. Surgical fasteners (not shown) are desirably stacked within the cartridge 116, which, in turn, is inserted into the housing 108. The firing system includes a constant torque spring 172 (FIG. 10B) that is connected between a spool 139 (FIG. 10B) coupled with the storage reel 126 and the drive wheel 128.

Figure 13B:
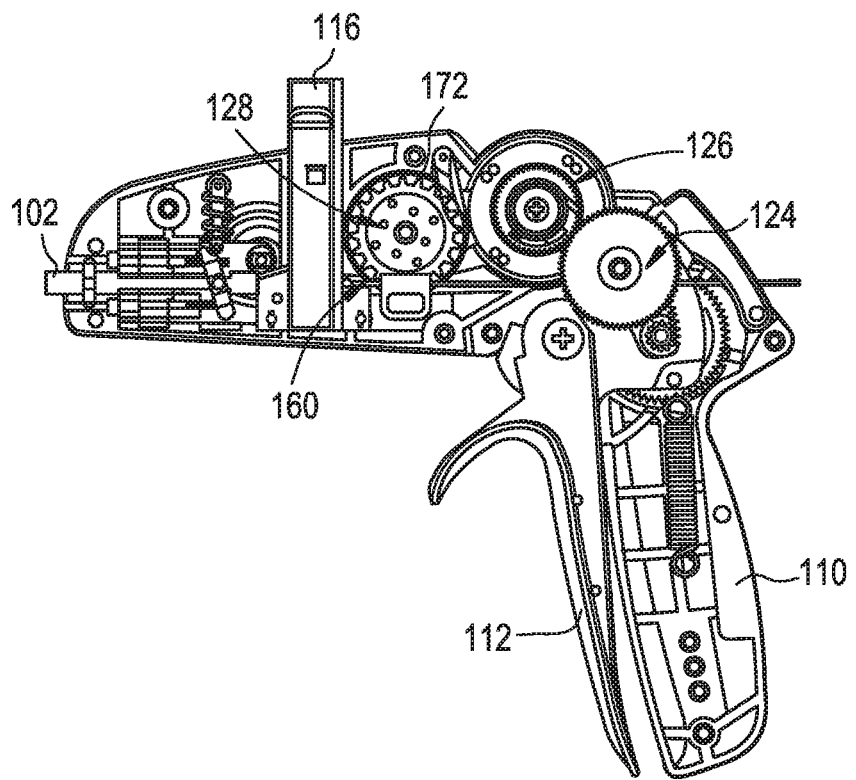
FIG. 13B shows a cross-sectional view of the applicator instrument of FIG. 13A during a later stage of the firing cycle, in accordance with one embodiment of the present patent application.

Referring to FIG. 13B, in one embodiment, as a user squeezes the trigger 112 toward the handle 110, the gear train 124 between the trigger 112 and the storage reel 126 re-meshes and begins rotating the storage reel 126 in a counterclockwise direction for retracting the distal end of the flexible member 160 from the distal end of the elongated shaft 102 and winding the flexible member 160 onto the storage reel 126 so that the distal end of the flexible member 160 is proximal to the cartridge 116 and the surgical fasteners stacked within the cartridge. Retraction of the flexible member 116 rotates the drive wheel 128 in a counterclockwise direction, which, in turn, winds the constant torque spring 172 from the spool 139 (FIG. 10B) onto the drive wheel 128. This action stores potential energy in the constant torque spring so that the constant torque spring wants to return to the spool 139 (FIG. 10B).

Figure 14A:
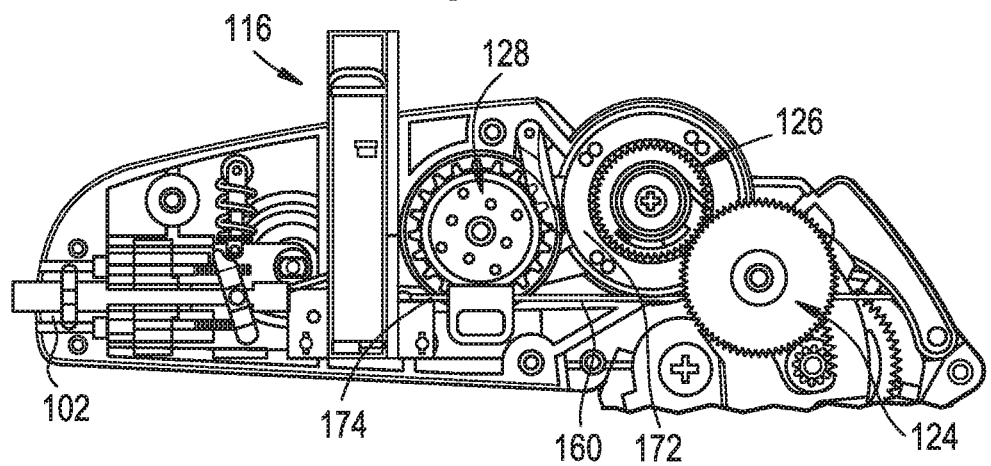
Figures 1, 14A:
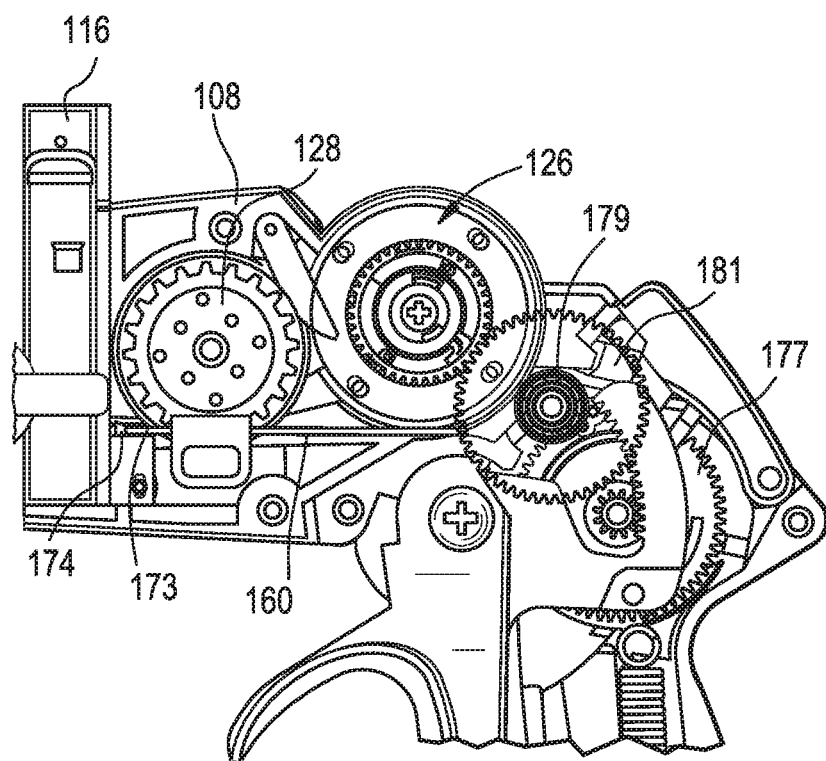

Referring to FIG. 14A, in one embodiment, an insertion tool 174, adapted to engage a surgical fastener, is attached to the distal end of the flexible member 160. In FIG. 14A, the insertion tool 174 is positioned proximal to the cartridge 116 and the plurality of surgical fasteners that are stacked within the cartridge. In the stage of the firing cycle shown in FIG. 14A, the proximal end of the flexible member 160 has been wound onto the storage reel 126 and the constant torque spring 172 has been wound from the spool 139 (FIG. 10B) onto the drive wheel 128.

Referring to FIG. 14A-1, in one embodiment, when the trigger 112 has almost reached a fully squeezed position (i.e., almost fully closed), the insertion tool 174 attached to the distal end of the flexible member 160 has been retracted to a position that is proximal to the cartridge 116 and the stack of surgical fasteners disposed within the cartridge. In one embodiment, the housing 108 preferably includes a proximal hard stop 173 that engages the insertion tool 174 for preventing further proximal movement of the insertion tool 174. At this stage of the firing cycle, the teeth on a large drive gear 177 are about to disengage from the teeth on a smaller clutch gear 179 for decoupling the storage reel 126 from the large drive gear 177.

Figure 14B:
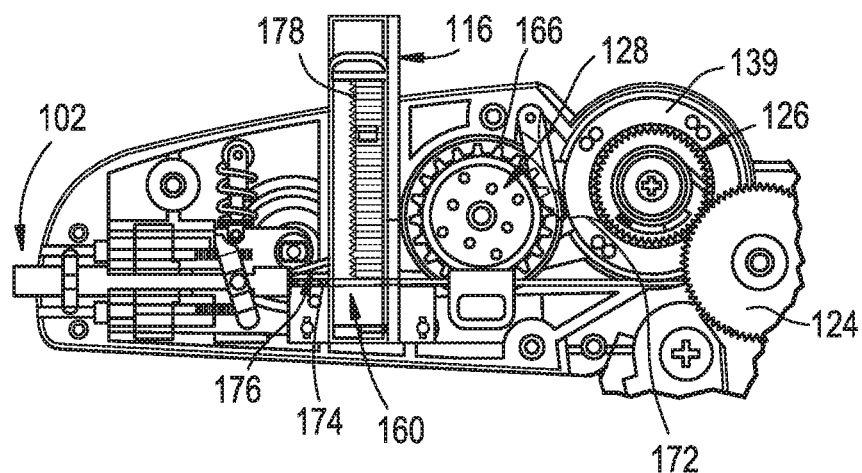
Figures 1, 14B:
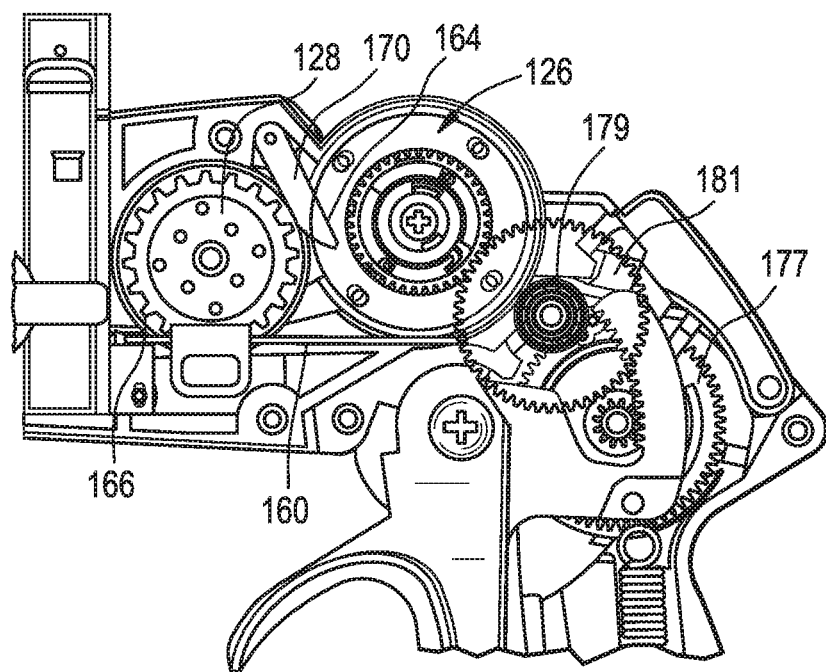

Referring to FIGS. 14B and 14B-1, at the end of rotation of the large drive gear 177 of the drive train 124, the large drive gear 177 disengages from the smaller clutch gear 179 for removing the tensile constraint on the flexible member 160. In one embodiment, once the gear teeth on the large drive gear 177 no longer engage the gear teeth on the smaller clutch gear 179, the drive wheel 128 and the storage reel 126 are decoupled from the large drive gear 177 and are free to rotate relative to the large drive gear 177, at which point, the energy stored in the constant torque spring 172 (FIG. 14A) is released for rotating the drive wheel 128 in a clockwise direction, which, in turn, drives the flexible member 160 and the insertion tool 174 toward the distal end of the elongated shaft 102. At this stage, the constant torque spring 172 applies a constant force to the drive wheel 128, resulting in constant acceleration of the drive wheel 128, the flexible member 160, the insertion tool 174, and the storage reel 126. As the drive wheel 128 rotates in a clockwise direction, the teeth 166 on the drive wheel 128 engages the openings on the flexible member 160 for driving the flexible member in a distal direction. As the insertion tool 174 is driven distally, it strips a surgical fastener from the bottom of the stack of surgical fasteners disposed within the cartridge 116 and advances the stripped surgical fastener toward the distal end of the elongated shaft 102 for being dispensed into tissue (e.g., to secure a surgical mesh to tissue). Referring to FIG. 14B-1, in one embodiment, the pivoting stop 170 is seated in the notch 164 of the storage reel 126 for halting further clockwise rotation of the storage reel, which, in turn, halts distal movement of the flexible member 160.

Figure 15A:
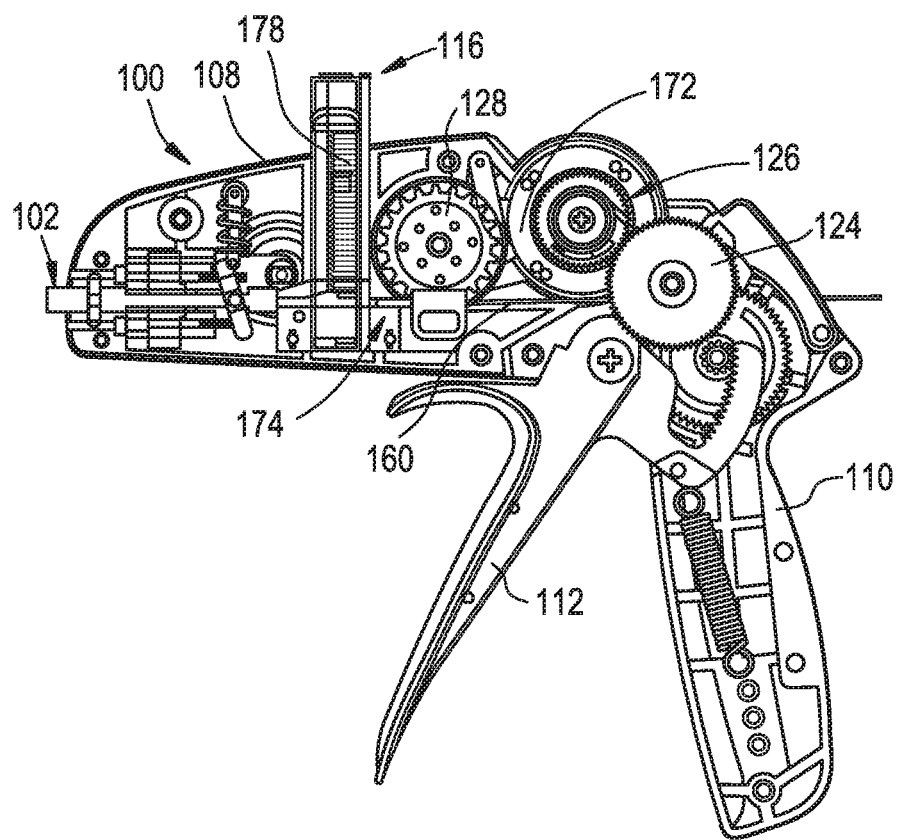
FIG. 15A shows a cross-sectional view of an applicator instrument for dispensing surgical fasteners prior to the commencement of a firing cycle, in accordance with one embodiment of the present patent application.
Figure 15B:
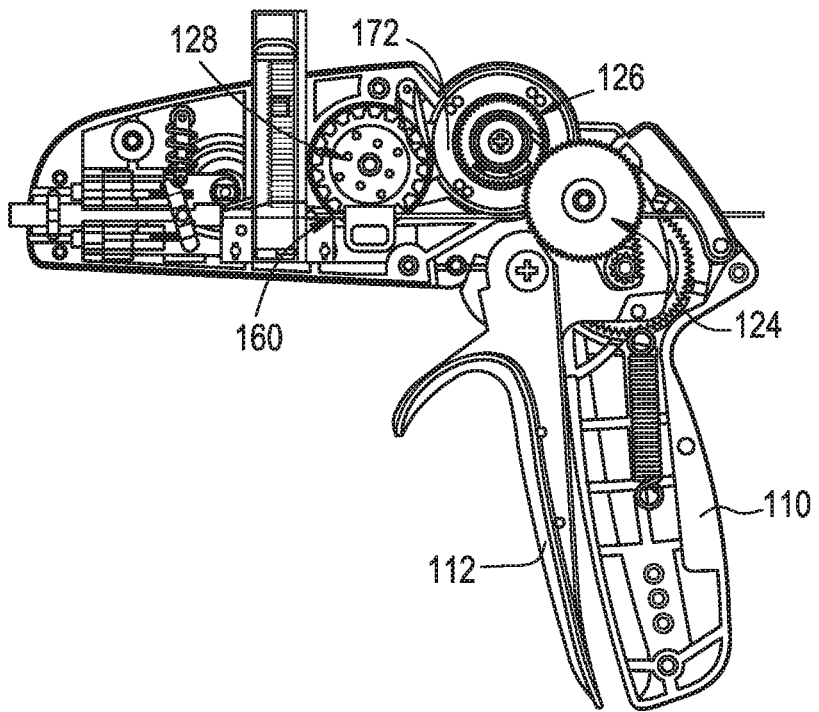
FIG. 15B shows a cross-sectional view of the applicator instrument of FIG. 15A during a later stage of the firing cycle, in accordance with one embodiment of the present patent application.

Referring to FIGS. 15A and 15B, in one embodiment, prior to the commencement of a firing cycle, the insertion tool 174 attached to the distal end of the flexible member 160 is located within the housing 108 of the applicator instrument 100 and is proximal to the surgical fastener stack 178 within the cartridge 116. The surgical fastener stack 178 is located within the cartridge 116. The flexible member 160 is wound onto the storage reel 126 and energy is stored in drive wheel 128 prior or during each firing cycle. This system may be referred to as having a "coiled snake" firing system. During the trigger actuation, the energy is released to accelerate the drive wheel 128 and flexible member 160 toward the distal end of the instrument.

Figure 16A:
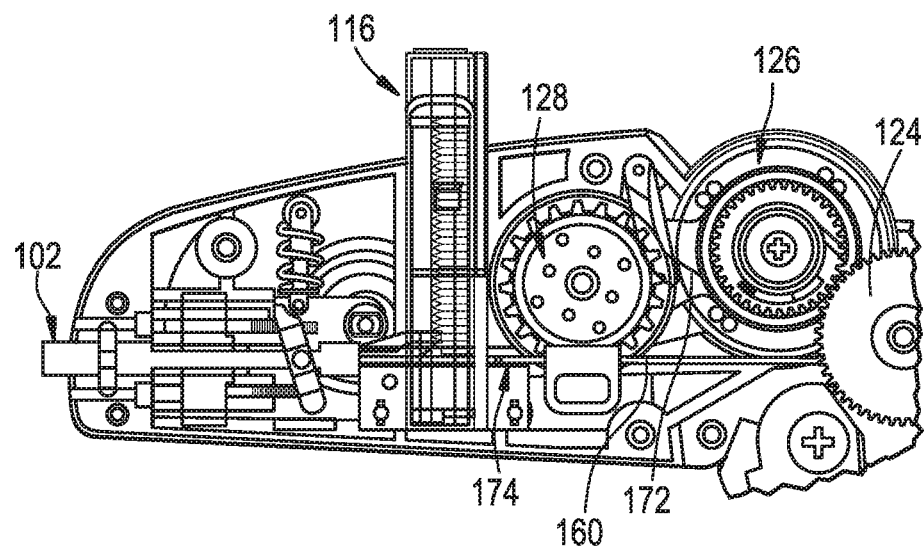
FIG. 16A shows a magnified view of the firing system shown in FIG. 15B.

Referring to FIGS. 15B and 16A, in one embodiment, the user squeezes the trigger 112 toward the handle 110 so that the gear train 124 rotates the drive wheel 128 in a counterclockwise direction for winding the constant torque spring 172 from the spool 139 (FIG. 10B) onto the drive wheel 128.

Figure 16B:
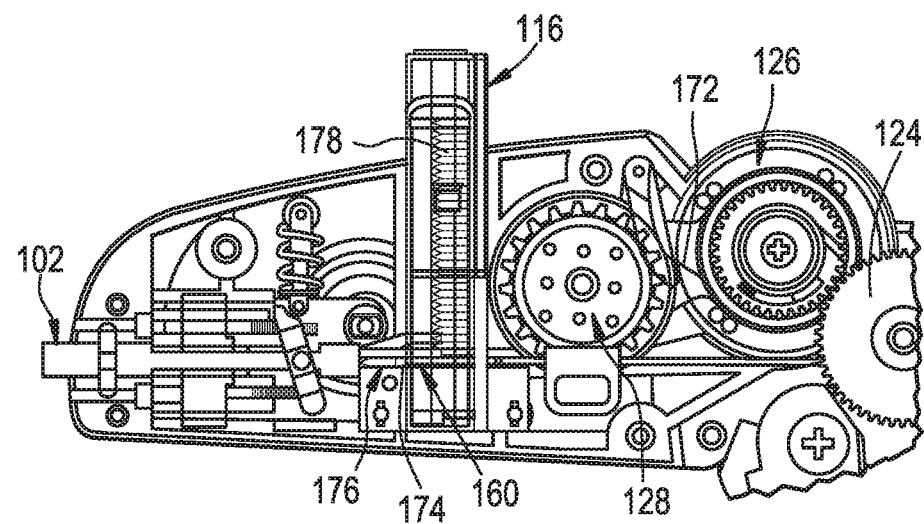
FIG. 16B shows the firing system of FIG. 16A during a later stage of the firing cycle.

Referring to FIG. 16B, in one embodiment, during a later stage of the firing cycle, the gear train 124 may decouple the trigger from the storage reel 126, thereby freeing the storage reel 126 to rotate so that the constant torque spring can rotate the drive wheel 128 in a clockwise direction for advancing the flexible member toward the distal end of the elongated shaft. In one embodiment, the constant torque spring 172 moves from the drive wheel 128 back to the spool 139 (FIG. 10B) of the storage reel 126 for rotating the drive wheel 128 in a clockwise direction and driving the flexible member 160 and the insertion tool 174 at the distal end of the flexible member 160 toward the distal end of the elongated shaft 102. As the insertion tool is driven distally, the insertion tool 174 desirably strips a lower-most surgical fastener 176 from the bottom of the surgical fastener stack 178 within the cartridge 116 and advances the stripped surgical fastener toward the distal end of the elongated shaft 102.

Figure 16C:
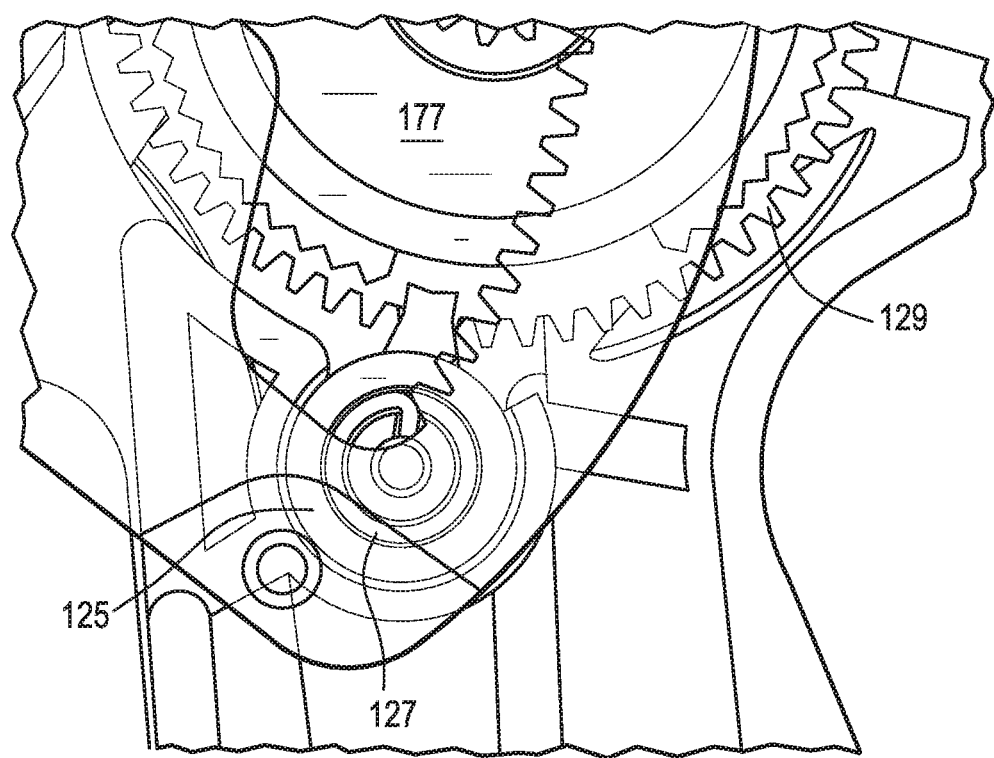
FIGS. 16C and 16D show a one-way pawl for engaging supplemental teeth on a drive gear, in accordance with one embodiment of the present patent application.
Figure 16D:
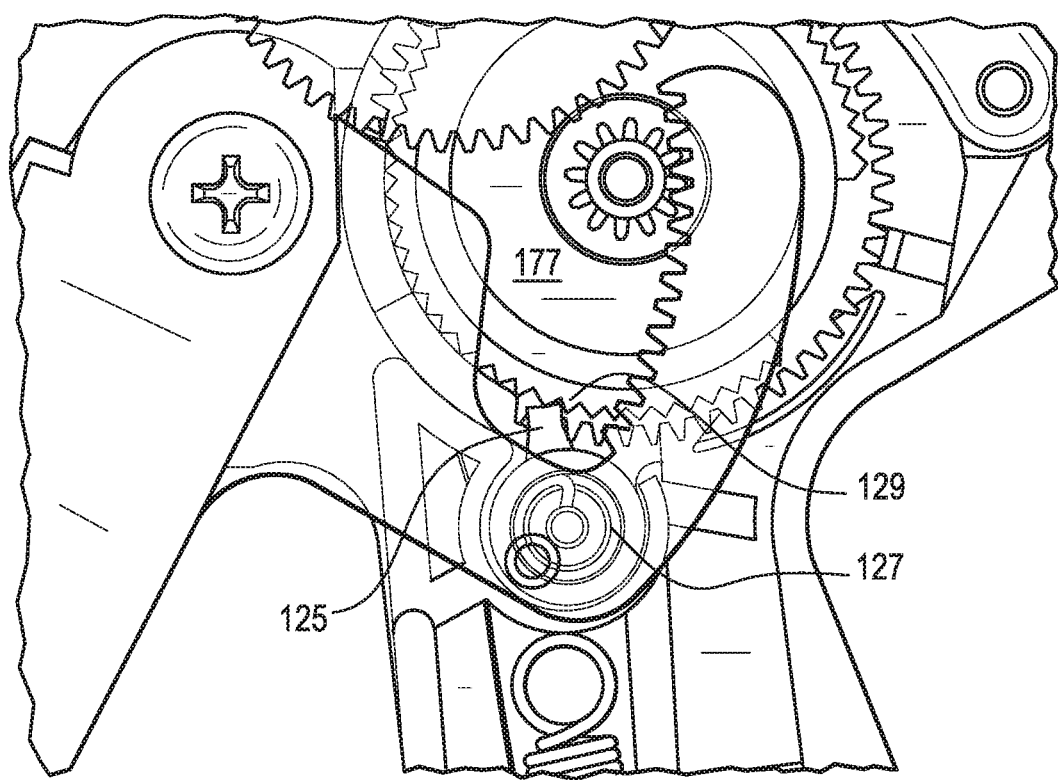

Referring to FIGS. 16C and 16D, in one embodiment, a one-way pawl 125 engages with a member of the gear train 124. In one embodiment, a drive gear 177 has teeth 129 that are adapted to engage the pawl 125. The pawl 125 preferably ensures that a user must fully squeeze and fully release the trigger. If the trigger is partially deployed in either direction, the pawl 125 will desirably engage the gear train and prevent the gear train from moving in the opposite direction. Once the trigger reaches the limits of its travel, the pawl 125 will be spring loaded via a pawl reset spring 127 to allow the pawl to reset for travel in the opposite direction. In one embodiment, a drive gear has teeth 129 that are adapted to engage the pawl 125 to prevent partial squeezing of the trigger.

Figure 17:
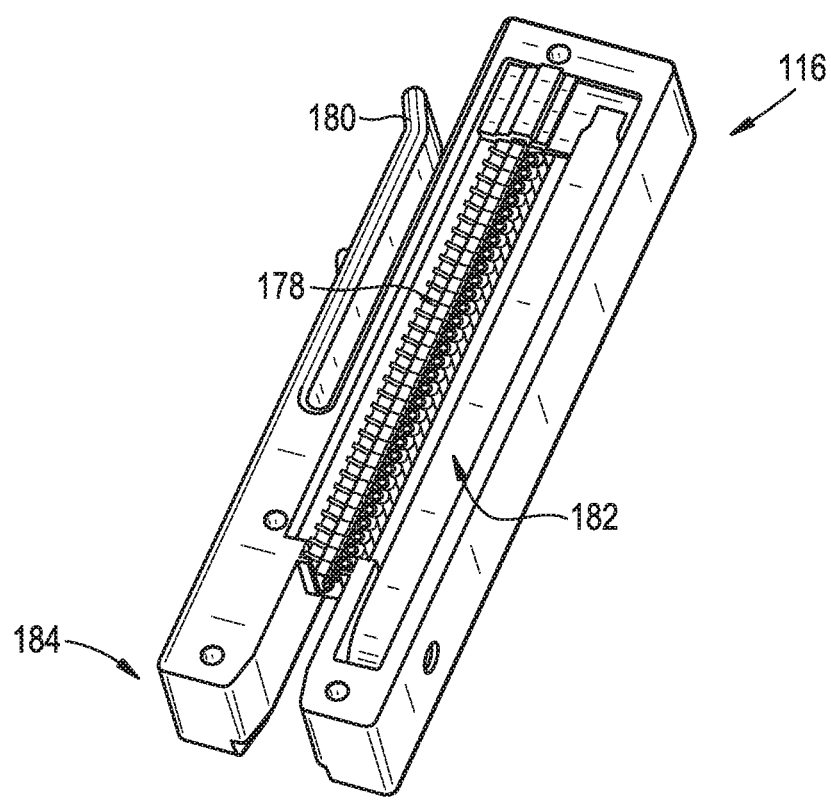
FIG. 17 shows a spring-loaded cartridge containing a plurality of stacked surgical fasteners, in accordance with one embodiment of the present patent application.

Referring to FIG. 17, in one embodiment, a cartridge 116 contains a stack of surgical fasteners 178. An outer surface of the cartridge 116 includes a catch 180 that enables the cartridge 116 to be snap-fit into the housing 108 (FIG. 2A) of an applicator instrument. In one embodiment, a cartridge release button 118 (FIG. 2A) may be depressed for disengaging from the catch 180 so that the cartridge 116 may be removed from the snap-fit connection with the housing. In one embodiment, the user may depress the catch 180 so that the cartridge 116 may be removed from the snap-fit connection with the housing 108. In one embodiment, the cartridge 116 includes a constant force spring 182 that urges the surgical fasteners 178 toward the lower end 184 of the cartridge 116. In one embodiment, the constant force spring pulls on a cartridge sled 183, which pushes on the stack of surgical fasteners.

Figure 18A:
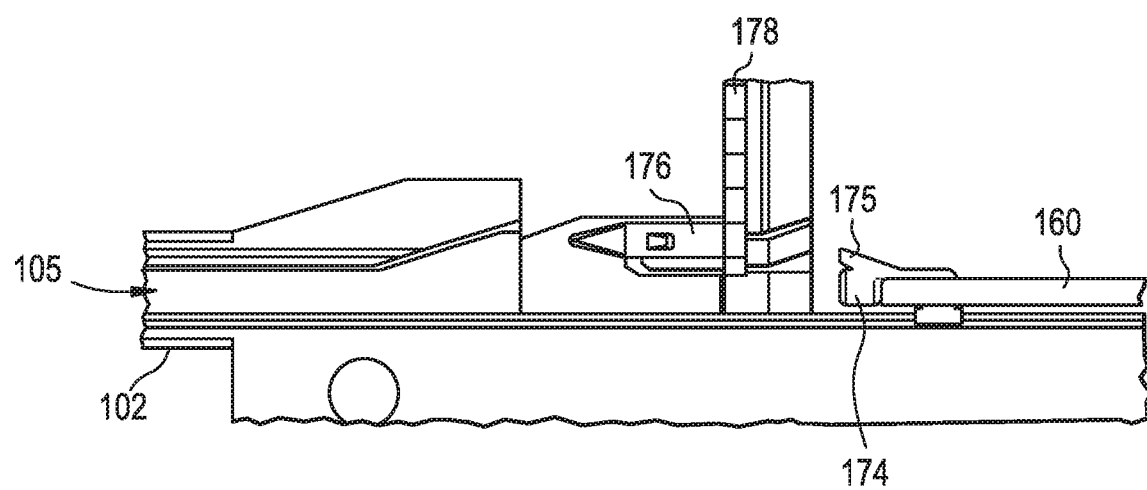
FIGS. 18A-18D show a method of using a pusher secured to a distal end of a flexible member for removing a lowermost surgical fastener from a cartridge, in accordance with one embodiment of the present patent application.

Referring to FIG. 18A, in one embodiment, the insertion tool 174 attached to the distal end of the flexible member 160 is adapted to strip a lower-most surgical fastener 176 from the bottom of the surgical fastener stack 178. The insertion tool 174 desirably includes a fin 175 that projects above a main body of the insertion tool 174 at a distal-most end of the insertion tool for engaging a rear surface of the lower-most surgical fastener 176. The insertion tool 174 is adapted to strip the lower-most surgical fastener 176 from the bottom of the stack and advance the surgical fastener through a conduit 105 of the elongated shaft 102 for dispensing the surgical fastener 176 from the distal-most end of the elongated shaft.

Figure 18B:
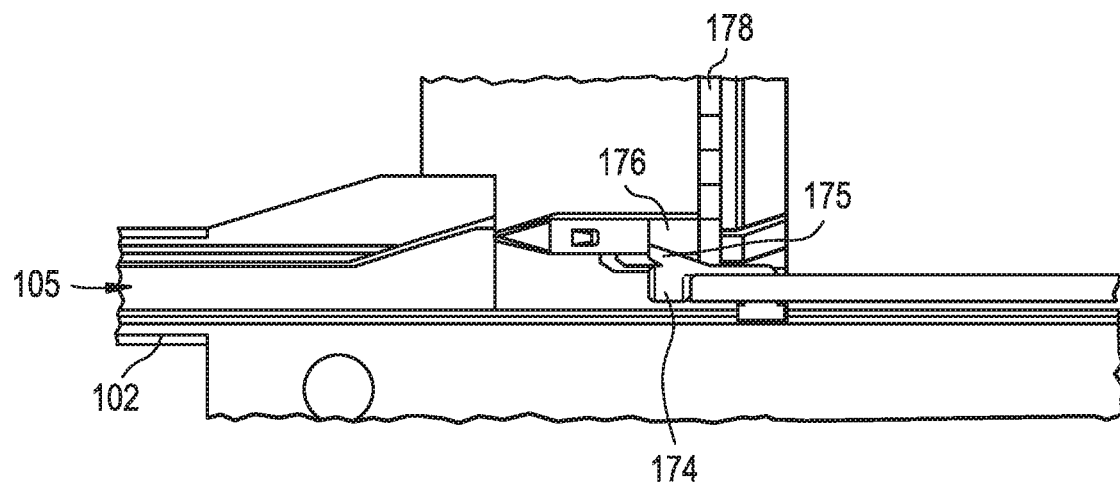
Figure 18C:
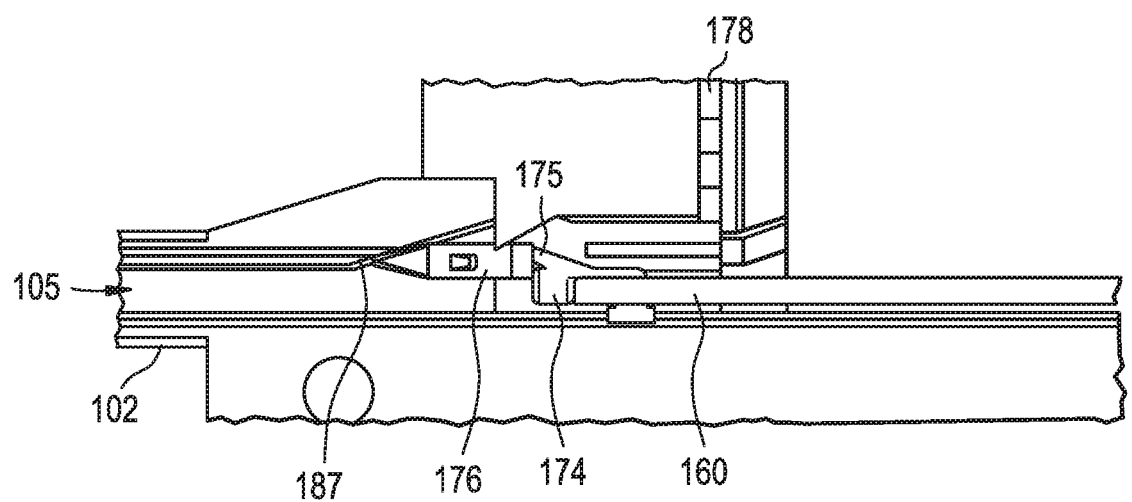
Figure 18D:
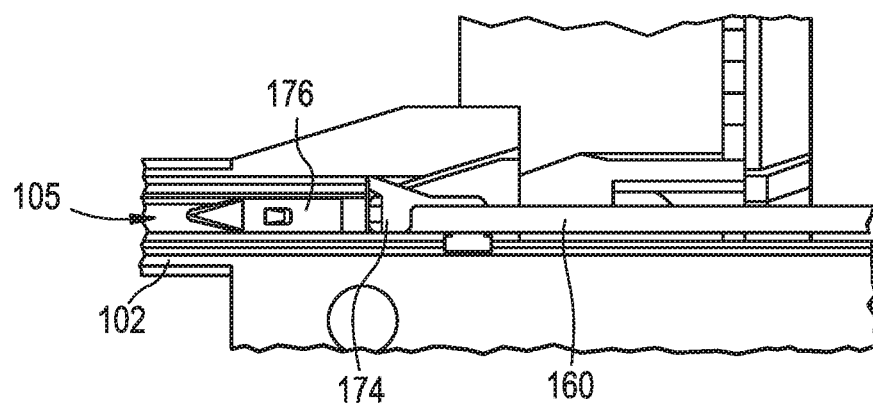

Referring to FIG. 18B, in one embodiment, the fin 175 of the insertion tool 174 contacts the proximal or trailing end of the lower-most surgical fastener 176 for stripping the surgical fastener 176 from the bottom of the stack 178. Referring to FIGS. 18C and 18D, in one embodiment, the flexible member 160 and the insertion tool 174 move distally for guiding the stripped surgical fastener 176 into the conduit 105 of the elongated shaft 102. As shown in FIG. 18C, ramped features 187 within the track simultaneously bias the tips of the surgical fastener and the inner crown of the surgical fastener. These ramped features ensure that the entire surgical fastener drops vertically with minimal angling. Angling of the surgical fastener should be avoided to reduce opportunities for jamming. The flexible member 160 continues to move distally until the insertion tool 174 dispenses the surgical fastener 176 from the distal-most end of the elongated shaft 102.

Figure 19A:
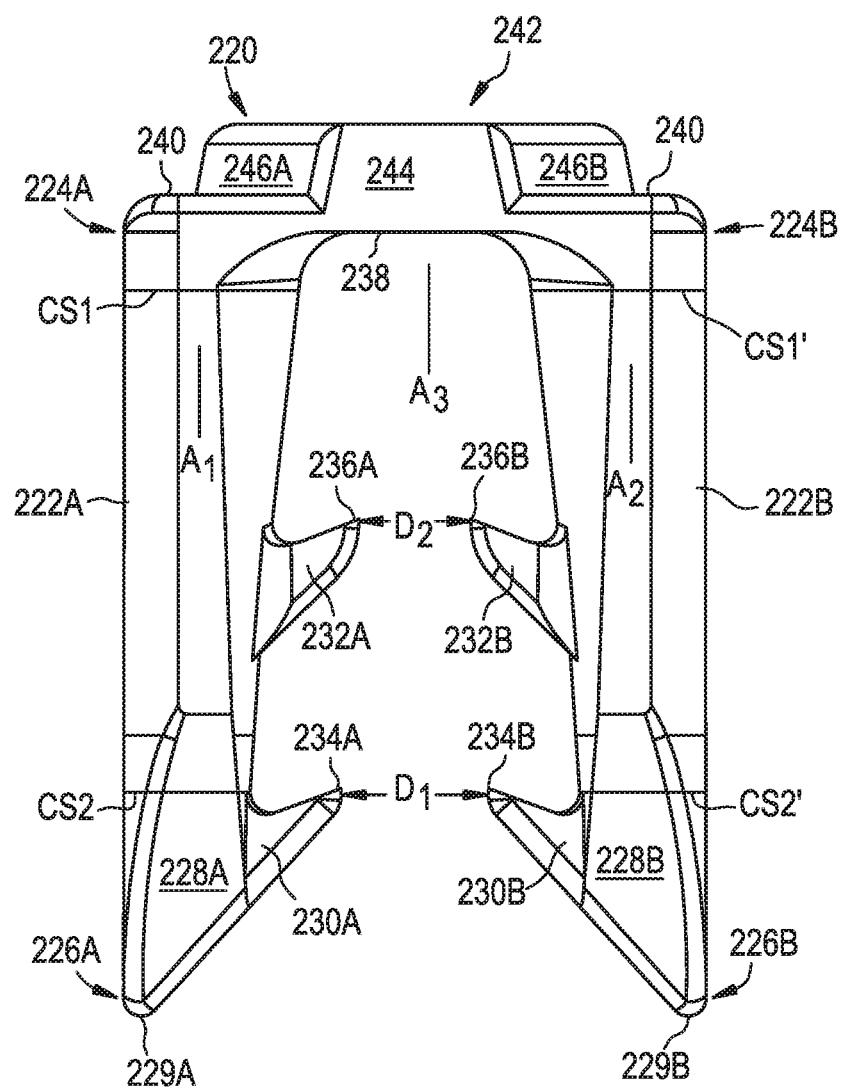
FIGS. 19A-19H show a surgical fastener used to secure prosthetic devices to tissue, in accordance with one embodiment.
Figure 19B:
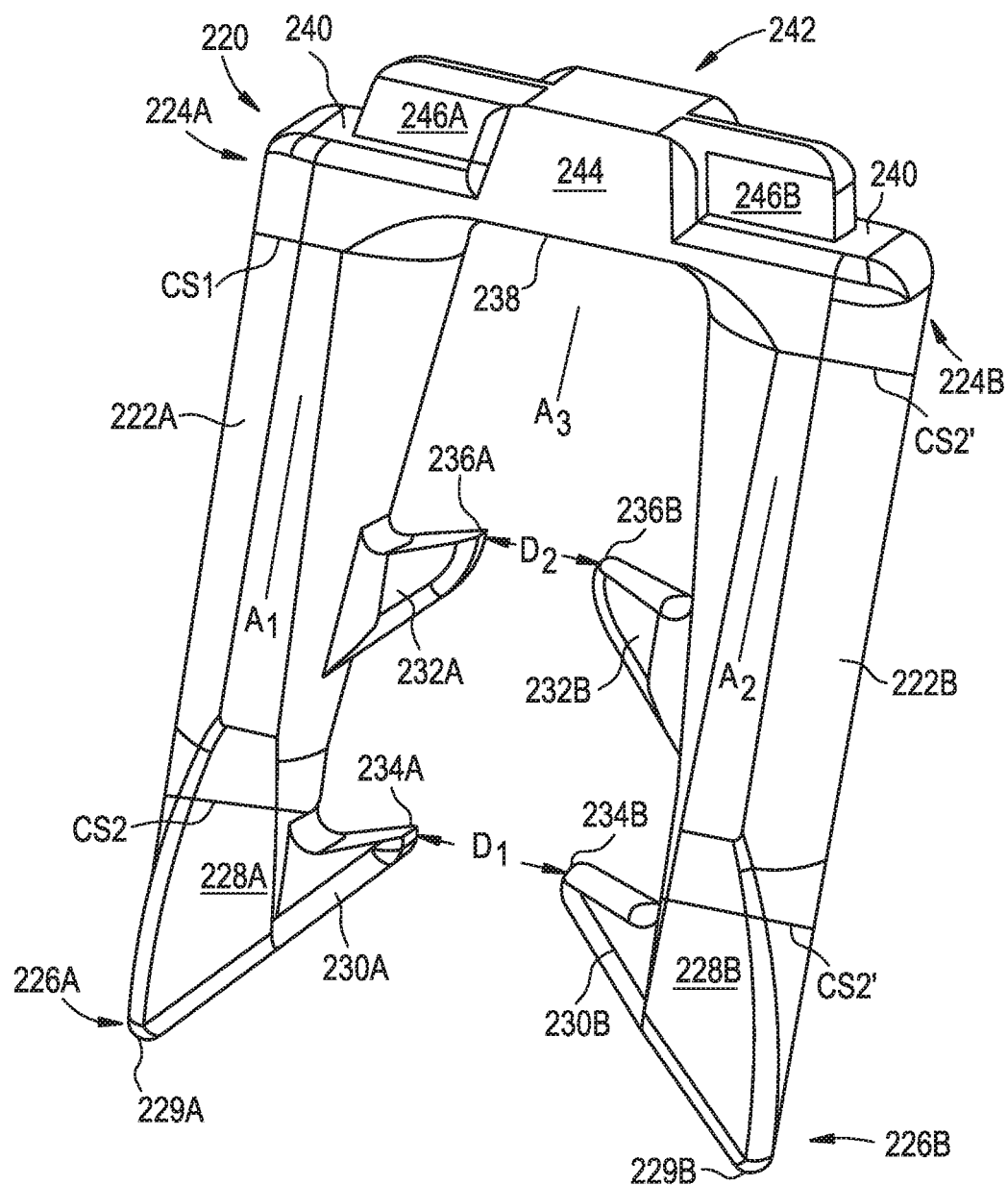
Figure 19C:
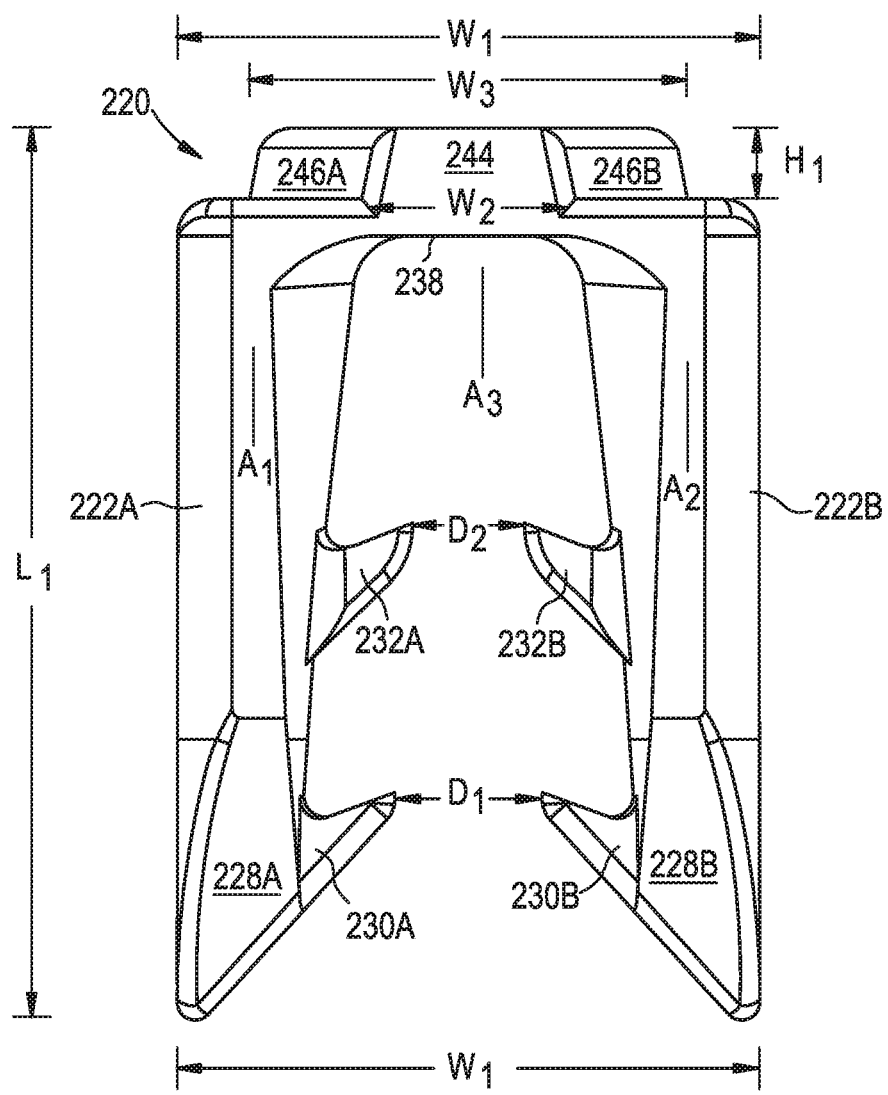

Referring to FIGS. 19A-19C, in one embodiment, a surgical fastener 220 for securing prosthetic devices (e.g., surgical mesh) to tissue preferably includes a first leg 222A having a proximal end 224A and a distal end 226A. In one embodiment, a first cross sectional area CS1 adjacent the proximal end 224A of the first leg 222A is greater than a second cross sectional area CS2 adjacent the distal end 226A of the first leg 222A. In one embodiment, the first leg 222A tapers inwardly between the proximal end 224A of the first leg 222A and the distal end 226A of the first leg 222A. In one embodiment, the largest cross sectional area of the first leg is adjacent the proximal end 224A of the first leg and the first leg tapers inwardly between the proximal end and the distal end thereof.

In one embodiment, the first leg 222A extends along a first longitudinal axis $A_1$. In one embodiment, the first leg 222A includes an insertion tip 228A located at the distal end 226A of the first leg. In one embodiment, the insertion tip 228A has a distal-most point 229A. In one embodiment, the insertion tip 228A is asymmetrical so that it skews outwardly relative to the longitudinal axis $A_1$ of the first leg 222A.

In one embodiment, the surgical fastener 220 preferably includes a second leg 222B having a proximal end 224B and distal end 226B. The second leg 222B desirably has a first cross sectional area CS1' adjacent the proximal end 224B that is greater than a second cross sectional CS2' adjacent the distal end 226B. In one embodiment, the second leg 222B tapers inwardly between the proximal end 224B of the second leg 222B and the distal end 226B of the second leg 222B. In one embodiment, the second leg 222B has an insertion tip 228B located at the distal end thereof. In one embodiment, the insertion tip 228B has a distal-most point 229B. In one embodiment, the second leg 222B extends along a second longitudinal axis $A_2$ that is parallel to the first longitudinal axis $A_1$ of the first leg 222A. In one embodiment, the insertion tip 228B on the second leg 222B is asymmetrical and skews outwardly relative to the second longitudinal axis $A_2$ of the second leg 222B.

In one embodiment, the first leg 222A includes a distal barb 230A. In one embodiment, the distal barb 230A is positioned adjacent the distal end 226A of the first leg 222A and is proximal to the distal-most point 229A on the insertion tip 228A. The distal barb 230A preferably extends inwardly toward the second leg 222B. In one embodiment, the first leg 222A has a proximal barb 232A that also extends inwardly toward the second leg 222B. In one embodiment, the proximal barb 232A on the first leg 222A is located between the proximal end 224A of the first leg 222A and the distal barb 230A. In one embodiment, the proximal barb 232A is located about halfway between the proximal end 240A and the distal end 226A of the first leg 222A.

In one embodiment, the second leg 222B of the surgical fastener 220 preferably includes a distal barb 230B that extends inwardly toward the first leg 222A. In one embodiment, the distal barbs 230A, 230B on the respective first and second legs 222A, 222B oppose one another, extend toward one another, and are aligned with one another along the lengths of the respective first and second legs 222A, 222B.

In one embodiment, the second leg 222B includes a proximal barb 232B that extends inwardly toward the first leg 222A. In one embodiment, the proximal barbs 232A, 232B on the respective first and second legs 222A, 222B extend toward one another, oppose one another, and are aligned with one another along the lengths of the respective first and second legs 222A, 222B.

In one embodiment, the surgical fastener 220 extends along a central axis $A_3$ that bisects the surgical fastener 220 into a first half including the first leg 222A with the associated barbs 230A, 232A, and a second half including the second leg 222B with the associated barbs 230B, 232B. The central axis $A_3$ is preferably parallel to both the first longitudinal axis $A_1$ of the first leg 222A and the second longitudinal axis $A_2$ of the second leg 222B. In one embodiment, the central axis $A_3$ bisects the surgical fastener 220 for splitting the surgical fastener into two evenly sized parts and is equidistant from the first longitudinal axis $A_1$ of the first leg 222A and the second longitudinal axis $A_2$ of the second leg 222B.

In one embodiment, the distal barb 230A on the first leg 222A has an inner tip 234A and the distal barb 230B on the second leg 222B has an inner tip 234B. The respective inner tips 234A, 234B define a distance $D_1$ that extends along an axis that is perpendicular to the central axis $A_3$ of the surgical fastener 220.

In one embodiment, the proximal barb 232A on the first leg 222A has an inner tip 236A and the proximal barb 232B on the second leg 222B has an inner tip 236B. The inner tips 236A, 236B define a distance $D_2$ that extends along an axis that is perpendicular to the central axis $A_3$ of the surgical fastener 220. In one embodiment, the distance $D_1$ between the inner tips 234A, 234B of the respective distal barbs 230A, 230B is greater than the distance $D_2$ between the inner tips 236A, 236B of the proximal barbs 232A, 232B. In one embodiment, the distance $D_1$ is about 0.030 inches and the distance $D_2$ is about 0.025 inches.

In one embodiment, the first and second insertion tips 228A, 228B are advanced into tissue followed by the first and second distal barbs 230A, 230B to form two spaced tissue openings. In one embodiment, the two tissue openings will be about 0.030 inches apart from one another, which is equal to the distance $D_1$ between the inner tips 234A, 234B of the first and second distal barbs 230A, 230B. In one embodiment, the first and second proximal barbs 232A, 232B are closer together than are the first and second distal barbs 234A, 234B, which enables the first and second proximal barbs 236A, 236B to grip onto the side walls of the tissue openings previously formed by the first and second distal barbs 230A, 230B. Thus, an important tissue anchoring benefit is gained by providing proximal barbs 232A, 232B that are closer together than the distal barbs 230A, 230B.

In one embodiment, the surgical fastener 220 may be made of absorbable and/or non-absorbable materials. Preferred absorbable materials include PDS, PDS/lactide-glycolide blends, PLA, etc. In one embodiment, each surgical fastener is sized to fit inside of a 5 mm outer diameter tube (a typical trocar cannula dimension). The surgical fastener is fabricated by molding, however, with small modifications, other processes such as casting, stamping, and machining may be used. In one embodiment, the surgical fasteners may be extruded into a general shape, and then formed. In one embodiment, the surgical fasteners may be printed using a 3-D printer.

Referring to FIGS. 19A-19D, in one embodiment, the surgical fastener 220 preferably includes a bridge 238 that interconnects the proximal ends 224A, 224B of the respective first and second legs 222A, 222B. The central axis $A_3$ of the surgical fastener 220 desirably bisects the bridge. In one embodiment, the bridge 238 includes a major surface 240 that extends adjacent the proximal ends 224A, 224B of the first and second legs 222A, 222B, and a crown 242 that projects proximally from the major surface 240 to define a proximal-most portion of the surgical fastener 220. In one embodiment, the major surface 240 is flat. As will be described in more detail herein, the major surface 240 is preferably engaged by a distal end of a flexible member or by an insertion tool secured to the distal leading of a flexible member for applying an insertion force to the surgical fastener and controlling the orientation of the surgical fastener as the surgical fastener is dispensed from an applicator instrument. In one embodiment, the crown 242 includes a center section 244 that spans the thickness $T_1$ (FIG. 19D) of the surgical fastener 220 and first and second lateral flanges 246A, 246B that extend laterally from the center section 244.

Figure 19D:
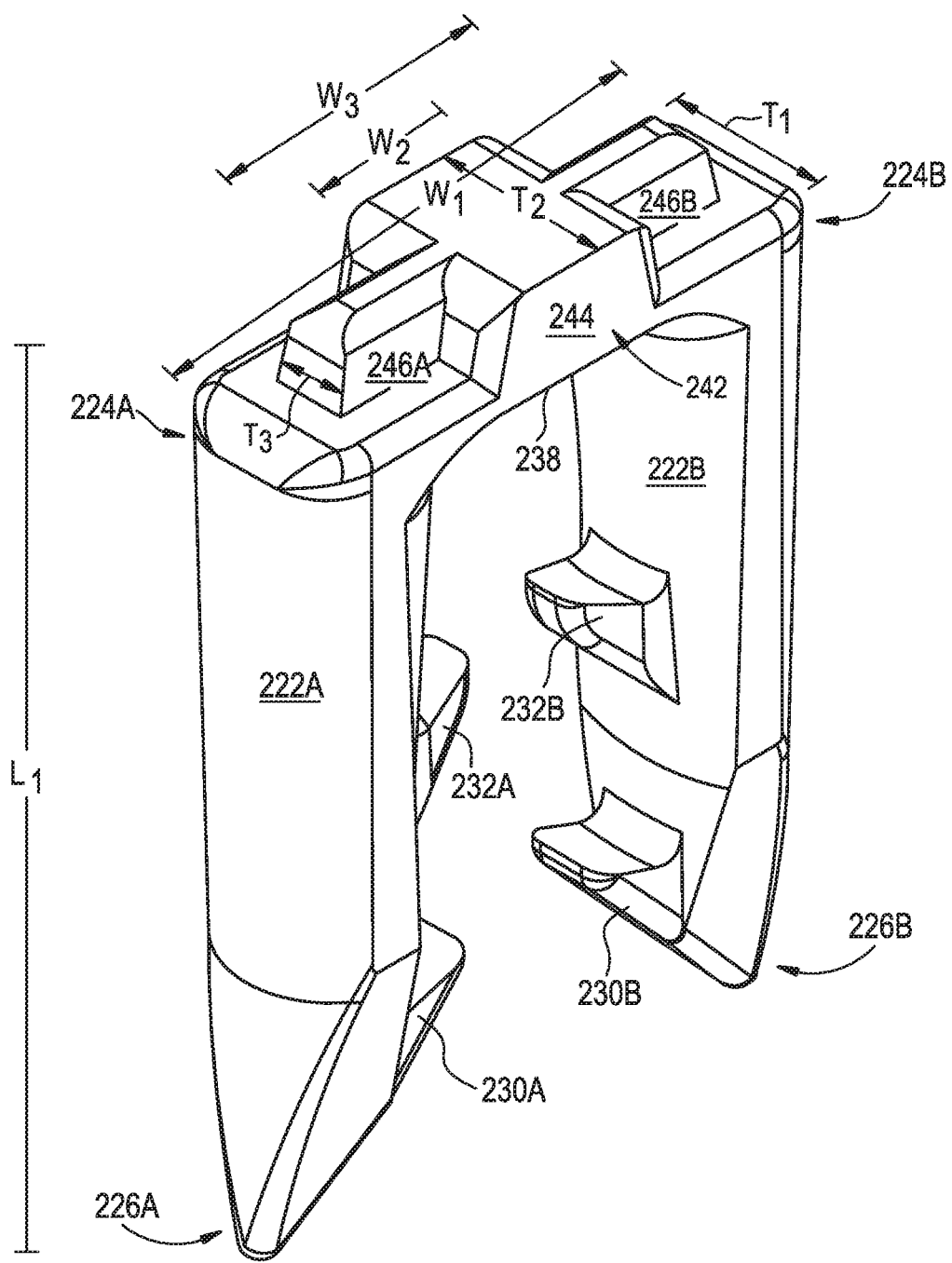

Referring to FIGS. 19C and 19D, in one embodiment, the surgical fastener 220 has a length $L_1$ of about 0.248 inches, a width $W_1$ of about 0.160 inches, and a thickness $T_1$ of about 0.05 inches. In one embodiment, the width $W_1$ of the surgical fastener 220 is the same at both the proximal and distal ends thereof, and the width $W_1$ remains constant between the proximal and distal ends of the surgical fastener to aide with feeding. In other words, the width $W_1$ defined by the distance between the outer surfaces of the first and second legs 222A, 222B at the proximal ends 224A, 224B of the legs equals the distance between the outer surfaces of the insertion tips 228A, 228B at the distal ends of the first and second legs 222A, 222B. In one embodiment, the cross-sectional areas of the legs decrease when moving from the proximal ends to the distal ends of the respective first and second legs 222A, 222B, however, the width $W_1$ of the surgical fastener remains constant between the proximal and distal ends of the first and second legs.

In one embodiment, the center section 244 of the crown 242 has a width $W_2$ of about 0.057 inches and the laterally extending flanges 246A, 246B define a width $W_3$ of about 0.120 inches.

Figure 19E:
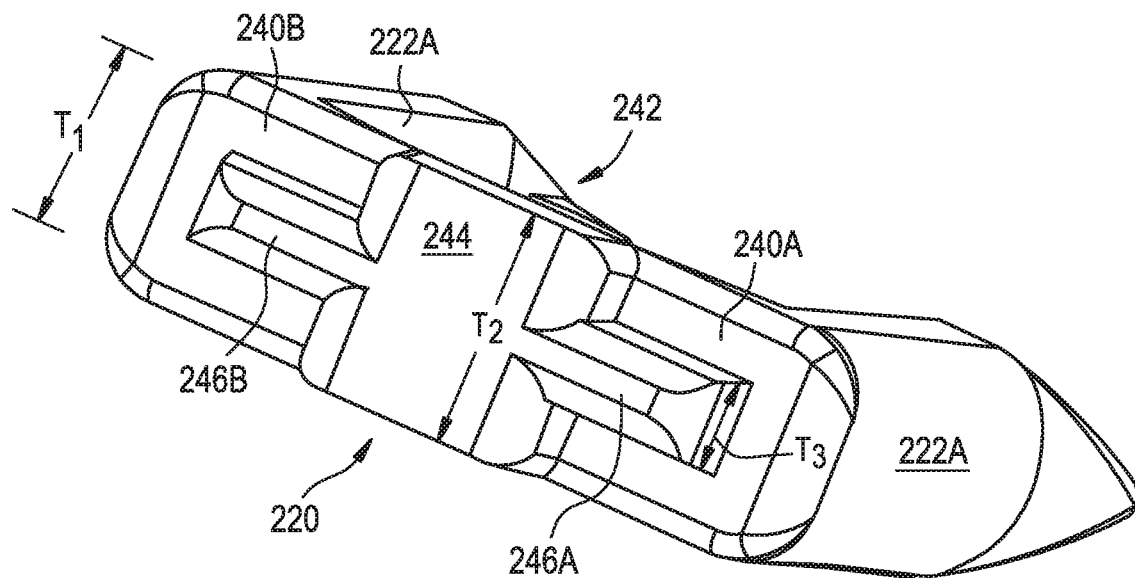

Referring to FIGS. 19D and 19E, the center section 244 of the crown 242 defines a thickness $T_2$ that equals the thickness $T_1$ of the surgical fastener 220. In one embodiment, the laterally extending flanges 246A, 246B have a thickness $T_3$ of about 0.020 inches.

Figure 19F:
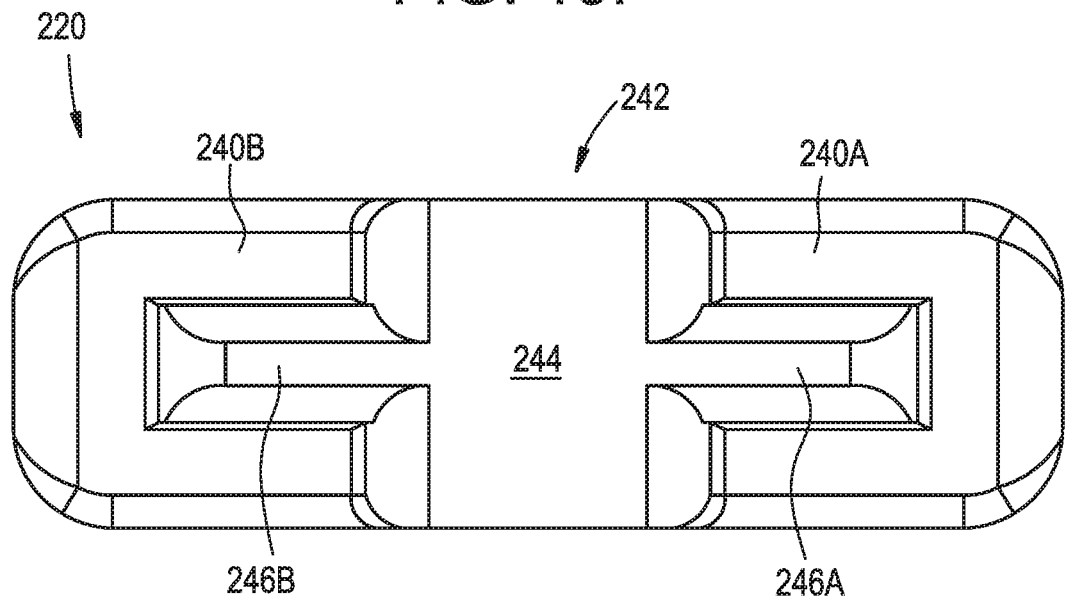

Referring to FIGS. 19E and 19F, in one embodiment, the crown 242 at the proximal end of the surgical fastener 220 desirably includes the center section 244 and the first and second laterally extending flanges 246A, 246B that extend laterally from the center section 244. The major surface 240 of the bridge extends around the sides of the respective first and second laterally extending flanges 246A, 246B. In one embodiment, a first section 240A of the major surface 240 extends around the first laterally extending flange 246A and has a C-shape, and a second section 240B of the major surface 240 extends around the second laterally extending flange 246B and has a C-shape. The C-shaped first and second sections 240A, 240B of the major surface 240 have the same shape and configuration and oppose one another on opposite sides of the center section 244. In one embodiment, the C-shaped sections 240A, 240B are aligned with the respective longitudinal axes $A_1$, $A_2$ of the first and second legs 222A, 222B (FIG. 19A).

Figure 19G:
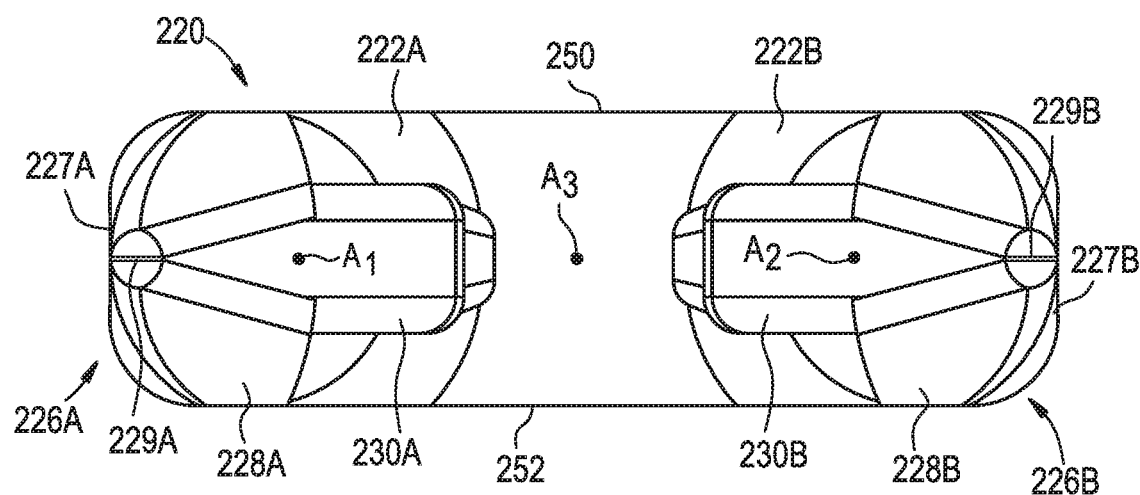

Referring to FIG. 19G, in one embodiment, the first leg 222A of the surgical fastener 220 has a distal end 226A with the first insertion tip 228A having the distal-most point 229A. In one embodiment, the first insertion tip 228A is skewed outwardly relative to the longitudinal axis $A_1$ of the first leg 222A. The first leg 222A includes the distal barb 230A that extends inwardly toward the second leg 222B of the surgical fastener 220. The second leg 222B has a distal end 226B with the second insertion tip 228B having the distal-most point 229B. In one embodiment, the second insertion tip 228B is skewed outwardly relative to the longitudinal axis $A_2$ of the second leg 222B. The second leg 222B includes the distal barb 230B that extends inwardly toward the first leg 222A. In one embodiment, the distal barbs 230A, 230B extend toward one another, oppose one another, and are aligned with one another adjacent the distal ends 226A, 226B of the respective first and second legs 222A, 222B. The central axis $A_3$ bisects the surgical fastener into a first half including the first leg 222A and a second half including the second leg 222B.

Figure 19H:
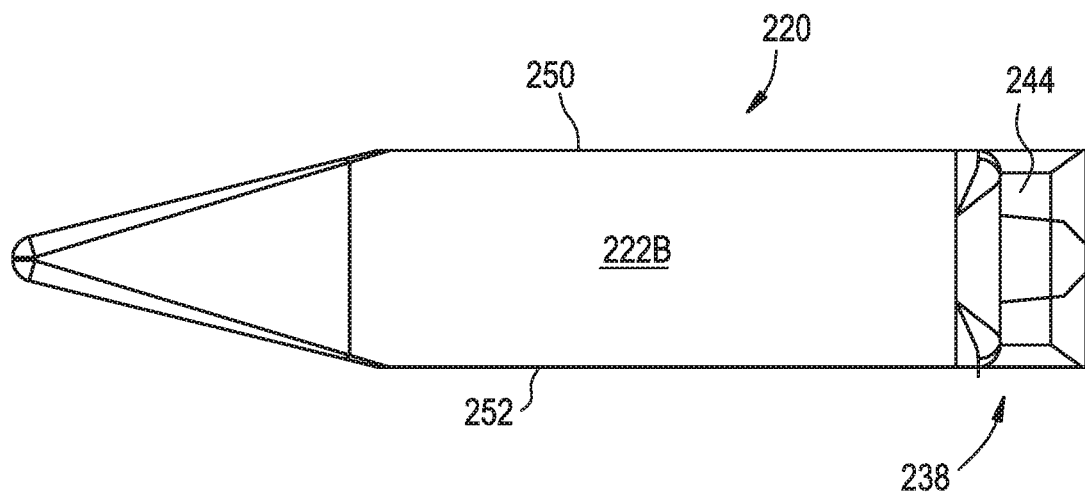

Referring to FIGS. 19D and 19G, in one embodiment, the first distal barb 230A and the first proximal barb 232A have respective thicknesses that are less than the thickness or diameter of the first leg 222A, and the second distal barb 230B and the second proximal barb 232B have respective thicknesses that are less than the thickness or diameter of the second leg 222B Referring to FIGS. 19G and 19H, in one embodiment, the surgical fastener 220 desirably includes a first major surface 250 that extends over a top side of the surgical fastener 220 and a second major surface 252 that extends over an underside of the surgical fastener 220. In one embodiment, the first major surface 250 is flat and extends over the center section 244 of the crown 242 and the first and second legs 222A, 222B of the surgical fastener. In one embodiment, the second major surface 252 is also flat and extends over opposite sides of the center section 244 of the crown 242 and the first and second legs 222A, 222B. The flat, first and second major surfaces 250, 252 may be used to control the orientation of the surgical fastener as it moves distally through the shaft of an applicator instrument.

In one embodiment, the first leg 222A desirably has an outer surface 227A that extends along the length of the first leg. In one embodiment, the outer surface 227A of the first leg 222A may include a flat surface that is used to control the orientation of the surgical fastener as it moves distally through the shaft of an applicator instrument. In one embodiment, the second leg 222B desirably has an outer surface 227B that extends along the length of the second leg. In one embodiment, the outer surface 227B of the second leg 222B may include a flat surface that is used to control the orientation of the surgical fastener as it moves distally thorough the shaft of an applicator instrument.

Figure 20:
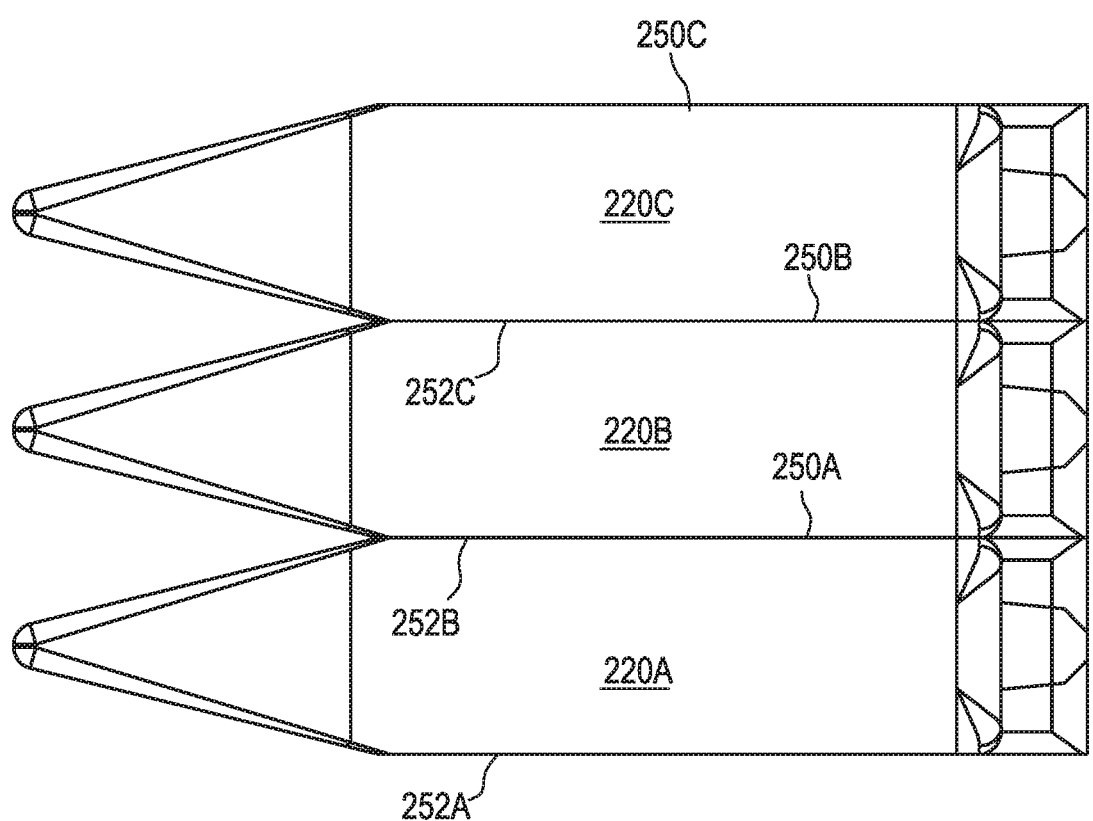
FIG. 20 shows the surgical fastener of FIGS. 19A-19H in a stacked array, in accordance with one embodiment.

Referring to FIGS. 19H and 20, in one embodiment, the flat top and bottom major surfaces 250, 252 of the surgical fastener 220 enable a plurality of surgical fasteners to be stacked one atop another with the flat major surfaces of adjacent surgical fasteners engaging one another within the stack. FIG. 20 shows a stack of three surgical fasteners 220A-220C. The bottom surgical fastener 220A in the stack has a flat top surface 250A and a flat bottom surface 252A. The flat bottom surface 252B of the second surgical fastener 220B in the stack is in contact with the flat top surface 250A of the first surgical fastener 220A. The flat bottom surface 252C of the third surgical fastener 220C in the stack is in contact with the flat top surface 250B of the second surgical fastener 220C. As shown in FIG. 20, the flat major surfaces of the respective surgical fasteners are in contact with one another for maintaining the respective surgical fasteners in the stacked array. Although FIG. 20 shows three stacked surgical fasteners 220A-2200, in other embodiments, the number of surgical fasteners in a stack may be five, 10, 20, 30, or more. In one embodiment, the surgical fasteners may be loaded into a cartridge 116 (FIG. 2A) to form a stack of deployable surgical fasteners.

Referring to FIGS. 21A-21D, in one embodiment, an insertion tool 260 is used for advancing surgical fasteners toward a distal end of an applicator instrument. In one embodiment, the insertion tool 260 preferably includes a proximal end 262 that may be coupled with a distal end of a flexible member 160 and a distal end 264 that is adapted to engage the proximal end of a surgical fastener. In one embodiment, the insertion tool 260 and the flexible member 160 are features on the same part.

Referring to FIGS. 19A, 19E, and 21A-21D, in one embodiment, the insertion tool 260 preferably includes opposing C-shaped projections 266A, 266B that oppose one another at the distal-most end of the insertion tool. In one embodiment, the C-shaped projections are designed to engage the C-shaped surfaces 240A, 240B of the bridge at the proximal end of the surgical fastener 220. In one embodiment, the insertion tool 260 includes a surface 268, such as a flat surface, adjacent the distal end of the insertion tool that is surrounded by the opposing C-shaped projections 266A, 266B. In one embodiment, the crown 242 at the proximal end of the surgical fastener is disposed within the space bounded by the C-shaped projections 266A, 266B. The distal surface 268 may or may not engage the center section 244 and the first and second laterally extending flanges 246A, 246B of the crown at the proximal end of a surgical fastener. In one embodiment, the center section 244 and laterally extending flanges 246A, 246B of the insertion control surface 242 has a height $H_1$ (FIG. 19C) and the C-shaped projections 266A, 266B have a height $H_2$ (measured from surface 68) that is greater than the height $H_1$ so that the distal surface 268 is spaced from the crown 242 when the C-shaped projections 266A, 266B engage the flat surfaces 240A, 240B. As a result, all of the insertion force transferred from the insertion tool 260 to the surgical fastener 220 is transferred via the C-shaped projections 266A, 266B of the insertion tool engaging the C-shaped surfaces 240A, 240B aligned with the proximal ends of the respective first and second legs 222A, 222B.

In one embodiment, the insertion tool 260 preferably includes a fin or stripper ramp 270 that extends above the C-shaped projections 66A, 66B at the distal end thereof. The stripper ramp 270 has a distal face 272 that lies in a plane with the distal faces 274A, 274B of the respective C-shaped projections 266A, 266B. In one embodiment, the insertion tool includes an attachment flange 275 at the proximal end 262 thereof that is coupled or attached with the distal end of a flexible member so that the insertion tool may move distally and proximally with the flexible member 160. The insertion tool may also be part of the flexible member.

In one embodiment, the insertion tool 260, coupled with the distal end of a flexible member 160 via the attachment flange 275, is advanced distally toward the trailing end of a surgical fastener whereupon the distal-most face 272 of the ramp 270 engages the crown 242 (FIG. 19B) at the proximal/trailing end of the surgical fastener. As the insertion tool advances distally, the proximal end of the surgical fastener is desirably directed into alignment with the major distal surface 268 at the distal end 264 of the insertion tool 260 so that the center section 244 and the first and second laterally extending flanges 246A, 246B (FIG. 19E) of the crown 242 are disposed between the opposing C-shaped projections 266A, 266B of the insertion tool 260.

Referring to FIGS. 21A-21D, in one embodiment, the insertion tool 260 has a flat top surface 290, a flat bottom surface 292, a first flat side surface 294A, and a second flat side surface 294B. As will be described in more detail herein, in one embodiment, the flat surfaces 290, 292, 294A, and 294B are used to control the orientation of the insertion tool 260 as it moves distally in an applicator instrument.

Figure 21A:
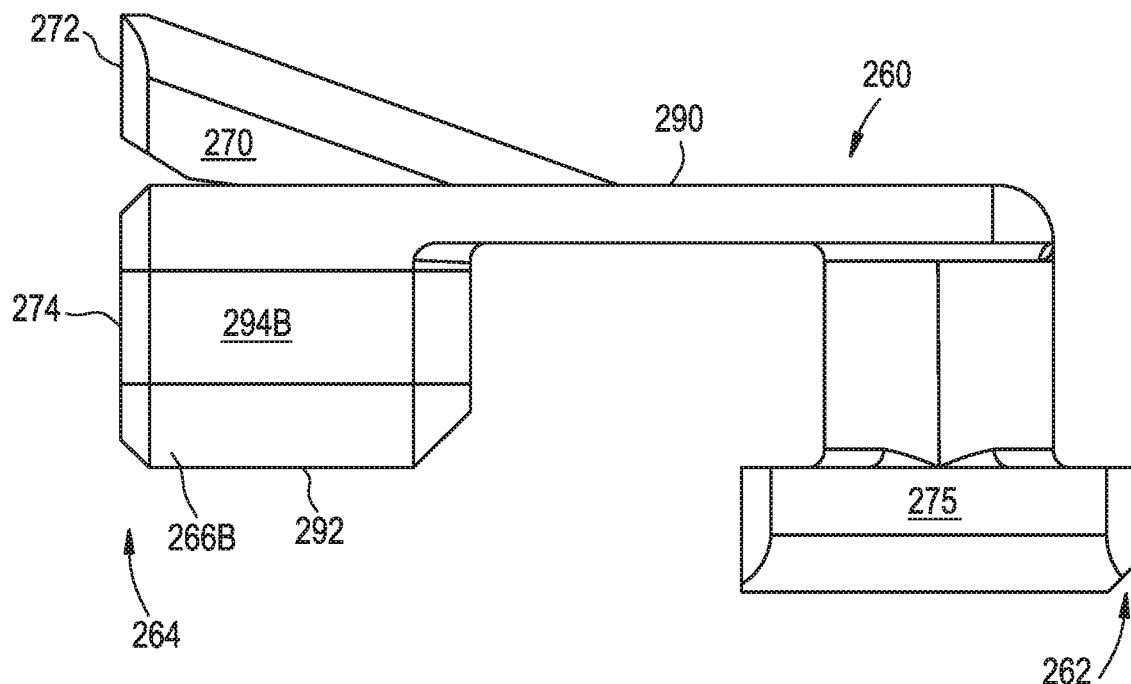
FIGS. 21A-21D show a pusher used to dispense the surgical fastener of FIGS. 17-17H from an applicator instrument, in accordance with one embodiment.
Figure 21B:
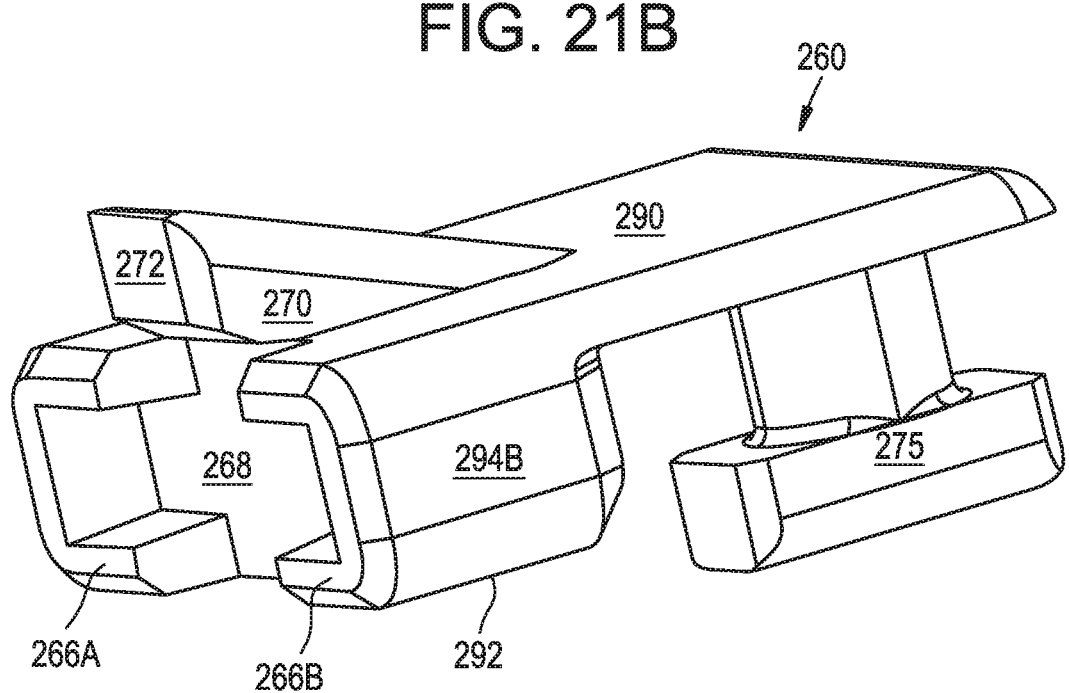
Figure 21C:
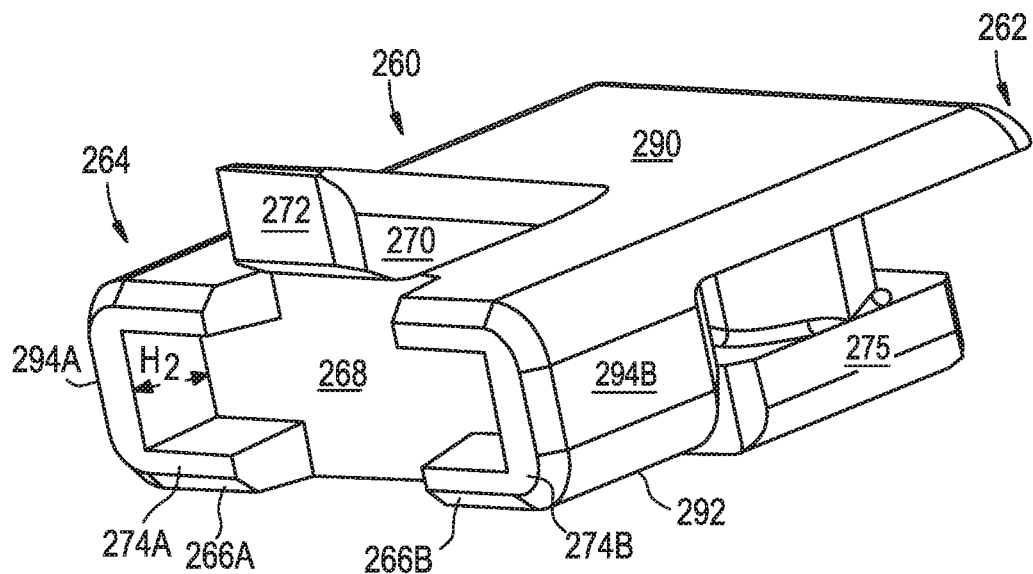
Figure 21D:
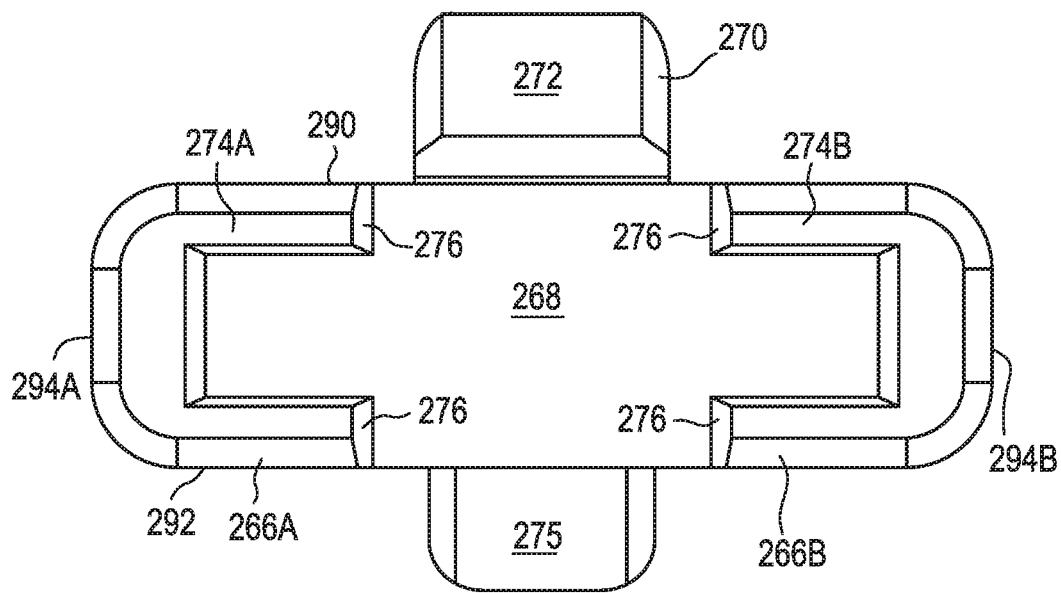
Figure 22A:
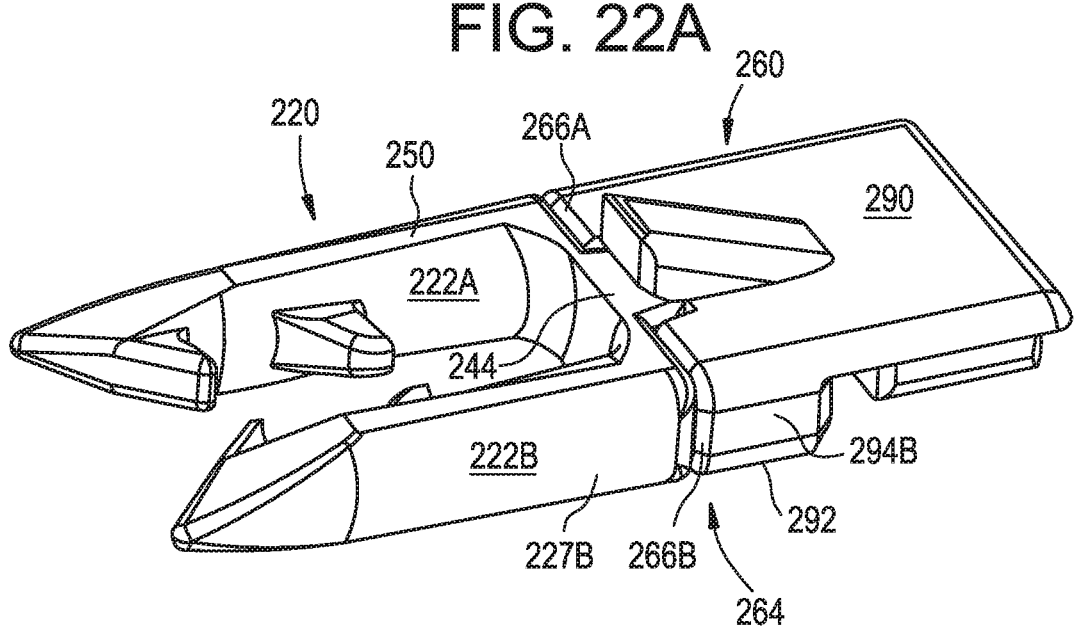
FIGS. 22A-22D show the pusher of FIGS. 19A-19D engaged with the surgical fastener of FIGS. 17A-17H.
Figure 22B:
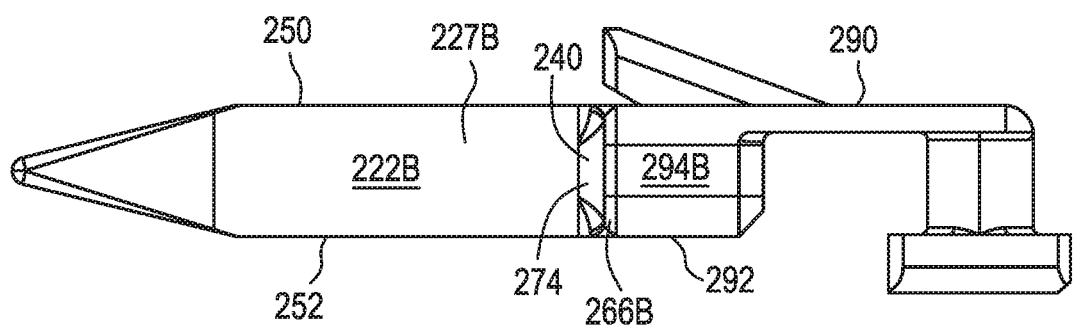
Figure 22C:
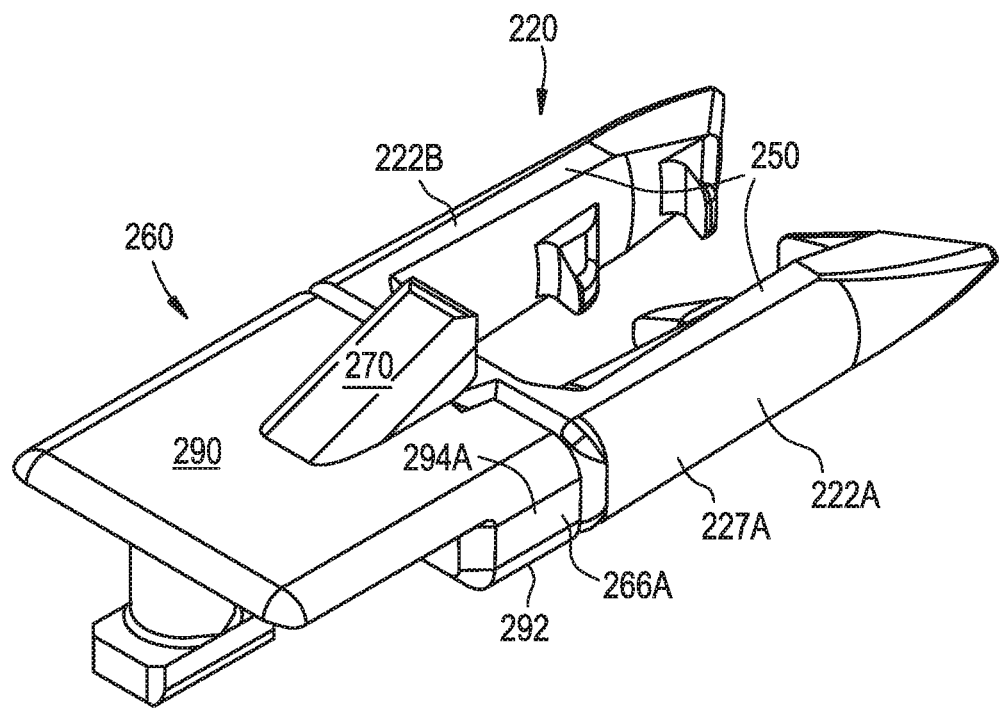
Figure 22D:
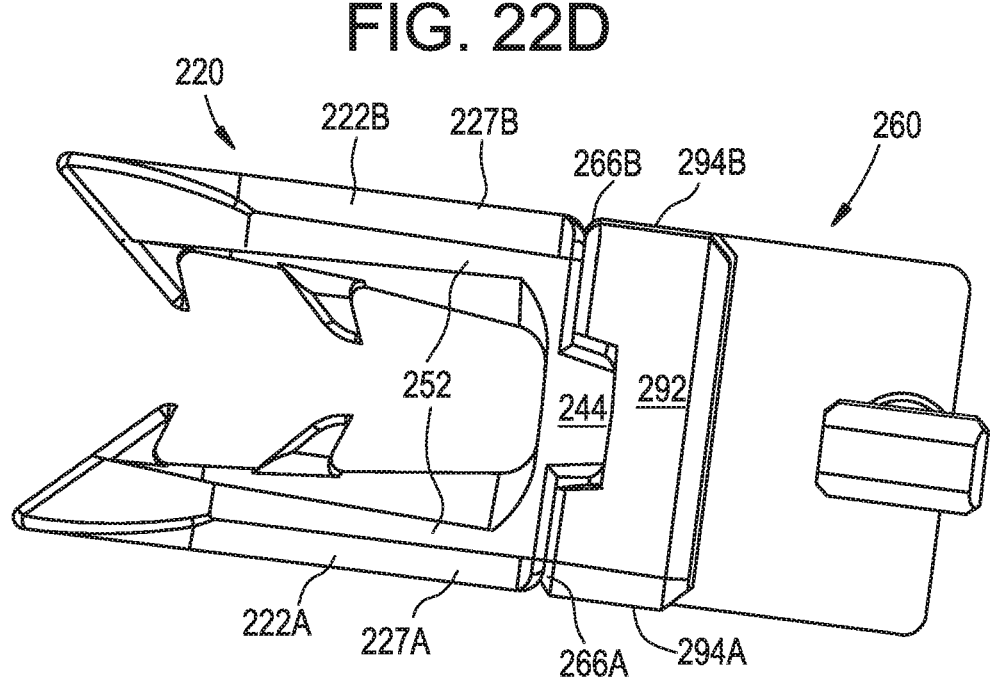

Referring to FIGS. 19E and 21D, in one embodiment, when the insertion tool engages the proximal end of the surgical fastener 220, the lateral side surfaces 246A, 246B of the center section 244 may engage the ends 276 of the opposing C-shaped projections 266A, 266B for further controlling the orientation of the surgical fastener as it is advanced distally by the insertion tool 260.

Referring to FIGS. 19D and 22A-22D, in one embodiment, the insertion tool 260 may be advanced until the distal end 264 of the insertion tool captures the crown 242 (FIG. 19B) located at the proximal end of the surgical fastener 220. In one embodiment, the center section 244 and the first and second laterally extending flanges 246A, 246B (FIG. 19B) of the crown 242 are captured between the first C-shaped projection 266A and the second C-shaped projection 266B at the distal end 264 of the insertion tool 260. The distal faces 274A, 274B of the C-shaped projections 266A, 266B preferably abut against the C-shaped surfaces 240A, 240B (FIG. 19E) provided at the proximal ends of the respective first and second legs 222A, 222B. In one embodiment, the C-shaped projections 266A, 266B have a height $H_2$ (FIG. 21C) that is greater than 0.020 inches so that the major distal surface 268 of the insertion tool 260 does not engage the crown 242 at the proximal end of the surgical fastener. As a result, all of the insertion force that is transferred from the insertion tool 260 to the surgical fastener 220 is transmitted via the C-shaped projections 266A, 266B engaging the C-shaped surfaces 240A, 240B aligned with the proximal ends of the first and second legs 222A, 222B.

Referring to FIGS. 22A-22D, in one embodiment, when the crown of the surgical fastener 220 is engaged by the distal end of the insertion tool 260, the flat top surface 290 of the insertion tool 260 is aligned with the flat top surface 250 of the surgical fastener 220, the flat bottom surface 292 of the insertion tool 260 is aligned with the flat bottom surface 252 of the surgical fastener 220, the first flat side surface 294A of the insertion tool 260 is aligned with the flat side surface 227A of the first leg 222A of the surgical fastener 220, and the second flat side surface 294B of the insertion tool 260 is aligned with the flat side surface 227B of the second leg 222B of the surgical fastener 220.

Figure 23:
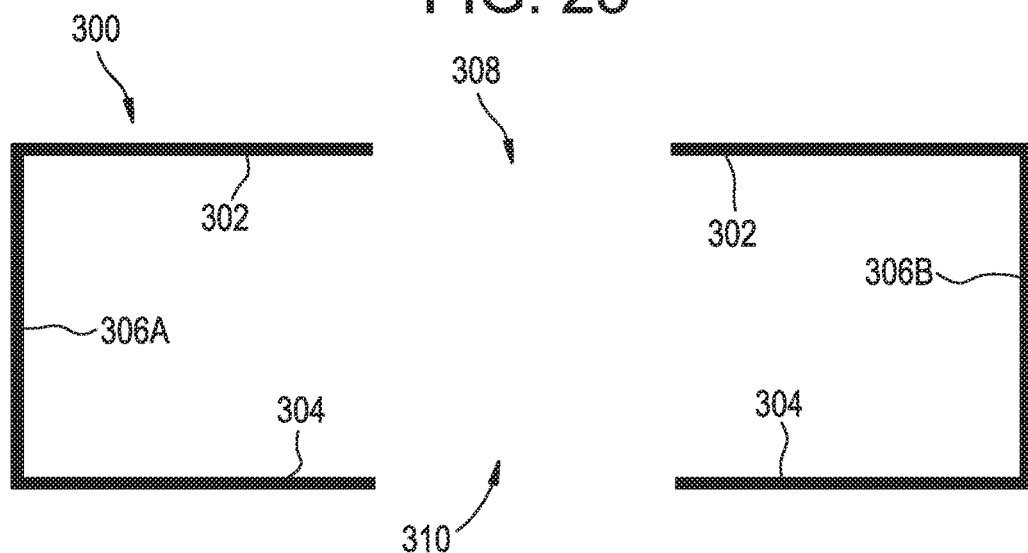
FIGS. 23 and 24 show a method of guiding a surgical fastener and a pusher through a channel of an elongated shaft of an applicator instrument, in accordance with one embodiment of the present patent application.

Referring to FIG. 23, in one embodiment, an applicator instrument for dispensing surgical fasteners preferably has an elongated shaft 102 (FIG. 1A) with an elongated conduit 300 for guiding a surgical fastener and an insertion tool joined with the surgical fastener toward the distal end of the elongated shaft. In one embodiment, the elongated conduit 300 preferably includes a top wall 302, a bottom wall 304, and side walls 306A, 306B that extend between the top wall and the bottom wall. The top wall 302 of the elongated conduit 300 has an elongated top notch 308 formed therein and the bottom wall 304 has an elongated bottom notch 310 formed therein. In one embodiment, the elongated top and bottom notches 308, 310 oppose one another and are in alignment with one another.

Figure 24:
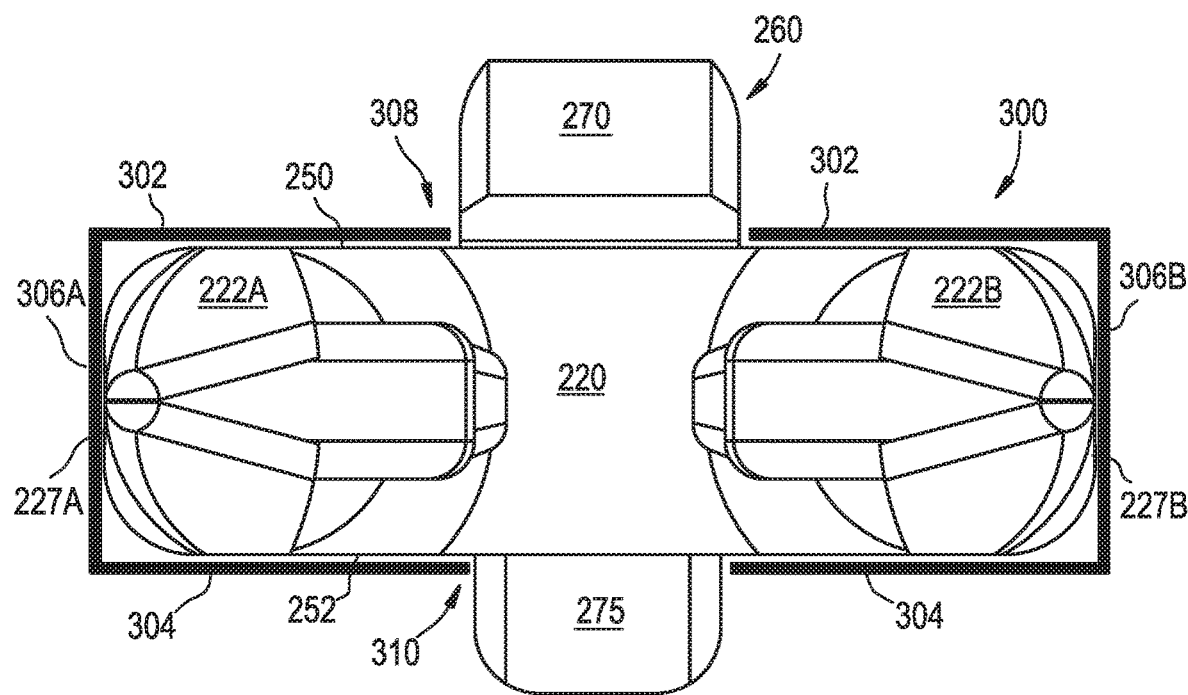

Referring to FIG. 24, in one embodiment, the distal end of the insertion tool 260 engages the proximal end of the surgical fastener 220 for advancing/pushing the surgical fastener toward the distal end of the elongated shaft of the applicator instrument. In one embodiment, the flat top surface 250 of the surgical fastener 220 and the flat top surface 290 (FIG. 21A) of the insertion tool 260 are opposed by the top wall 302 of the elongated conduit 300, and the flat bottom surface 252 of the surgical fastener 220 and the flat bottom surface 292 (FIG. 21A) of the insertion tool 260 are opposed by the bottom wall 304 of the elongated conduit 300. In addition, the flat side surface 227A of the first leg 222A of the surgical fastener 220 and the first flat side surface 294A (FIG. 22C) of the insertion tool 260 are opposed by the first side wall 306A of the elongated conduit 300, and the flat side surface 227B of the second leg 222B of the surgical fastener 220 and the second flat side surface 294B (FIG. 22D) of the insertion tool 260 are opposed by the second side wall 306B of the elongated conduit 300. The opposing top wall 302, bottom wall 304, and side walls 306A, 306B preferably guide and control the orientation of the surgical fastener 220 and the insertion tool 260 as the joined elements are driven distally through the elongated conduit 300.

In one embodiment, as the insertion tool 260 moves distally through the elongated conduit 300, the stripper ramp 270 slides through the elongated top notch 308 in the top wall 302 of the elongated conduit 300 and the attachment flange 275 slides through the elongated bottom notch 310 in the bottom wall 304 of the elongated conduit 300. The registration of the stripper ramp 270 with the elongated top notch 308 and the attachment flange 275 with the elongated bottom notch 310 preferably provides further control over the orientation and stability of the surgical fastener 220 and insertion tool 260 as the joined elements move distally through the elongated conduit 300.

Figure 25A:
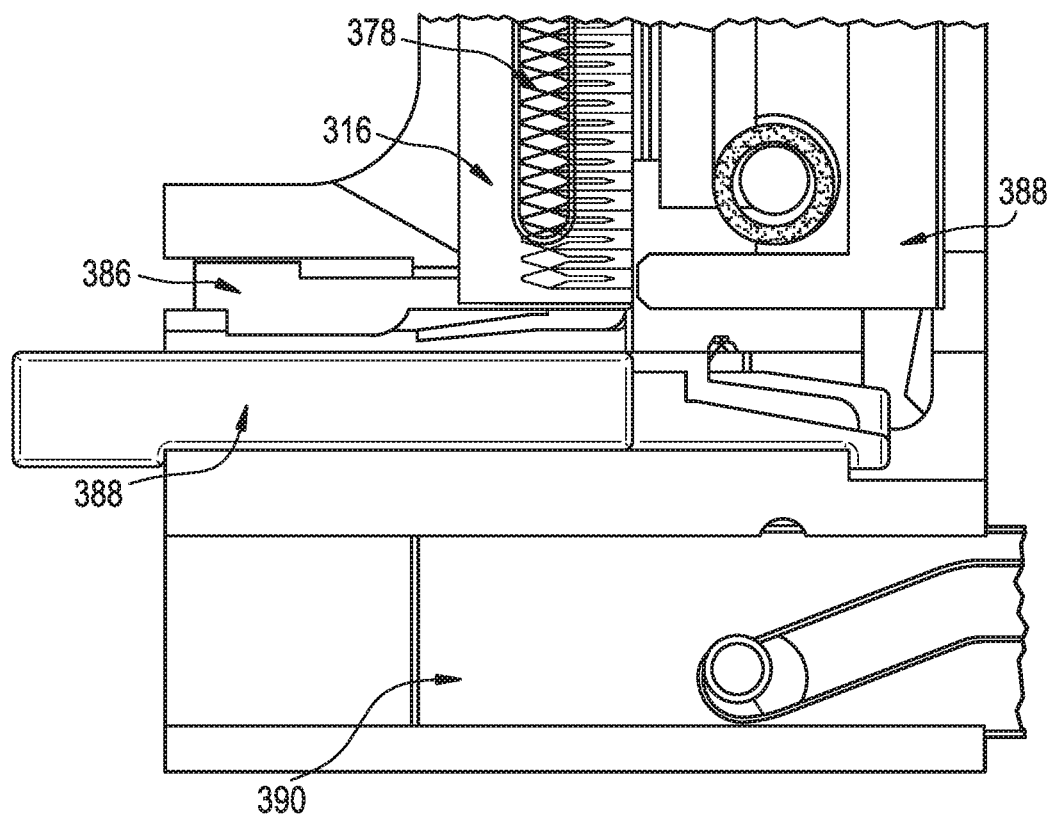
FIGS. 25A-25D show a cartridge system of an applicator instrument having an elevator for aligning a surgical fastener with a distal end of a flexible member, in accordance with one embodiment of the present patent application.
Figure 25B:
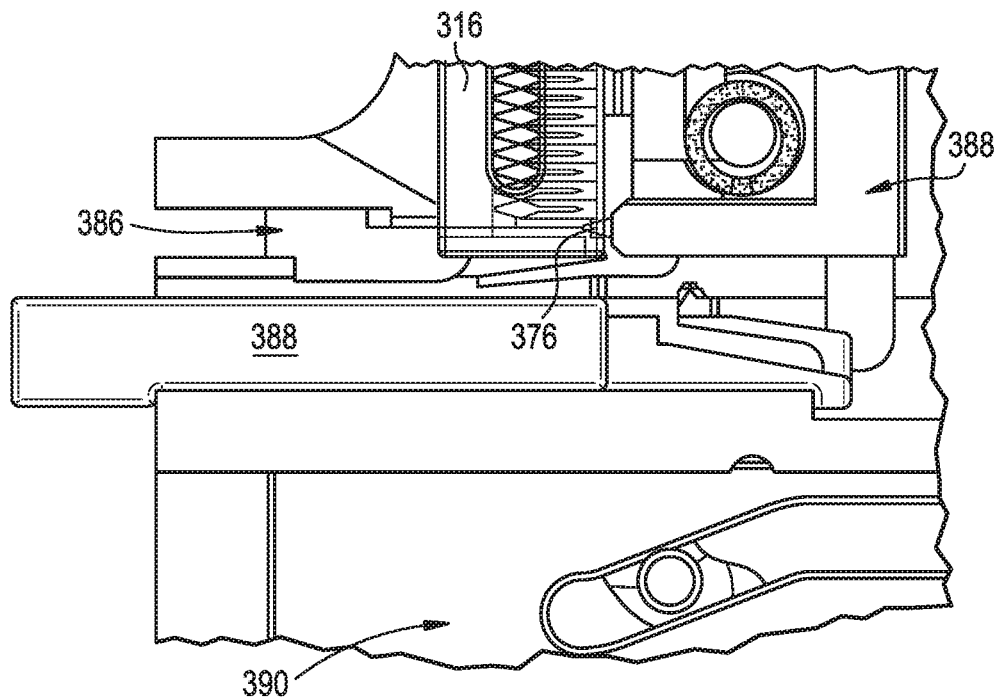

Referring to FIG. 25A, in one embodiment, an applicator instrument for dispensing surgical fasteners preferably includes a cartridge system 316 that utilizes a single linear path to strip a surgical fastener from the bottom of a surgical fastener stack and place the stripped surgical fastener into alignment with a distal end of a flexible member for dispensing the surgical fastener from the distal end of an elongated shaft. In one embodiment, prior to commencing a firing cycle, a surgical fastener stack 378 is arrayed within the cartridge 316. A pusher 386 is located distal to the surgical fastener stack 378. In one embodiment, an elevator 388 is aligned with a lower end of the cartridge 316. The cartridge system includes a slide 390 that is in a proximal-most position. Referring to FIG. 25B, in one embodiment, when a user squeezes the trigger of the applicator instrument, the slide 390 moves the pusher 386 proximally for pushing the lower-most surgical fastener 376 out of the cartridge 316 and into the elevator 388.

Figure 25C:
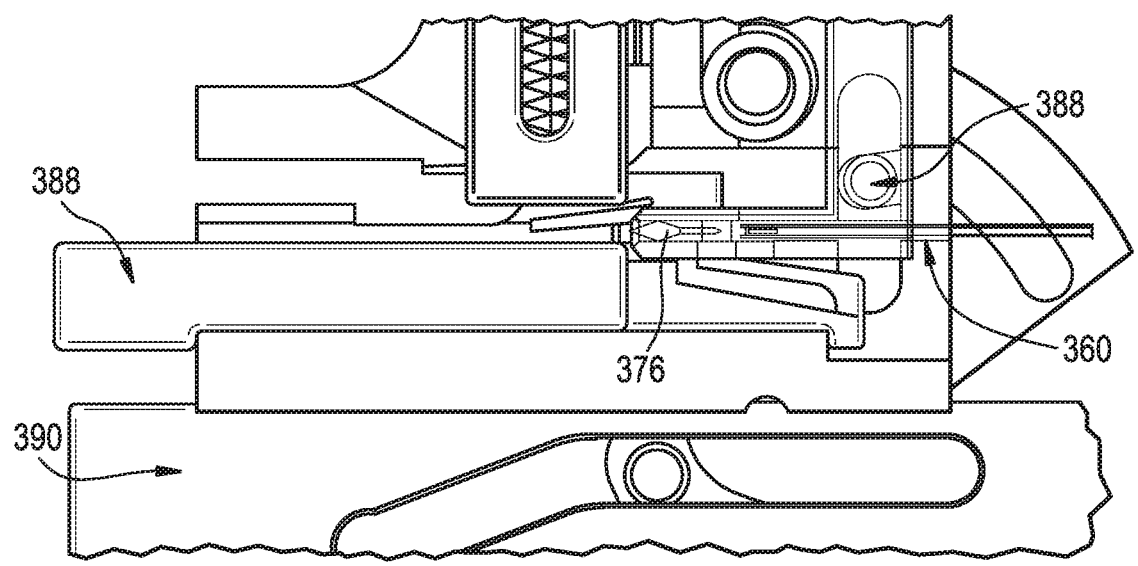

Referring to FIG. 25C, as the user finishes squeezing the trigger, the pusher 386 stops moving proximally once the lower-most surgical fastener 376 is fully inside the elevator 388. The elevator 388 moves down so that the surgical fastener 376 is aligned with the distal end of the flexible member 360. During this stage, the slide 390 moves proximally from the position shown in FIG. 25B.

Figure 25D:
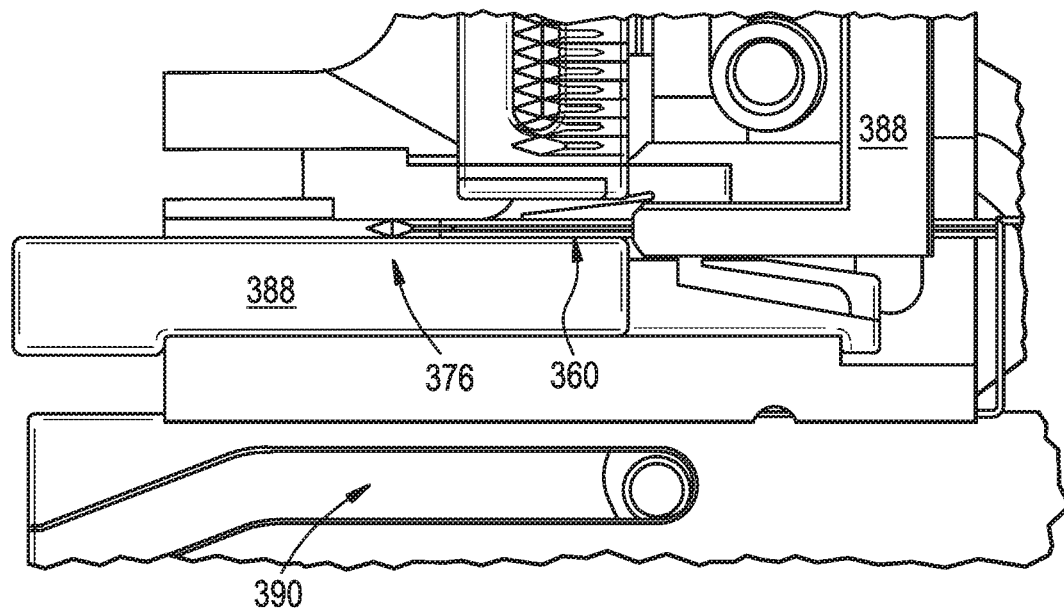

Referring to FIG. 25D, when the applicator instrument fires, the slide 390 has moved all the way to the left and the elevator 388 is all the way down. The flexible member 360 moves along the lower guide 396 for advancing the surgical fastener 376 toward the distal end of the elongated shaft.

Figure 26A:
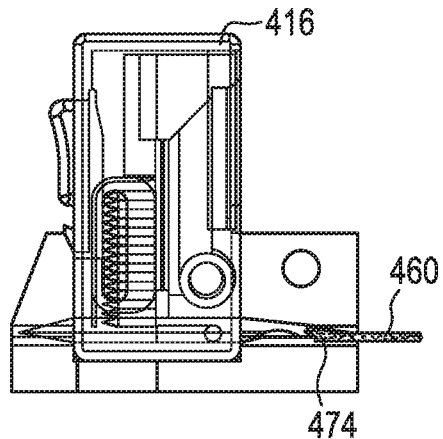
Figure 26B:
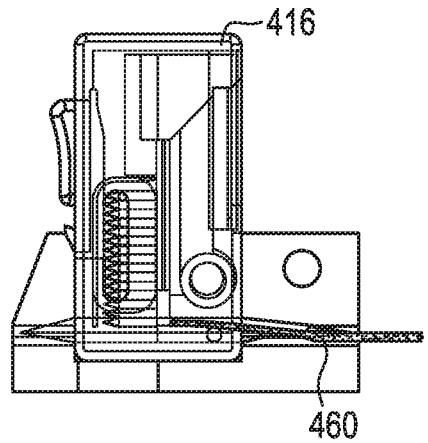
Figures 1, 26B:
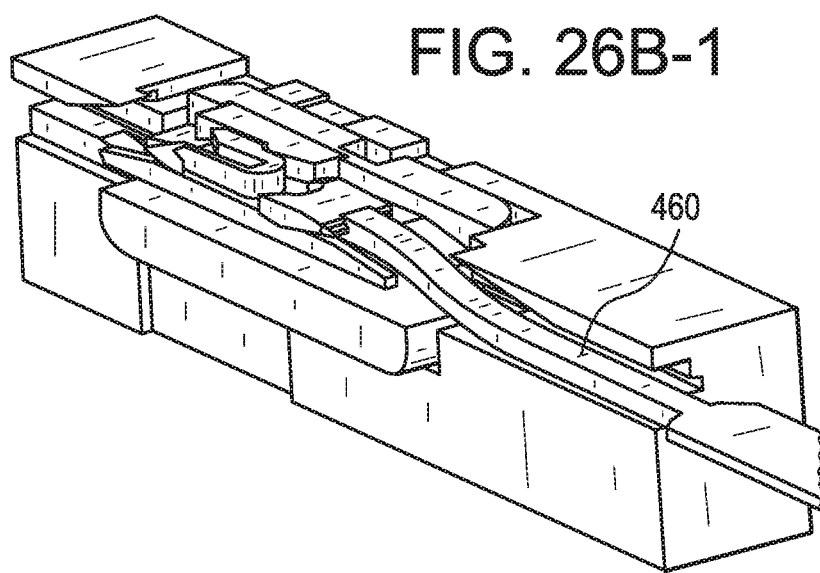
Figure 26C:
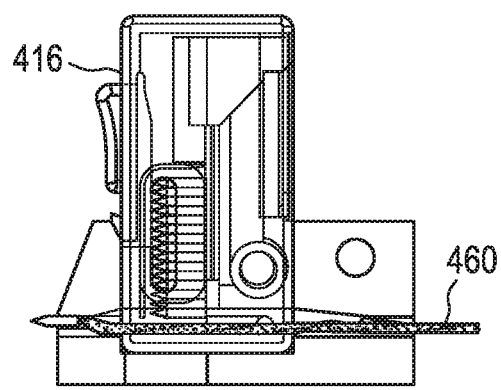

Referring to FIGS. 26A-26B, 26B-1, and 26C, in one embodiment, an applicator instrument includes a cartridge system 416 and a firing system that has one path to strip a surgical fastener from a bottom of a surgical fastener stack during the insertion motion and a different path to follow on the retraction of the flexible member 460. Referring to FIG. 26B-1, in one embodiment, the cartridge system and the firing system utilize a racetrack arrangement 465 for providing the first path for distal movement of the flexible member 460 and the second path on the return, proximal motion of the flexible member. In one embodiment, the leading end 460A of the flexible member 460 is wider to engage with the upper path and a thinner section 460B of the flexible member 460 just proximal to the leading end 460A is thinner to allow the flexible member to pass between the first and second paths of the racetrack arrangement 465.

Figure 27A:
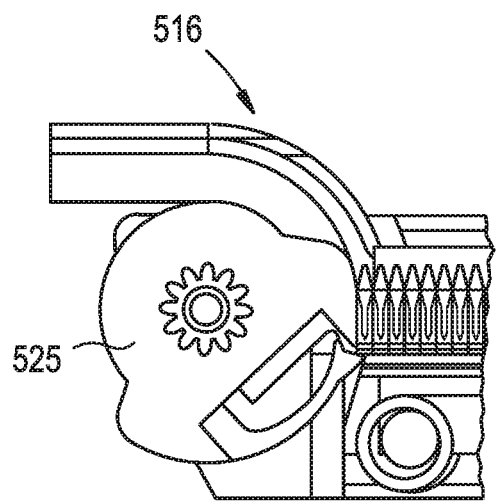
FIGS. 27A-27C show a cartridge system of an applicator instrument having a rotary element, in accordance with one embodiment of the present patent application.
Figure 27B:
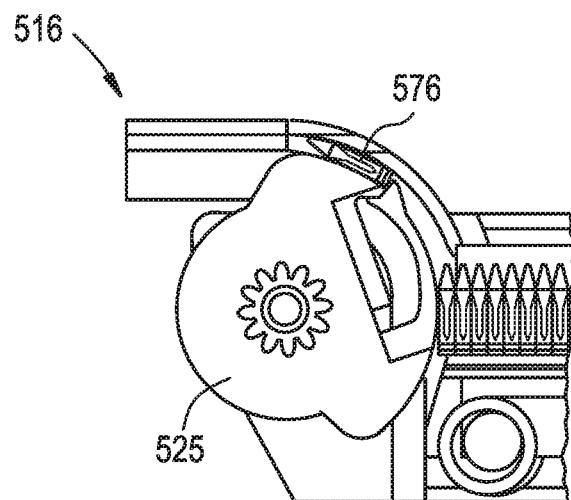
Figure 27C:
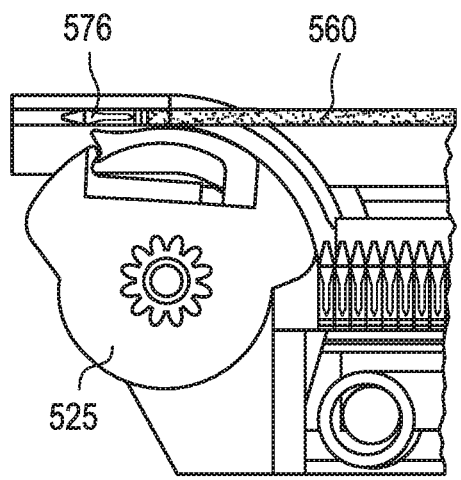

Referring to FIGS. 27A-27C, in one embodiment, an applicator instrument utilizes a cartridge system 516 having a rotary motion member 525 to strip a surgical fastener and place the stripped surgical fastener into proper alignment with a distal end of a flexible member 560 for advancement toward the distal end of an elongated shaft. Providing a cartridge system 516 with rotary motion member 525 enables tissue fasteners to be stacked in the cartridge in any orientation relative to the motion of the flexible member 560. The rotary motion member preferably rotates the surgical fasteners 576 through any angle necessary to bring the surgical fasteners in line with the distal end of the flexible member 560 (90 degree rotation for example).

Figure 28A:
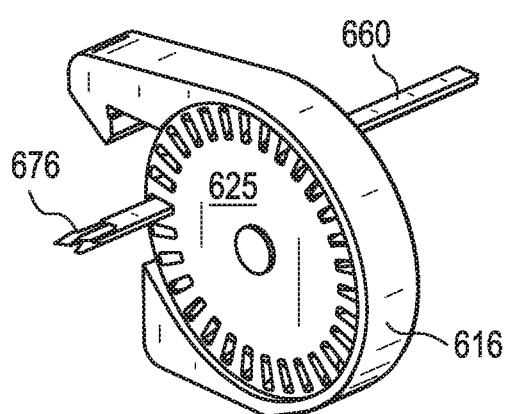
FIGS. 28A-28B show a side loaded cartridge system of an applicator instrument having a rotary drum, in accordance with one embodiment of the present patent application.
Figure 28B:
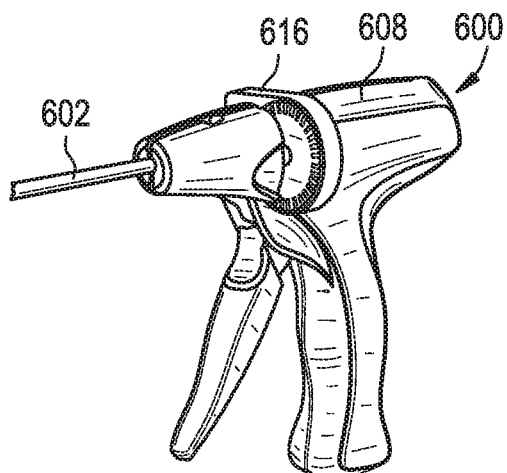

Referring to FIGS. 28A and 28B, in one embodiment, the cartridge system 616 includes a rotary drum 625 containing a plurality of surgical fasteners 676. The cartridge 616 may be side loading for mounting onto the side of a housing 608 of an applicator instrument 600. In one embodiment, a distal end of a flexible member 660 passes through an opening in the rotary drum 625 that contains a surgical fastener 676 for advancing the surgical fastener toward a distal end of an elongated shaft. In one embodiment, movement of the trigger rotates the cartridge 616 to present the next surgical fastener for insertion.

Figure 29A:
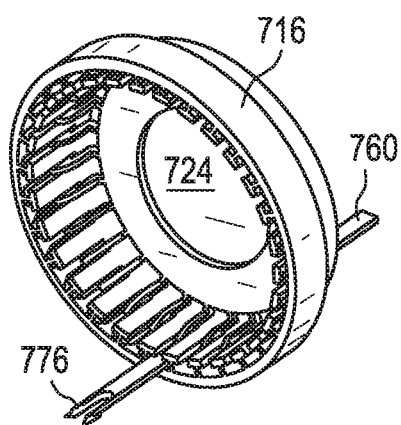
FIGS. 29A-29B show a top loaded cartridge system of an applicator instrument having a rotary drum, in accordance with one embodiment of the present patent application.
Figure 29B:
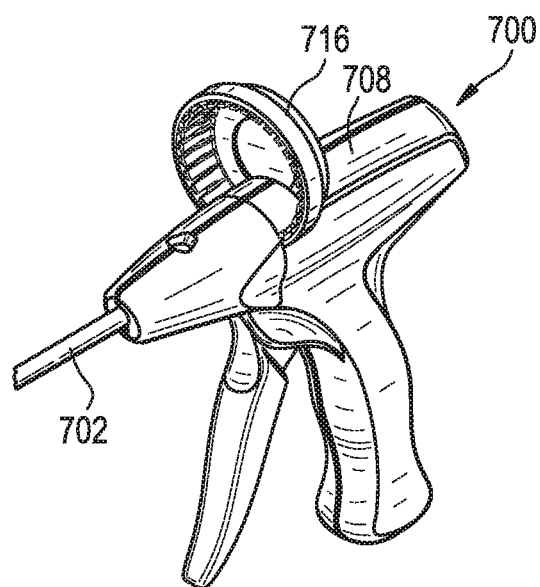
Figure 30A:
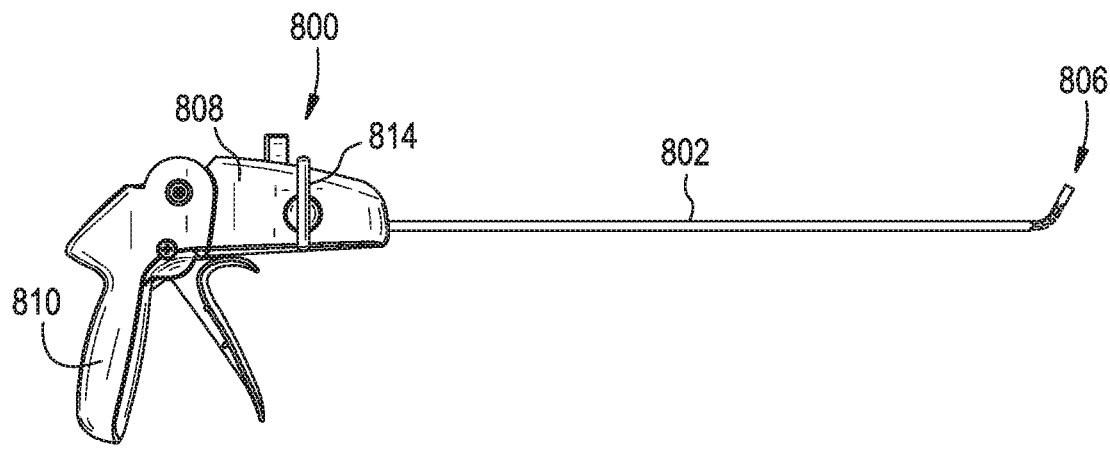
FIG. 30A shows the applicator instrument of FIG. 1A with the reconfigurable handle in the pistol configuration and the distal end of the elongated shaft in an articulated configuration.
Figure 30B:
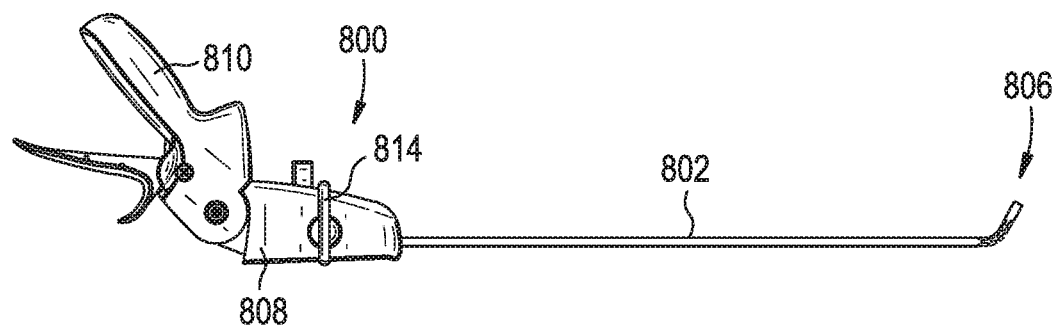
FIG. 30B shows the applicator instrument of FIG. 1B with the reconfigurable handle in the in-line configuration and the distal end of the elongated shaft in an articulated configuration.

Referring to FIGS. 29A and 29B, in one embodiment, a cartridge 716 with a rotatory drum may be top mounted onto the housing 708 of an applicator instrument 700. The distal end of a flexible member 760 advances through the rotatory drum 725 for engaging a surgical fastener 776 for being dispensed from a distal end of an elongated shaft 702. In one embodiment, movement of the trigger rotates the cartridge 716 to present the next surgical fastener for insertion Referring to FIGS. 30A and 30B, in one embodiment, an applicator instrument 800 having one or more of the features disclosed herein includes an elongated shaft 802 having an articulating distal end 806. The applicator instrument 800 includes a housing 808 and a handle 810 coupled with the housing. The handle 810 may be reconfigured between the pistol configuration shown in FIG. 30A and the in-line configuration shown in FIG. 30B, as described in detail herein. The applicator instrument 800 preferably includes an articulation lever 814 provided on the housing 808 that may be moved between a horizontal configuration for straightening the distal end 806 of the elongated shaft 802 and a vertical orientation for articulating the distal end 806 of the elongated shaft 802. The elongated shaft 802 may be articulated with the applicator instrument in either the pistol grip configuration of FIG. 30A, the in-line configuration of FIG. 30B, or numerous positions therebetween.

Figure 31A:
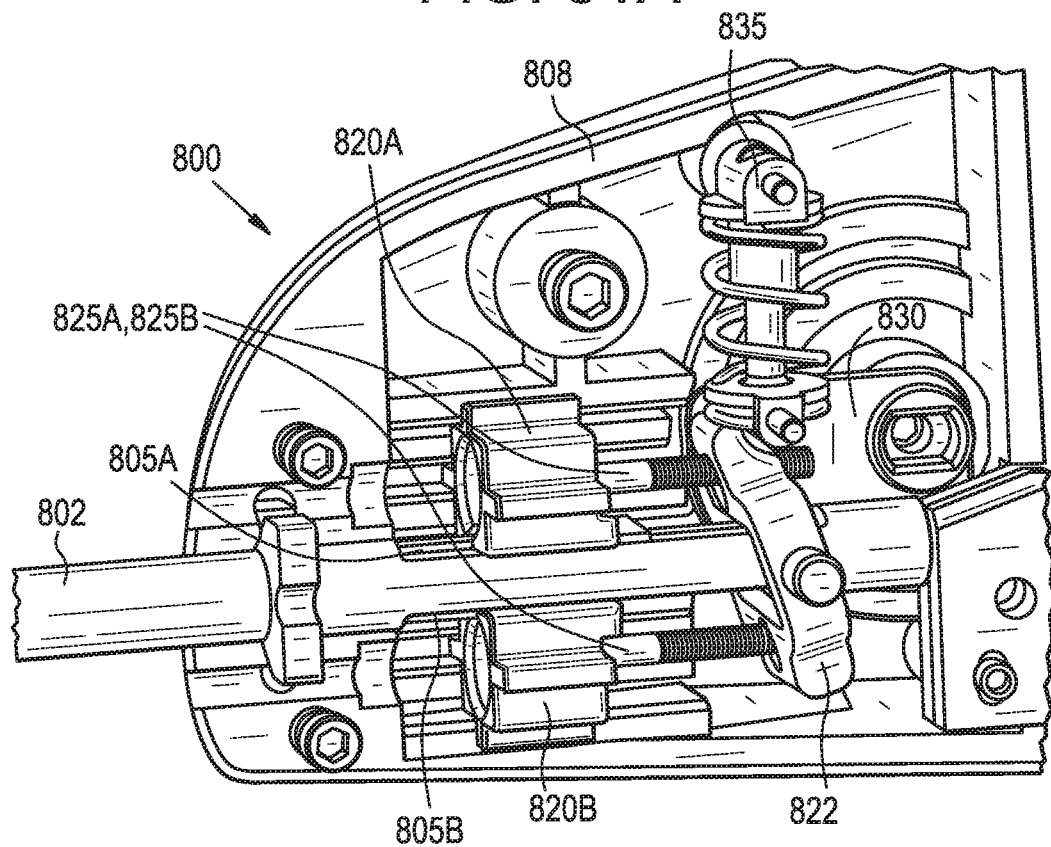
FIG. 31A shows an applicator instrument for dispensing surgical fasteners having an articulation system for articulating a distal end of an elongated shaft, in accordance with one embodiment of the present patent application.

Referring to FIG. 31A, in one embodiment, the applicator instrument 800 preferably includes a housing 808 and an elongated shaft 802 projecting from a distal end of the housing 808. In one embodiment, the applicator instrument 800 includes an upper articulation band 805A and a lower articulation band 805B that are coupled with an articulating member 815 (FIG. 31B) located at the distal end 806 of the elongated shaft 802.

The articulation system preferably includes an upper slider 820A that is positioned over the top of the elongated shaft 802 and a lower slider 820B that is positioned below the elongated shaft. The upper slider 820A is attached to the proximal end of the upper articulation band 805A and the lower slider 820B is attached to the proximal end of the lower articulation band 805B. The articulation system includes a yoke 822 that is coupled with the upper and lower sliders 820A, 820B. In one embodiment, the yoke 822 is capable of rotating relative to the longitudinal axis of the elongated shaft 802. An upper tension adjustment screw 825A preferably connects the upper slider 820A with an upper end of the yoke 822 and a lower tension adjustment screw 825B preferably connects the lower slider 820B with a lower end of the rotatable yoke 822.

In one embodiment, the articulation system includes a cam plate 830 that is rotated by the articulation lever 814 (FIG. 30B) for moving the cam plate between a horizontal configuration associated with a straight elongated shaft and a vertical orientation associated with a fully articulated elongated shaft. The articulation system includes an over-center assembly 835 coupled with the distal end of the cam plate 830 for forcing the cam plate 830 into one of two positions, namely, the horizontal configuration associated with a straight elongated shaft and a vertical orientation associated with a fully articulated elongated shaft. If the cam plate 830 is at an intermediate position between a horizontal orientation and a vertical orientation, the over-center assembly 835 desirably forces the cam plate 830 to rotate into either the horizontal orientation or the vertical orientation. The mechanism to provide this force is a compression spring constrained between two struts. The upper strut is pivotally attached to the housing 808 and the lower strut is pivotally attached to the cam plate 830. Rotating the cam plate 830 changes the force installed in the compression spring.

Figure 31B:
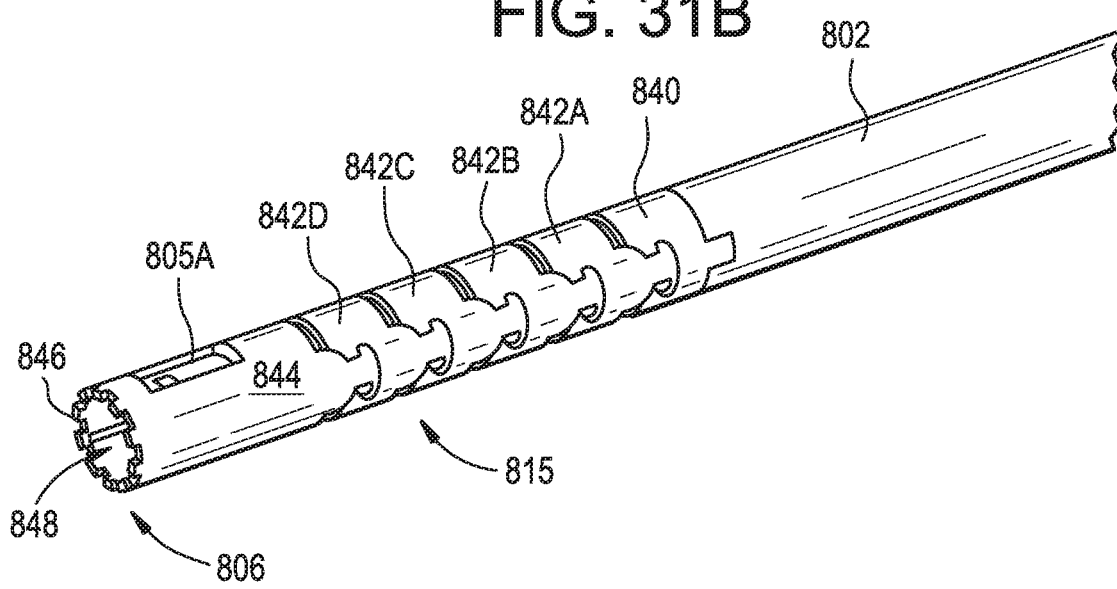
FIG. 31B shows a distal end of an elongated shaft having an articulating member with links capable of pivoting relative to one another, the articulating member being in a straight configuration, in accordance with one embodiment of the present patent application.

Referring to FIGS. 31A and 31B, in one embodiment, the upper and lower articulation bands 805A, 805B extend to the articulation member 815 at the distal end 806 of the elongated shaft 802. In one embodiment, the articulation member 815 includes a plurality of articulating segments or links that are coupled together at the distal end 806 of the elongated shaft 802, and that are adapted to pivot relative to one another. In one embodiment, the articulating member 815 includes a proximal articulation segment 840 attached to a distal end of the elongated shaft 802, a plurality of intermediate articulating segments 842A-842D, and a distal articulating segment 844 that extends to a distal-most end 806 of the elongated shaft 802. In one embodiment, a distal end face of the distal articulating segment 844 preferably has castling 846 or projections formed thereon for engaging an opposing surface such as a surgical mesh positioned over tissue. The distal-most end of the distal articulating segment 844 has an opening 848 for dispensing a surgical fastener through the opening. The upper and lower articulating bands 805A, 805B desirably pass through the elongated shaft 802, the proximal articulating segment 840, and the intermediate articulating segments 842A-842D for being affixed to respective upper and lower portions of the distal articulating segment 844.

Figure 32A:
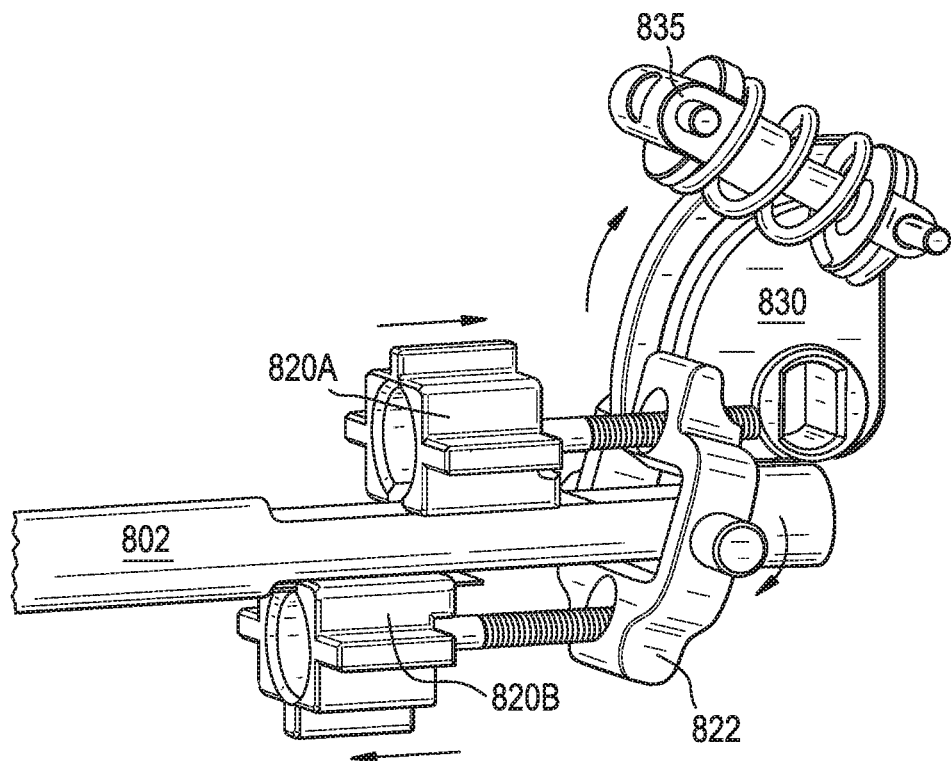
FIG. 32A shows the articulation system of FIG. 31A with a cam plate rotated into a second position for articulating the distal end of the elongated shaft of FIG. 31B.
Figure 32B:
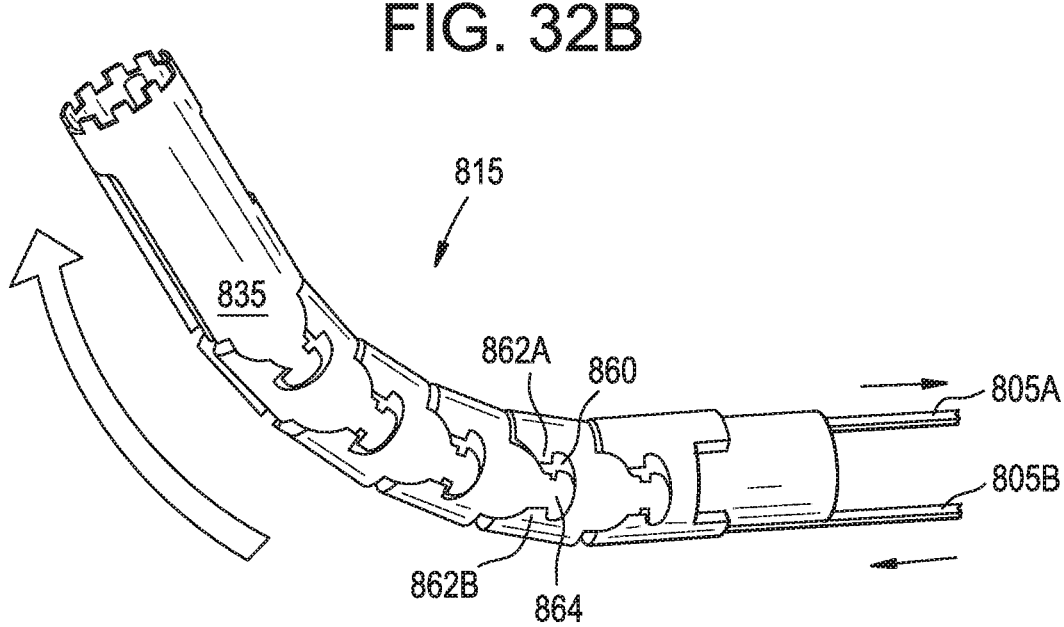
FIG. 32B shows the distal end of the elongated shaft of FIG. 31B with the articulating member in a fully articulated configuration.

Referring to FIGS. 32A and 32B, in one embodiment, when the articulation lever 814 (FIGS. 30A and 30B) is moved into the vertical orientation, the cam plate 830 rotates in a counterclockwise direction whereupon it is urged by the over-center system 835 to remain in the vertical orientation. The rotation of the cam plate 830, in turn, causes clockwise rotation of the yoke 822, which causes the upper slider 820A to move proximally and the lower slider 820B to move distally. As the sliders 820A, 820B move, tension is increased in the upper articulation band 805A while enabling the lower articulation band 805B to move distally. As a result of increasing the tension on the upper articulation band 805A while enabling lower articulation band 805B to move distally, the distal articulating segment 844 moves into the articulated configuration shown in FIG. 32B. For example, a minimum differential band tension is needed to provide a resistance to 2.0-2.5 lbs applied radially to the distal end 806 of the elongated shaft 802. This amount of resistance ensures that the distal end of the instrument is sufficiently stiff to accommodate the needs of hernia repair procedures, including mesh manipulation and firing of the applicator.

Figure 33A:
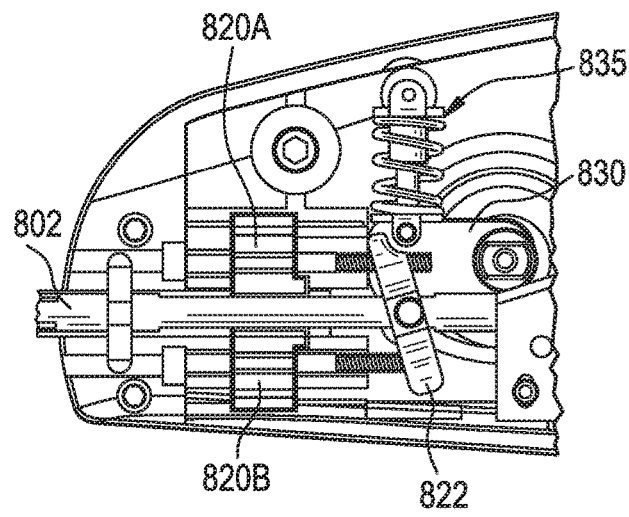
FIGS. 33A-33C show an applicator instrument having an articulation system and a distal end of an elongated shaft being in a straight configuration, in accordance with one embodiment of the present patent application.
Figure 33B:
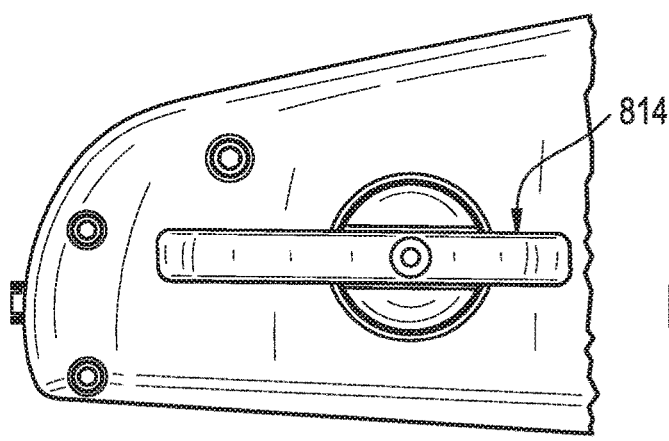
Figure 33C:
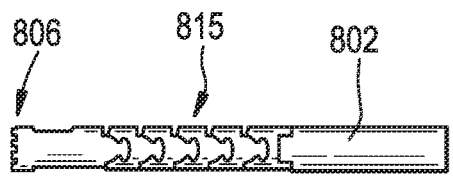

Referring to FIGS. 33A-33C, in one embodiment, the articulation control lever 814 is in a horizontal configuration so that the cam plate 830 has a horizontal orientation and the over-center spring 835 urges the cam plate 830 to remain in the horizontal orientation. With the articulation control lever 814 in the horizontal orientation, the upper slider 820A and the lower slider 820B are in alignment with one another along the length of the elongated shaft 802, and the rotatable yoke 822 has an upper end that is distal to a lower end thereof. With the articulation control lever 814 in the horizontal orientation, the upper articulation band 805A experiences little or no tension compared to the lower articulation band 805B so that the articulation member 814 at the distal end 806 of the elongated shaft 802 is in a straight configuration.

Figure 34A:
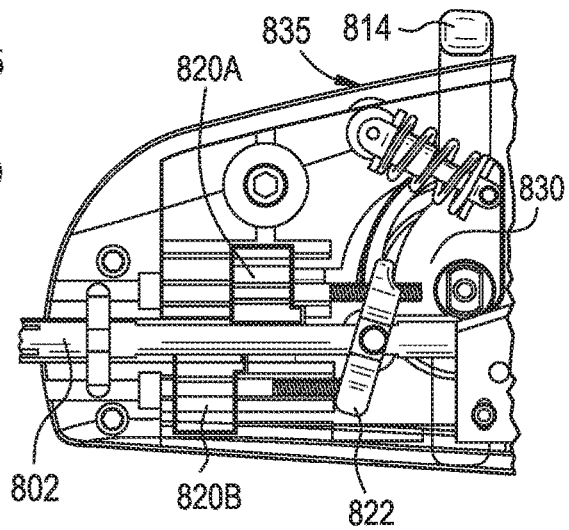
FIGS. 34A-34C show the applicator instrument of FIGS. 33A-33C with the elongated shaft being in a fully articulated configuration.
Figure 34B:
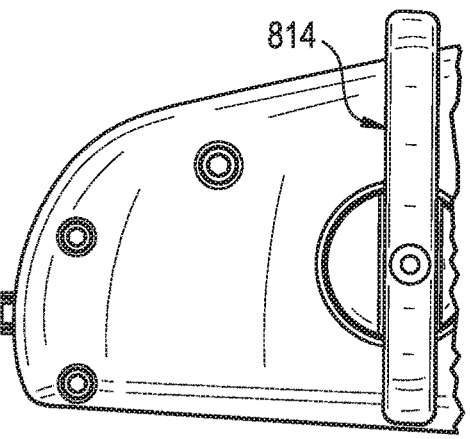
Figure 34C:
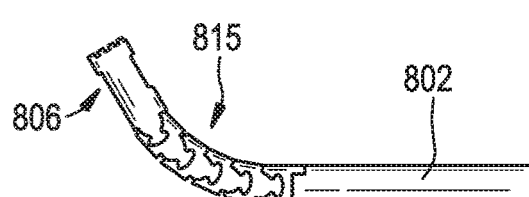

Referring to FIGS. 34A-34C, in on embodiment, when the articulation control lever 814 is rotated into a vertical orientation, the cam plate 830 is also in a vertical orientation and the over-center spring 835 urges the cam plate 830 to remain in the vertical orientation. As the cam plate rotates from the horizontal orientation (FIG. 33A) to the vertical orientation shown in FIG. 34A, the rotatable yoke 822 rotates in a clockwise direction so that the upper end of the yoke 822 is proximal to the lower end of the yoke. As a result, the upper slider 820A moves proximally for tensioning the upper articulation band and the lower slider 820B moves distally for providing little or no tension on the lower articulation band, compared to the upper articulation band. Referring to FIG. 34E, the tension on the upper articulation band articulates the articulation assembly 815 at the distal end 806 of the elongated shaft 802.

Figure 35:
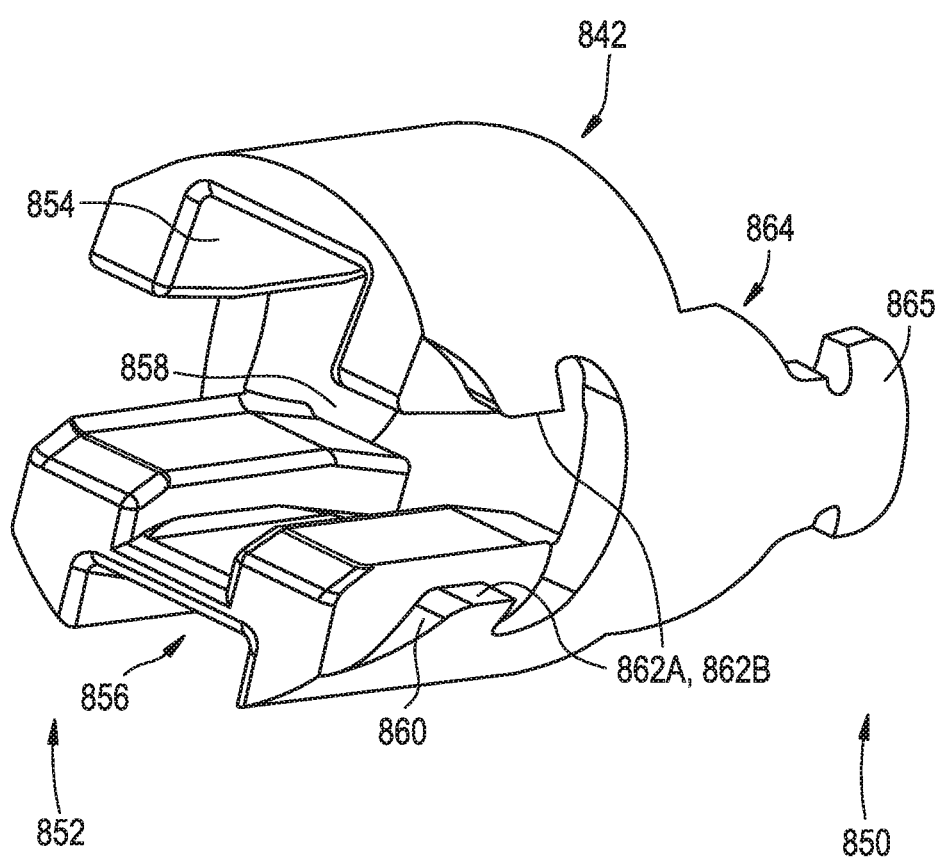
FIG. 35 shows a perspective view of an intermediate link of the articulation member of FIG. 31B.

Referring to FIG. 35, in one embodiment, an intermediate articulating segment 842 preferably has a proximal end 850 and a distal end 852. The intermediate articulating segment 842 desirably has an upper channel 854 adapted to enable the upper articulating band 805A (FIG. 31A) to pass therethrough and a lower channel 856 adapted to enable the lower articulation band 805B (FIG. 31A) to pass therethrough. The intermediate articulating segment 842 also desirably includes a central passageway 858 through which a surgical fastener and the distal end of the flexible member 160 may pass for pushing a surgical fastener toward the distal end of the elongated shaft.

In one embodiment, each lateral side of the intermediate articulating member 842 has a cylindrical pocket 860 that enables adjacent articulating segments to mesh with and pivot relative to one another. In one embodiment, the cylindrical pocket 860 includes upper and lower wings 862A, 862B that control the pivoting range of an adjacent articulating member.

In one embodiment, the proximal end of the intermediate articulating segment 842 has a cylindrical shaped projection 864 with a T-shaped head 865 that is adapted to be seated within the cylindrical pocket 860 of an adjacent articulating segment. When the projection 864 is inserted into a pocket 860 of an adjacent segment, the T-shaped head 865 is seated in a concave gap 861 of the pocket 860 and the wings 862A, 862B limit the pivoting movement of the adjacent articulating segments relative to one another.

FIG. 32B shows how the projection 864 of a distal segment fits within the cylindrical pocket 860 of a proximal segment whereupon the segments may pivot relative to one another, with the degree of pivoting controlled by the upper and lower wings 862A, 862B. Additionally, the T-shaped head on the projection 864 engages with the wings to prevent the segments from separating from each other, especially when external stresses are applied to the distal end of the elongated shaft.

Figure 36:
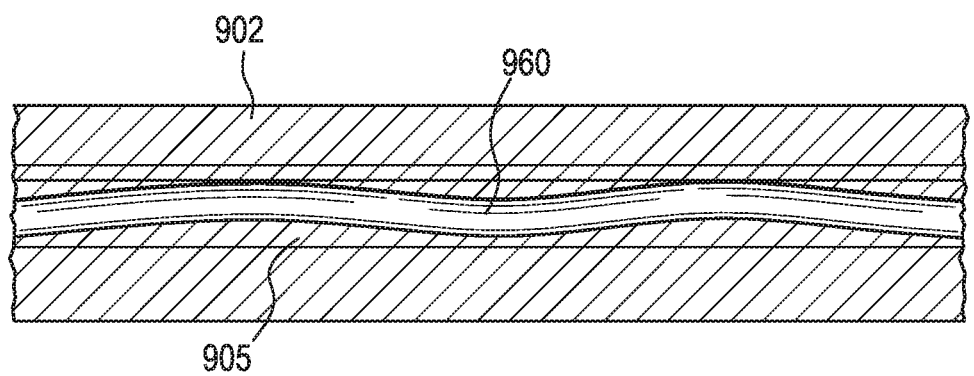
FIG. 36 shows a cross-sectional view of an elongated shaft and a flexible member disposed within an elongated conduit of the elongated shaft, buckled under compressive load.

Referring to FIG. 36, in one embodiment, an applicator instrument includes an elongated shaft 902 with a conduit 905 extending therethrough that is adapted to receive a flexible member 960 as the flexible member moves toward the distal end of the elongated shaft 902 for dispensing a surgical fastener. In one embodiment, the height of the conduit 905 is greater than the thickness of the flexible member 960 so that the flexible member 960 may buckle a controlled amount to act as a damper and/or limit the travel of the flexible member. In one embodiment, the taller sections of the conduit 905 relative to the thickness of the flexible member 960 may be contained within a designated or limited area of the elongated shaft 902 for providing the dampening effect.

Figure 37:
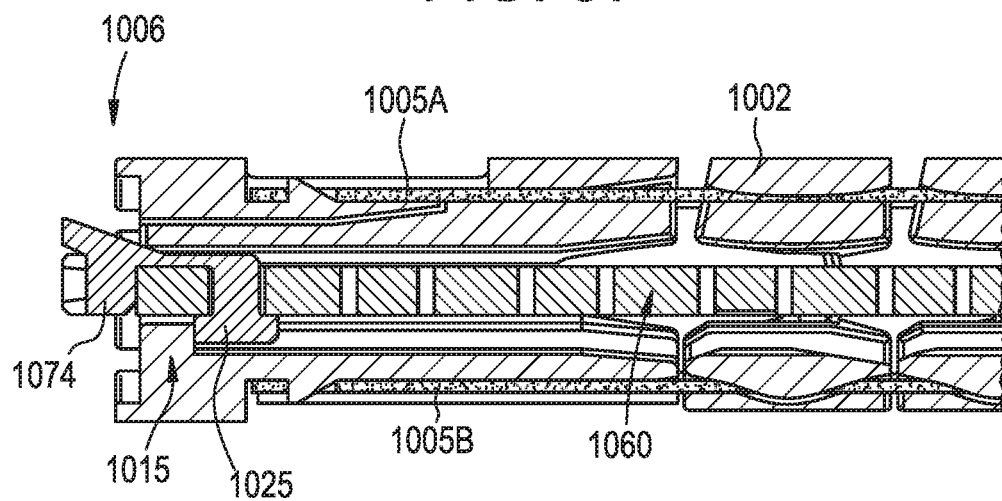
FIG. 37 shows a cross-sectional view of a distal end of an elongated shaft having a positive distal stop for halting distal movement of a flexible member, in accordance with one embodiment of the present patent application.

Referring to FIG. 37, in one embodiment, a distal end 1006 of an elongated shaft 1002 includes a distal positive stop 1015 that extends into the elongated conduit of the elongated shaft 1002. In one embodiment, an insertion tool 1074 attached to a distal end of the flexible member 1060 preferably includes a rear attachment flange 1025 that is adapted to contact the distal positive stop 1015 for halting further distal movement of the insertion tool 1074 and the flexible member 1060.

Figure 38:
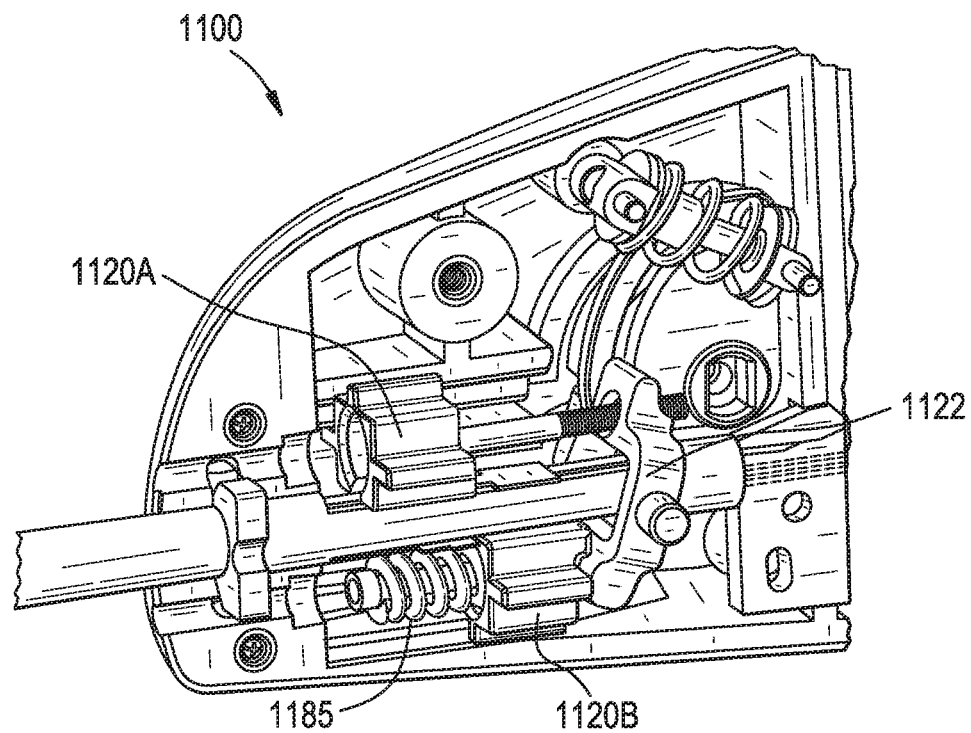
FIG. 38 shows a partial cross-sectional view of an applicator instrument having an articulation system with a tensioning spring coupled with a slider, in accordance with one embodiment of the present patent application.

Referring to FIG. 38, in one embodiment, an applicator instrument 1100 has one or more of the structural components described herein and preferably includes first and second sliders 1120A, 1120B coupled with a yoke 1122 for adjusting the tension on articulation bands. A tensioning spring 1185 is coupled with the second slider 1120B. In one embodiment, the tensioning spring 1185 desirably provides tension force relief in the event that excessive tension force is applied to the lower articulation band secured to the articulation member at the distal end of the elongated shaft 1102.

Figure 39:
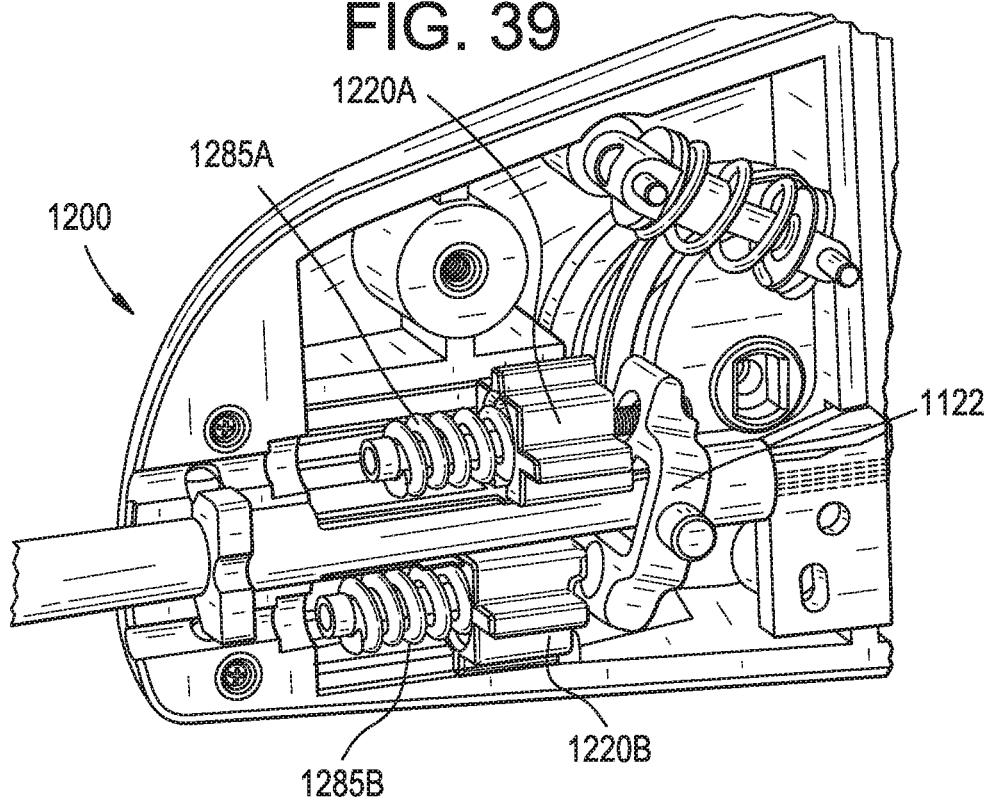
FIG. 39 shows a partial cross-sectional view of an applicator instrument having an articulation system with a first tensioning spring coupled with a first slider and a second tensioning spring coupled with a second slider, in accordance with one embodiment of the present patent application.

Referring to FIG. 39, in one embodiment, an applicator instrument 1200 has one or more of the structural components described herein and preferably includes first and second sliders 1220A, 1220B coupled with a yoke 1222 for adjusting the tension on upper and lower articulation bands. A first tensioning spring 1285A is coupled with the first slider 1220AB. In one embodiment, the first tensioning spring 1285A desirably provides tension force relief in the event that excessive tension force is applied to the upper articulation band secured to the articulation member located at the distal end of the elongated shaft 1202. In one embodiment, the second tensioning spring 1285B desirably provides tension force relief in the event that excessive tension force is applied to the lower articulation band secured to the articulation member at the distal end of the elongated shaft 1202.

Figure 40:
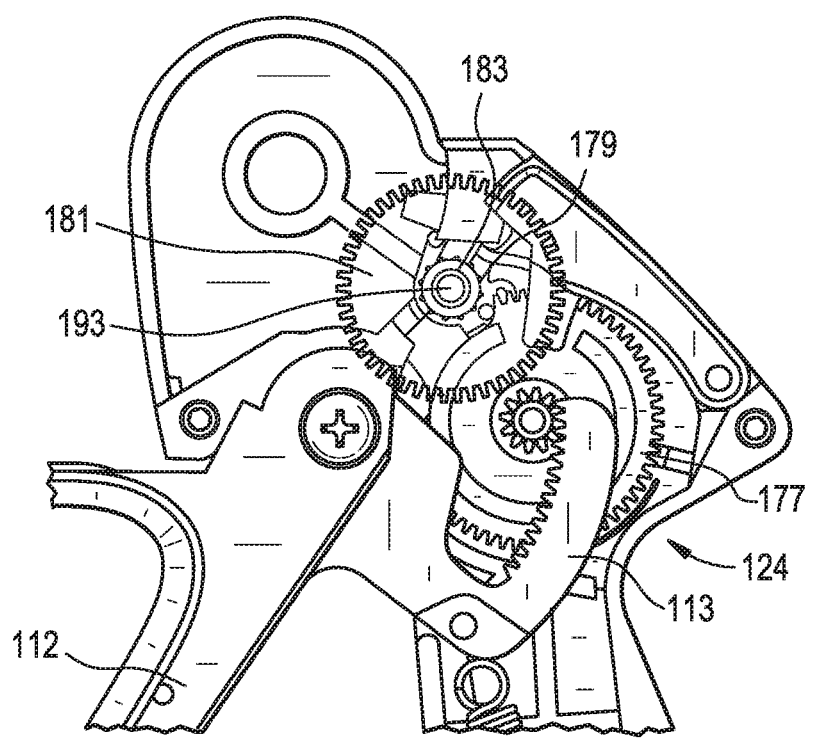
FIGS. 40 and 41A-41D show a gear train for an applicator instrument, in accordance with one embodiment of the present patent application.

Referring to FIG. 40, in one embodiment, a drive train 124 for an applicator instrument may include a trigger gear 113 attached to the trigger 112, a drive gear 177 that meshes with the trigger gear 113, a clutch gear 179 that meshes with the drive gear 177, a mid gear 181 that may be coupled with the clutch gear 179, a one-way bearing 183, and a clutch gear shaft 193 coupled with the clutch gear 179 for simultaneously rotating with the clutch gear. In one embodiment, the one-way bearing 183 is disposed on the clutch gear shaft 193. In one embodiment, the gears preferably have teeth for meshing with other gears of the gear train 124.

Figure 41A:
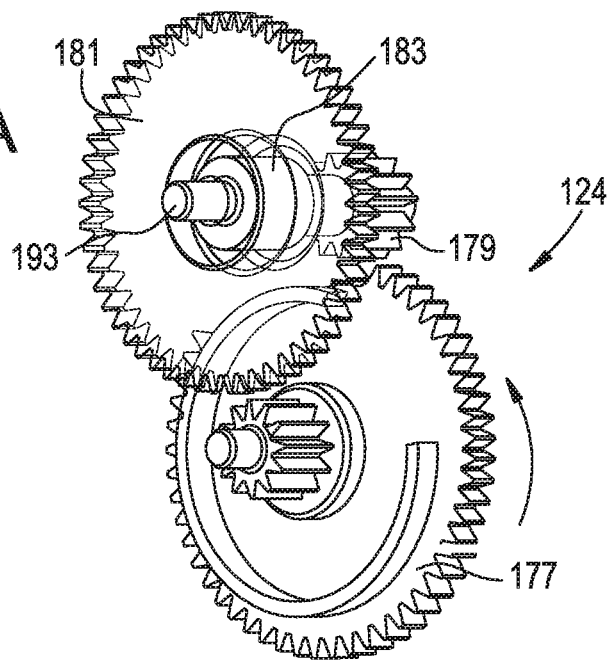

Referring to FIGS. 40 and 41A, in one embodiment, the drive train for an applicator instrument preferably includes the drive gear 177 having teeth that mesh with teeth on the clutch gear 179. When the trigger is fully extended in the ready to fire position, the drive gear 177 and the clutch gear 179 are disengaged via an interruption in the teeth pattern on the drive gear 177. The drive train desirably includes the mid gear 181 having a central opening that receives the one-way bearing 183, which, in turn, is mounted on the clutch gear shaft 193.

Figure 41B:
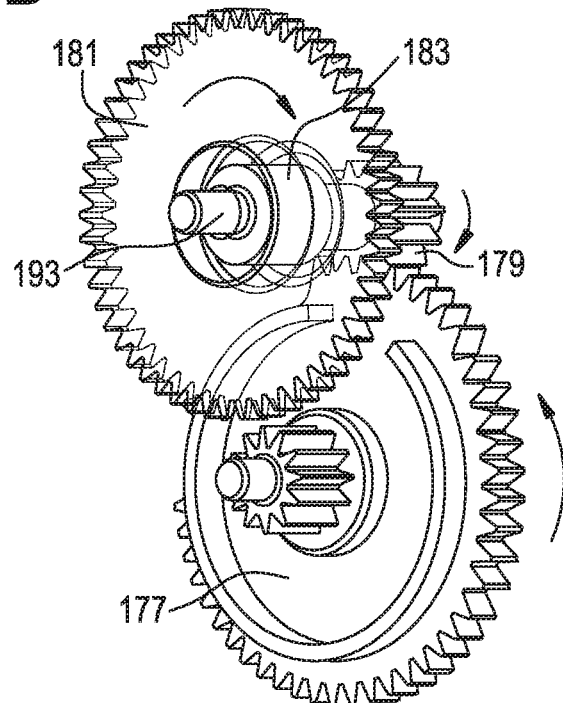

Referring to FIGS. 40 and 41B, in one embodiment, as the trigger 112 is squeezed, the trigger gear 113 rotates the drive gear 177 in the counterclockwise direction shown in FIG. 41B. The teeth on the drive gear 177 engage the teeth on the clutch gear 179 for rotating the clutch gear 179 in the clockwise direction shown in FIG. 41B. As the clutch gear 179 rotates clockwise, the clutch gear shaft 193 drives the one-way bearing 183 in a clockwise direction during which the one-way bearing 183 engages the mid gear 181 for rotating the mid gear in the clockwise direction shown in FIG. 41B. In turn, the mid gear 181 drives the storage reel 126 (FIG. 14A-1) to wind up the flexible member 160 on the storage reel and store energy in the constant torque spring 172 (FIG. 10B). In one embodiment, the one-way bearing 183 only engages and drives rotation of the mid gear 181 when the clutch gear shaft 193 rotates in the clockwise direction shown in FIG. 41B. The one-way bearing 183 preferably free wheels when the clutch gear shaft 193 rotates in a counterclockwise direction that is opposite the clockwise direction so that the clutch gear 179 and the mid gear 181 are decoupled from one another.

Figure 41C:
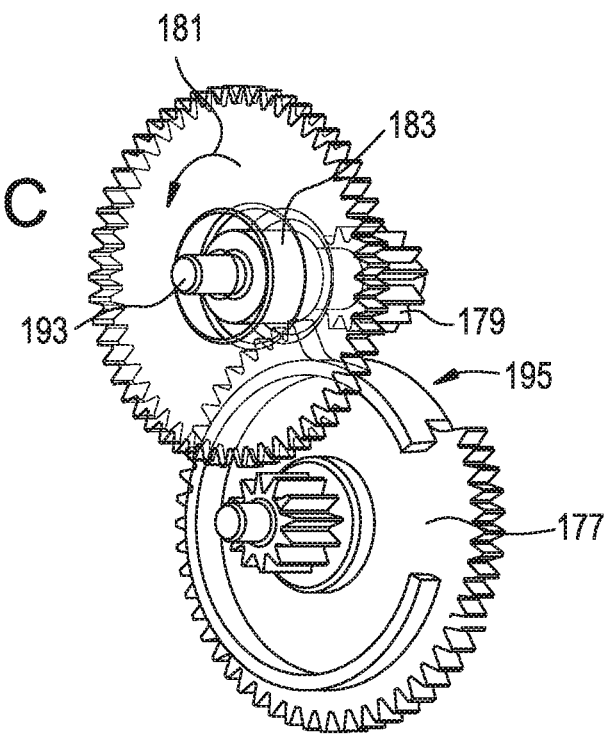

Referring to FIGS. 40 and 41C, when the trigger 112 is almost fully squeezed (i.e., at the end of a trigger stroke), the interrupted tooth section 195 on the drive gear 177 results in the drive gear disengaging from the clutch gear 179. This disengagement allows the mid gear 181 and the clutch gear 179 to move freely without any resistance from the trigger 112 and the gear train. At this stage, the energy that is stored in the constant torque spring 172 (FIG. 10B) is released for driving the drive wheel 128 (FIG. 16A) for advancing the flexible member 160 (FIG. 16B) toward the distal end of the elongated shaft.

Figure 41D:
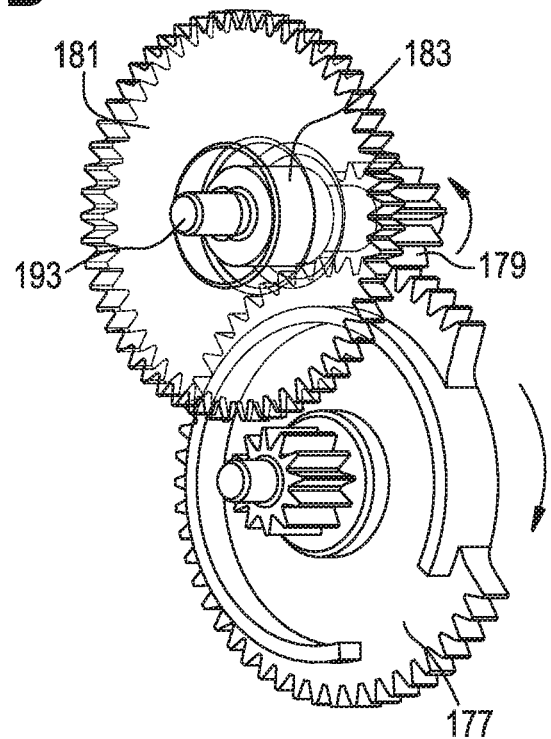

Referring to FIGS. 40 and 41D, in one embodiment, after the trigger has been fully squeezed and the trigger return spring returns the trigger back to an open position, the trigger gear 113 rotates the drive gear 177 in a clockwise direction. In turn, the drive gear 177 rotates the clutch gear 179 in a counterclockwise direction. As the clutch gear 179 and the clutch gear shaft 193 rotate in the counterclockwise direction, the one-way bearing 183 will disengage from the clutch gear shaft 193. Thus, the counterclockwise rotation of the clutch gear 179 will not be conveyed to the mid gear 181, and therefore, the distal end of the firing system that includes the drive wheel 128 and the storage reel 126 will not be impacted by the trigger returning back to the open position. Thus, in one embodiment, the one-way bearing 183 disengages from the clutch gear shaft 193 when the clutch gear shaft rotates in a counterclockwise direction, whereupon the mid gear 181 will not be rotated by the one-way bearing 183.

Referring to FIGS. 42A-42E, in one embodiment, the drive wheel 128, the storage reel 126, and the spool 139 (FIG. 10B) are assembled onto a carriage 165. In one embodiment, the carriage 165 is normally spring loaded distal but is held proximal by a catch 167. When the insertion tool 174 retracts, it releases the catch 167 and allows the carriage 165 to move distal, urged by a spring. When the carriage 165 moves distal, the storage reel 126 disconnects from the drive train 124 and the constant torque spring 172 accelerates the flexible member 160 and the surgical fastener toward the distal end of the elongated shaft 102 for being inserted into tissue. Once delivered, the flexible member experiences compressive loads due to the inertia of the drive wheel 128. The reaction force to these compressive loads generates a torque on the drive wheel 128, which allows the carriage 165 to move proximal and reset the catch 167. In one embodiment, inserting the cartridge 116 into the housing pushes the carriage 165 toward the proximal end of the housing, which engages/meshes the storage reel 126 with the drive train 124 so that the applicator instrument may be fired. In one embodiment, the cartridge 116 also engages the catch 167. Removing the cartridge 116 releases the catch 167 and allows the carriage 165 to move distal, disengaging the drive gear 165 and the storage reel 126 and preventing the device from being fired.

Figure 42A:
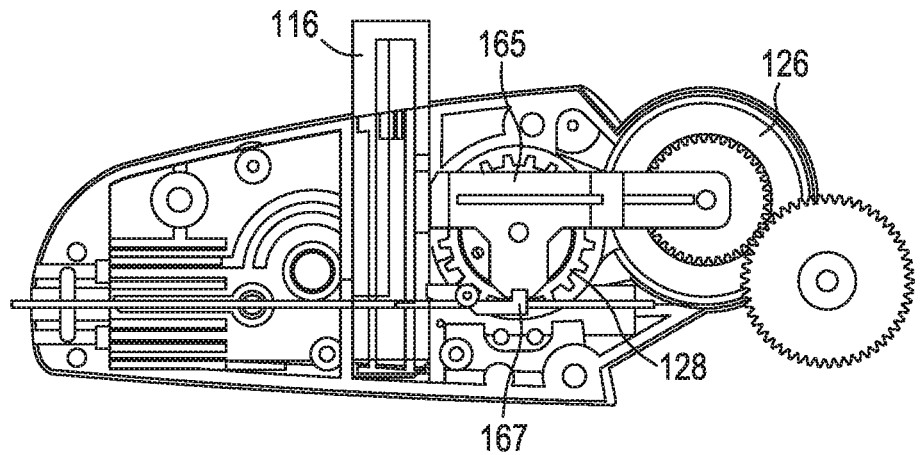
FIGS. 42A-42E show an applicator instrument, in accordance with one embodiment of the present patent application.

Referring to FIG. 42A, in one embodiment, the drive wheel 128, storage reel 126, and spool 139 (FIGS. 10A and 10B) are assembled onto a carriage 165. The carriage 165 is spring loaded distal but is held proximal by a catch 167.

Figure 42B:
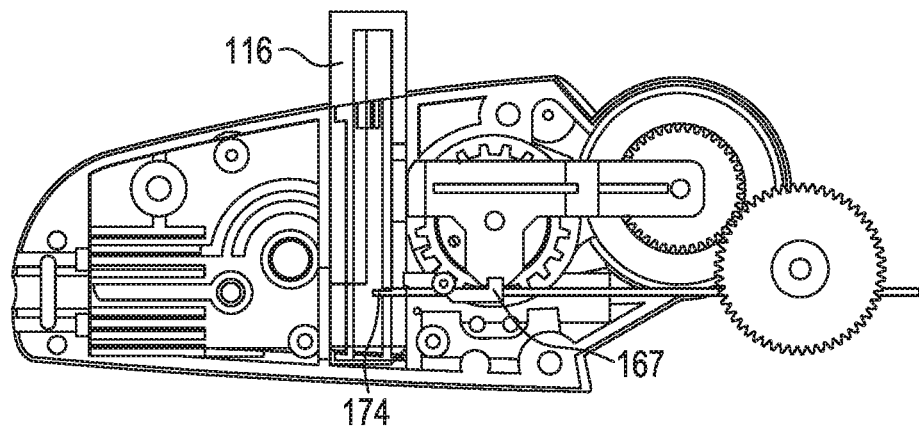
Figure 42C:
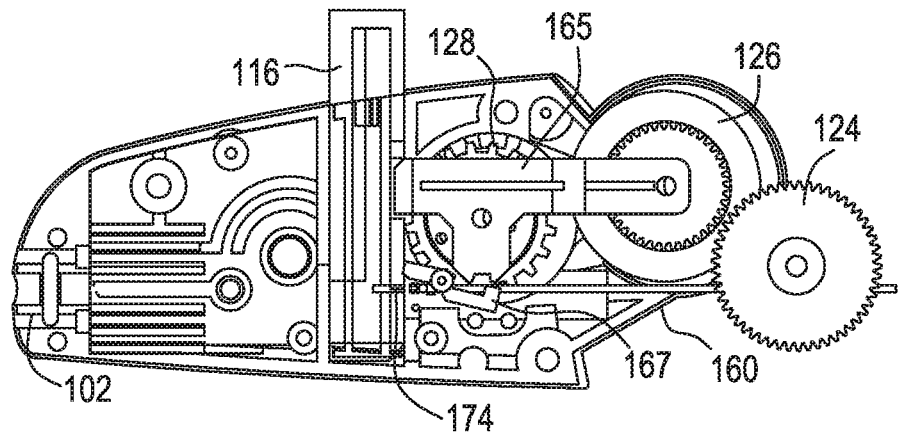

Referring to FIGS. 42B and 42C, in one embodiment, when the insertion tool 174 fully retracts, it releases the catch 167 and allows the carriage 165 to move distal, urged by the spring.

Figure 42D:
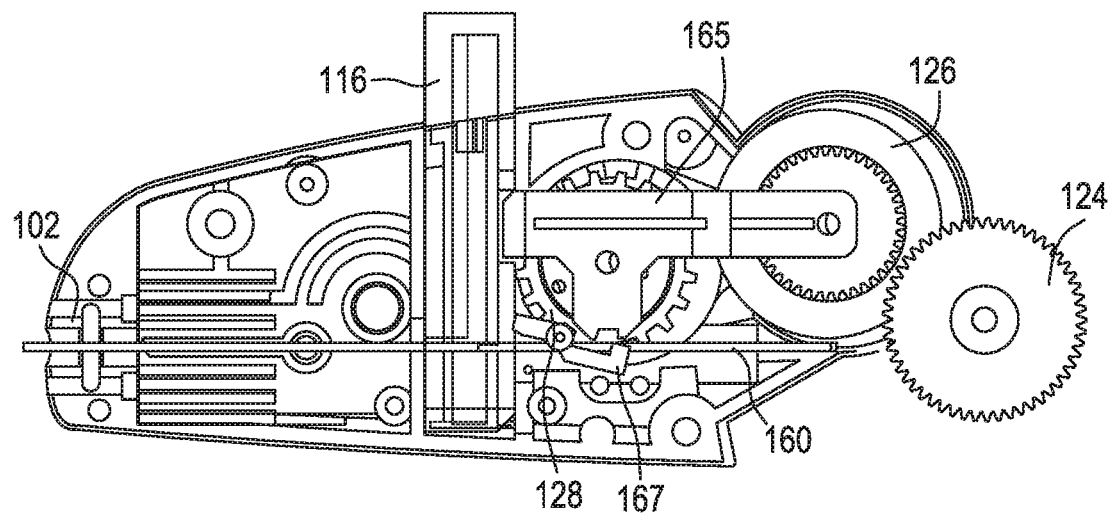

Referring to FIGS. 42C and 42D, in one embodiment, when the carriage 165 moves distal, the storage reel 126 disconnects from the drive train 124 and the constant torque spring 172 accelerates the flexible member 160 and the surgical fastener toward the distal end of the elongated shaft 102 for being inserted into tissue.

Figure 42E:
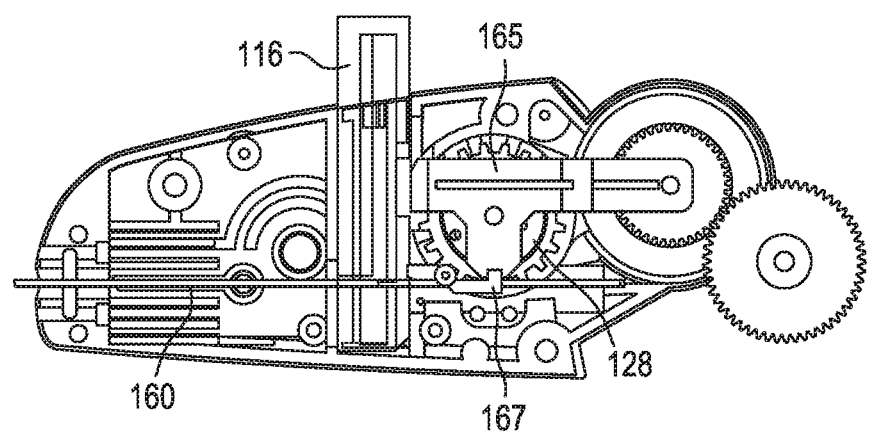

Referring to FIG. 42E, in one embodiment, once delivered, the flexible member 160 experiences compressive loads due to the inertia of the drive wheel 128. The reaction force to these compressive loads generates a torque on the drive wheel 128, which allows the carriage 165 to move proximal and reset the catch 167.

In one embodiment, the drive wheel 128, storage reel 126, and spool are assembled onto a carriage. The carriage is spring loaded distal but is held proximal by a catch. When the insertion tool 174 retracts, it releases the catch and allows the carriage 165 to move distal, urged by the spring. When the carriage 165 moves distal, the storage reel 126 disconnects from the drive train 124 and the constant torque spring 172 (FIGS. 10A and 10B) accelerates the flexible member 160 and the surgical fastener toward the distal end of the elongated shaft 102 for being inserted into tissue. Once delivered, the flexible member experiences compressive loads due to the inertia of the drive wheel 128. The reaction force to these compressive loads generates a torque on the drive wheel 128, which allows the carriage to move proximal and reset the catch. As a refinement to the above, adding the cartridge 116 pushes the carriage 165 proximal engaging the drive train and storage reel into mesh (allowing the device to be fired). The cartridge 116 also engages the latch 167. Removing the cartridge 116 releases the latch 167 and allows the carriage 165 to move distal, disengaging the mid gear and tape gear and preventing the device from being fired.

Figure 43A:
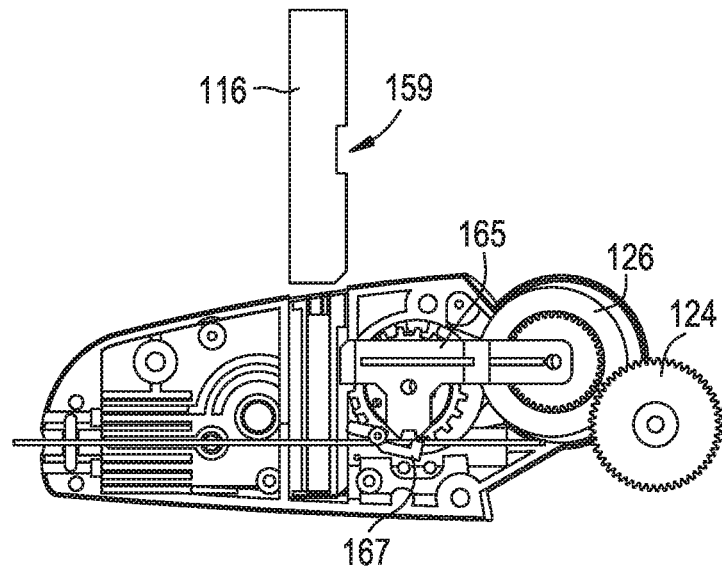
FIGS. 43A-43C show an applicator instrument, in accordance with one embodiment of the present patent application.
Figure 43B:
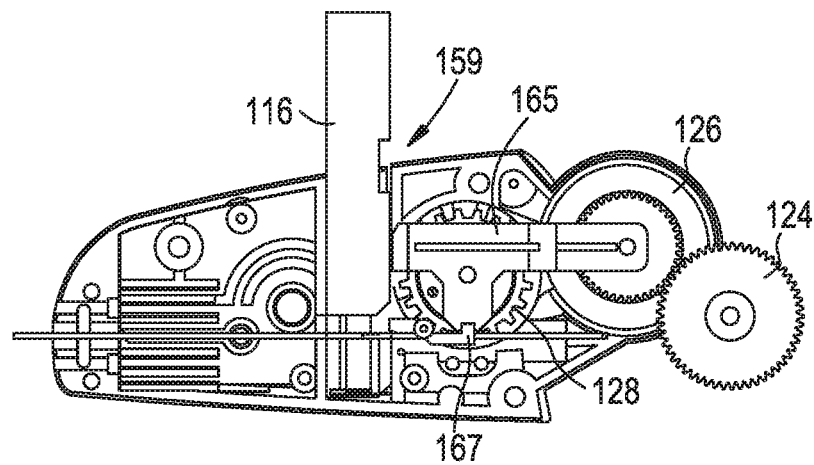
Figure 43C:
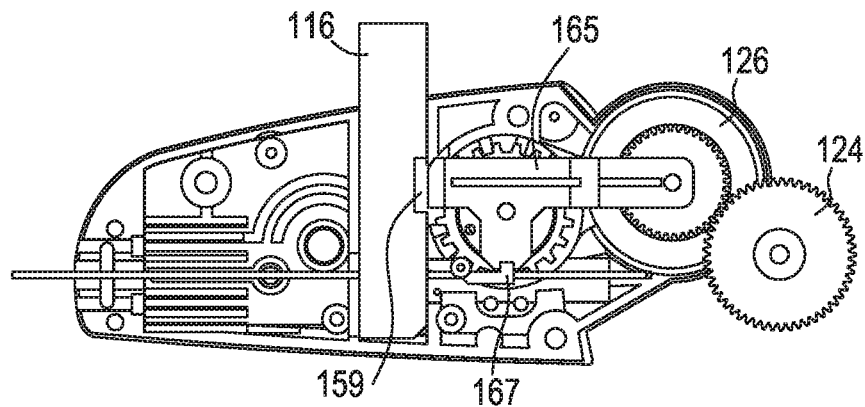

In one embodiment, the applicator instrument may only be fired when the cartridge 116 is inserted into the applicator instrument and cannot be fired when the cartridge 116 has been removed from the applicator instrument. Referring to FIGS. 43A-43C, in one embodiment, inserting the cartridge 116 into the applicator instrument pushes the carriage 165 toward the proximal end of the applicator instrument (to the right in FIGS. 43A-43C), which, in turn, couples and/or meshes the drive train 124 with the storage reel 126 (FIGS. 43B and 43C) for enabling the applicator instrument to be fired. In one embodiment, the cartridge 116 may also engage the catch 167. Referring to FIG. 43C, once the cartridge is in place, the cartridge no longer interacts with the carriage. In one embodiment, the cartridge 116 has a notch 159 formed on the right side of the cartridge, which allows the carriage 165 to translate proximally and distally, as necessary, during each firing stroke.

In one embodiment, removing the cartridge 116 releases the catch 167 for allowing the carriage 165 to move distal (to the left in FIGS. 43A-43C), thereby disengaging the drive train 124 from the storage reel 126 and preventing the applicator instrument from being fired.

Figure 44A:
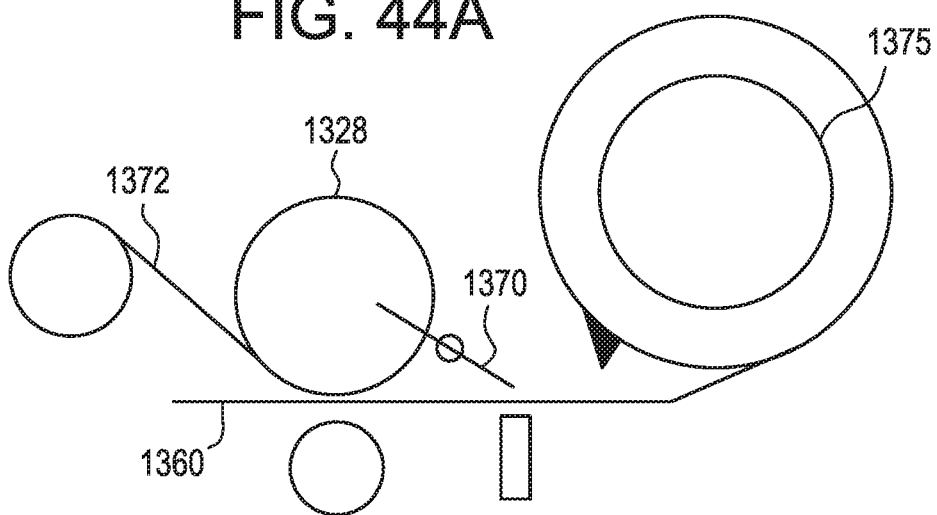
FIGS. 44A-44C show schematic views of a firing system for an applicator instrument, in accordance with one embodiment of the present patent application.

Referring to FIG. 44A, in one embodiment, a firing system includes a flexible member 1360 that is initially retracted and held proximal by a power spring 1375. A friction drive wheel 1328 has potential energy stored therein. In one embodiment, the energy is stored via a constant torque spring 1372 pre-wound onto the drive wheel during assembly, such that the spring has adequate length to facilitate multiple cycles. Alternative stored energy means may include electro-mechanical, pneumatic, mechanical, motor driven, compressed gas, or other well-known energy sources. The friction drive wheel 1328 is held in place by a lever lock 1370, preventing clockwise rotation.

Figure 44B:
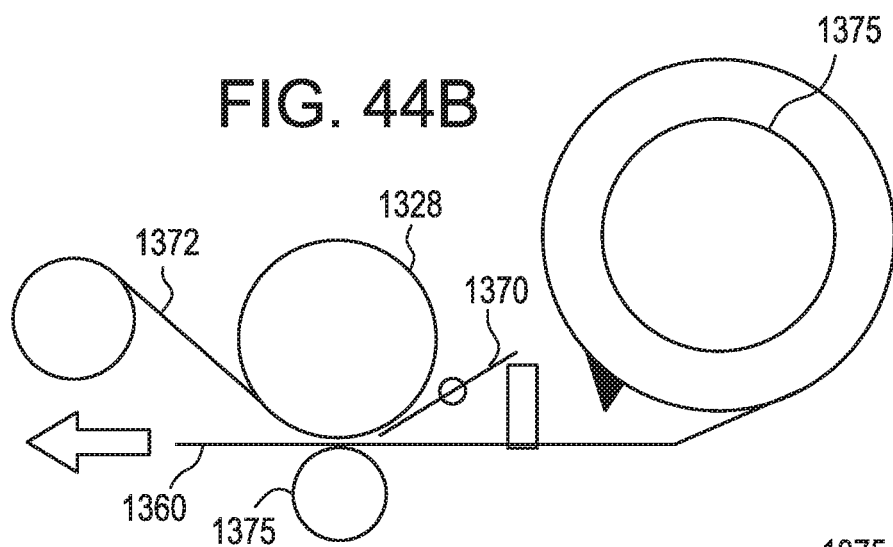

Referring to FIG. 44B, in one embodiment, squeezing a trigger of the applicator instrument engages an idler wheel 1375 with the flexible member 1360 and toggles the level lock 1370. At this stage, the constant torque spring 1372 has more force than the power spring 1375, and drives the flexible member 1360 distally (to the left in FIG. 44B).

Figure 44C:
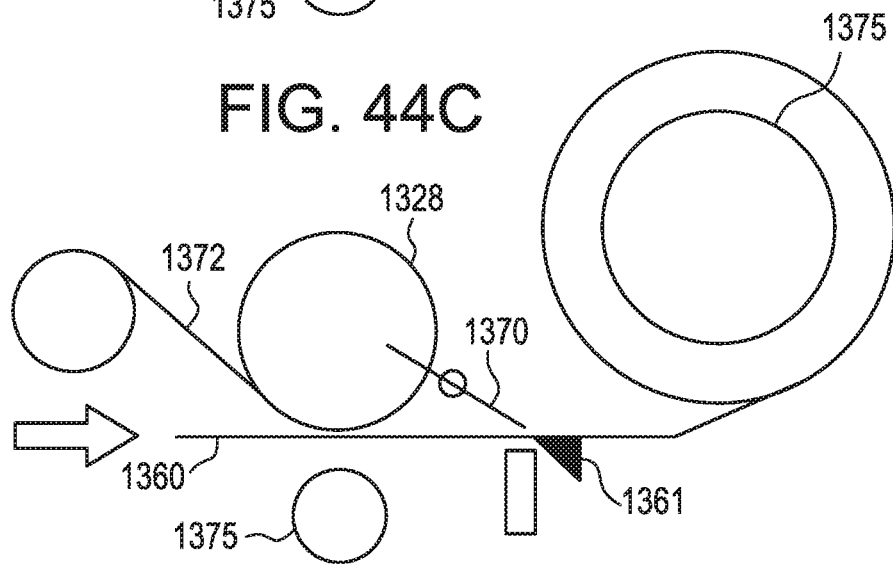

Referring to FIG. 44C, in one embodiment, a proximal or trailing end of the flexible member 1360 includes a wedge 1361 that allows the spring loaded lever 1370 to re-engage with the friction drive wheel 1328. At this stage, the idler wheel 1375 separates from the flexible member 1360, which enables the power spring 1375 to retract the flexible member 1360.

In one embodiment, some of the energy stored in the constant torque spring 1372 is used on each firing cycle. In one embodiment, the constant torque spring 1372 is sufficiently long to provide enough energy for many firing cycles. This design has many benefits including that the force required of the user is very low (e.g., a user may only need to engage the idler wheel 1375 and release the lever lock 1370).

In an alternate embodiment, the constant torque spring is pre-wound onto the drive wheel during assembly to have sufficient stroke for multiple cycles. A latch holds the drive wheel in place, preventing rotation. During the trigger squeeze, the flexible member is wound onto the storage reel but is disengaged from the drive wheel, reducing the trigger force for the user. When the user has nearly completed the trigger stroke, the trigger releases a latch, which engages an idler with the flexible member and the drive wheel. The latch also releases the constraint preventing rotation on the drive wheel. This allows the drive wheel to accelerate due to the force applied by the constant torque spring. The flexible member extends distally, delivering the fastener. As the flexible member reaches the end of its travel, a feature on the flexible member resets the latch and disengages the flexible member from the drive wheel.

Referring to FIGS. 44A-44C, in one embodiment, the constant torque spring 1372 is pre-wound onto the drive wheel during assembly to have sufficient stroke for multiple cycles. A latch holds the drive wheel in place, preventing rotation. During the trigger squeeze, the flexible member is wound onto the storage reel but is disengaged from the drive wheel, reducing the trigger force for the user. When the user has nearly completed the trigger stroke, the trigger releases a latch, which engages the flexible member with the drive wheel and releases the constraint preventing rotation on the drive wheel. This allows the drive wheel to accelerate due to the force applied by the constant torque spring. The flexible member extends distally, delivering the fastener. As the flexible member reaches the end of its travel, a feature on the flexible member resets the latch and disengages the flexible member from the drive wheel.

Figure 45A:
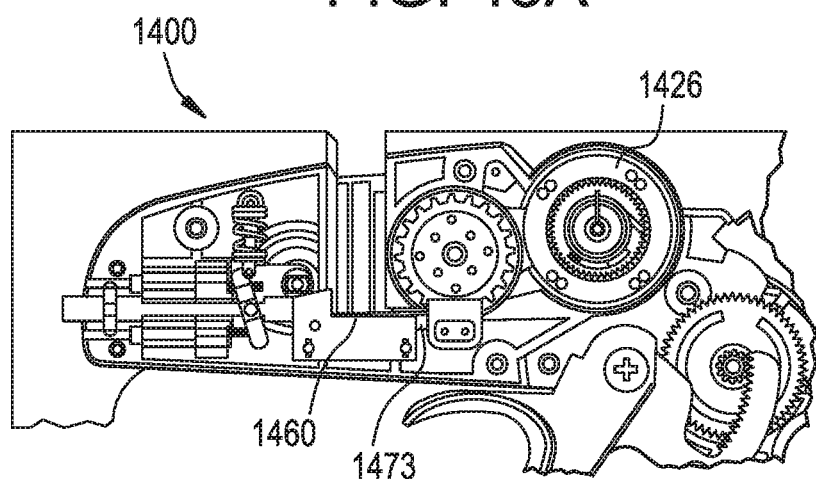
FIG. 45A shows an applicator instrument having a flexible member in an extended position, in accordance with one embodiment of the present patent application.
Figure 45B:
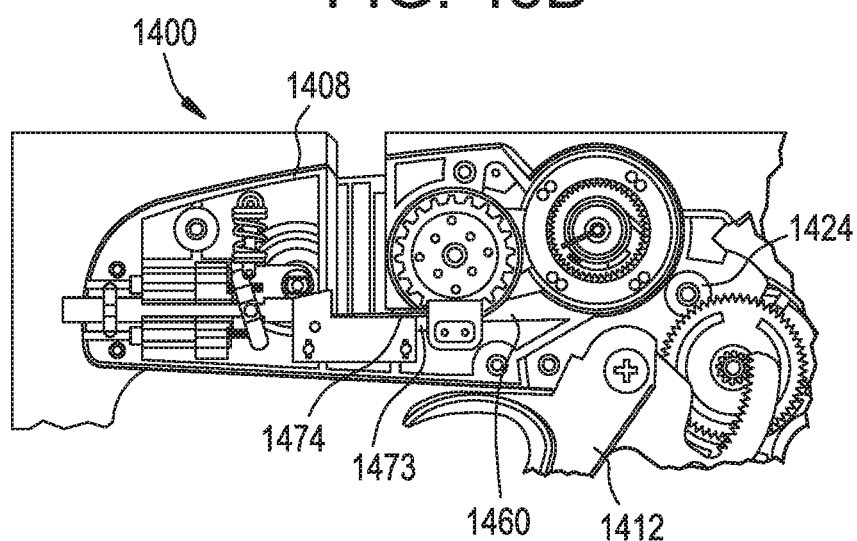
FIG. 45B shows an applicator instrument having a flexible member in a retracted position, in accordance with one embodiment of the present patent application.

FIG. 45A shows an applicator instrument 1400 having one or more of the elements described herein. In FIG. 45A, the applicator instrument 1400 has a flexible member 1460 in an extended position for dispensing a surgical fastener. In FIG. 45B, the flexible member 1460 is in a retracted position. In one embodiment, a torsion spring is assembled with the storage reel 1426. The torsion spring is preferably pre-assembled with a torque greater than that required to wind the flexible member 1460 onto the storage reel. When the insertion tool 1474 is fully retracted, it preferably engages a proximal stop 1473 that prevents further proximal travel of the insertion tool 1474. At this point, the flexible member 1460 is stationary and further travel of the trigger 1412 and gear train 1424 only results in extra compression of the torsion spring. Such a system accounts for tolerances and ensures that the insertion tool 1474 is reliably retracted proximal of the cartridge 116 (FIG. 13B) on every firing cycle.

Figure 46A:
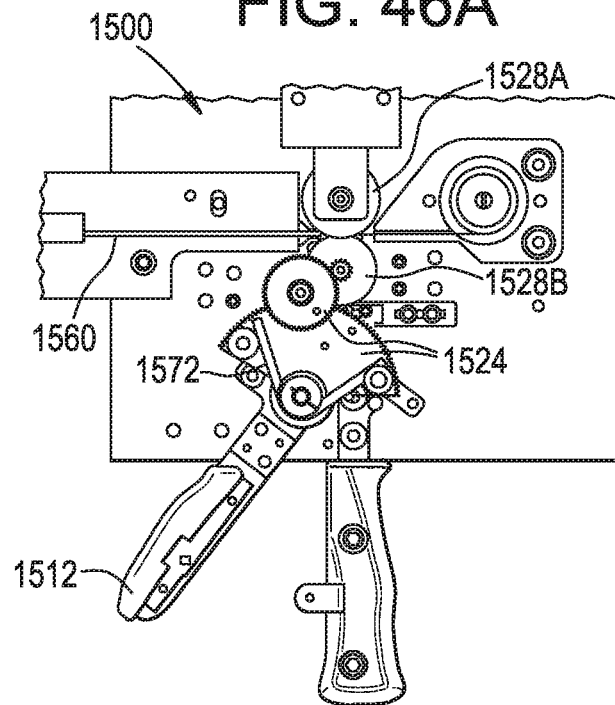
FIGS. 46A-46E show a schematic of an applicator instrument having an energy storing assembly, in accordance with one embodiment of the present patent application.

Referring to FIG. 46A, in one embodiment, an applicator instrument 1500 for dispensing surgical fasteners includes a firing system that incorporates the "coiled snake" concept. In one embodiment, the applicator instrument 1500 includes an actuator or trigger 1512 that is coupled with a gear train 1524, a torsion spring 1572, a pair of drive wheels 1528A and 1528B, and a flexible member 1560 that is advanced distally by the drive wheels.

Figure 46B:
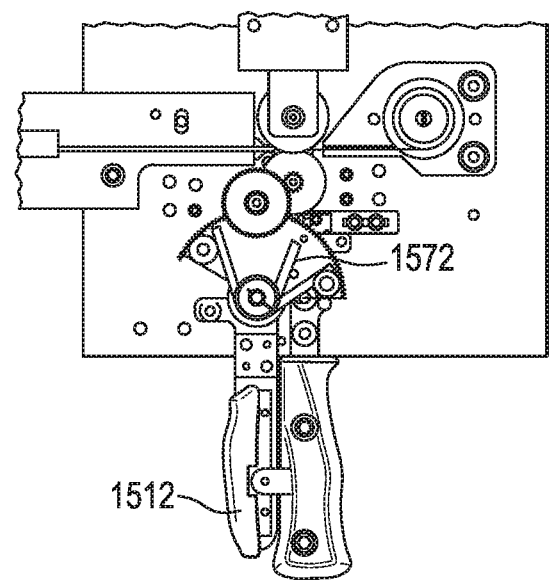
Figure 46C:
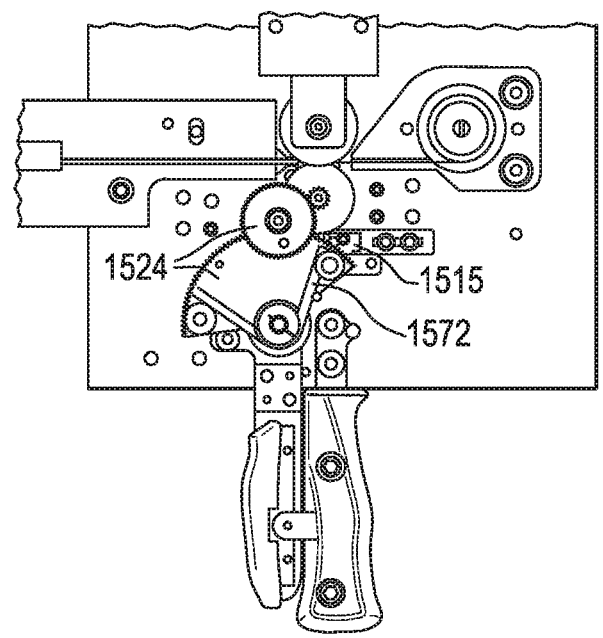
Figure 46D:
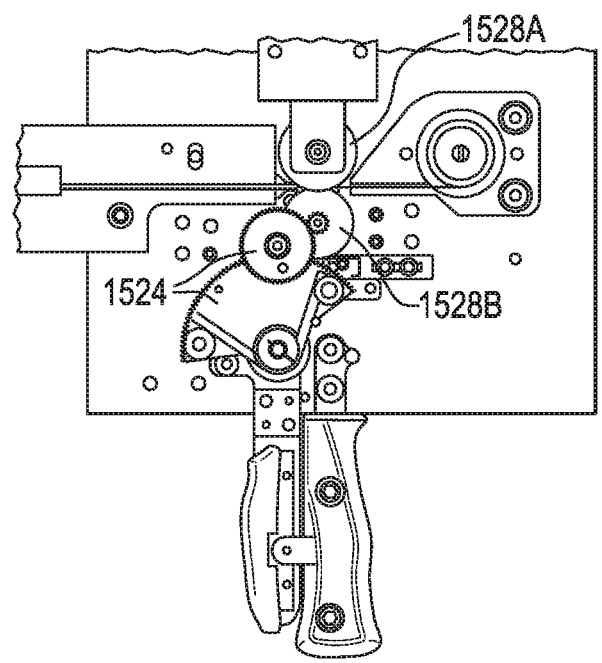
Figure 46E:
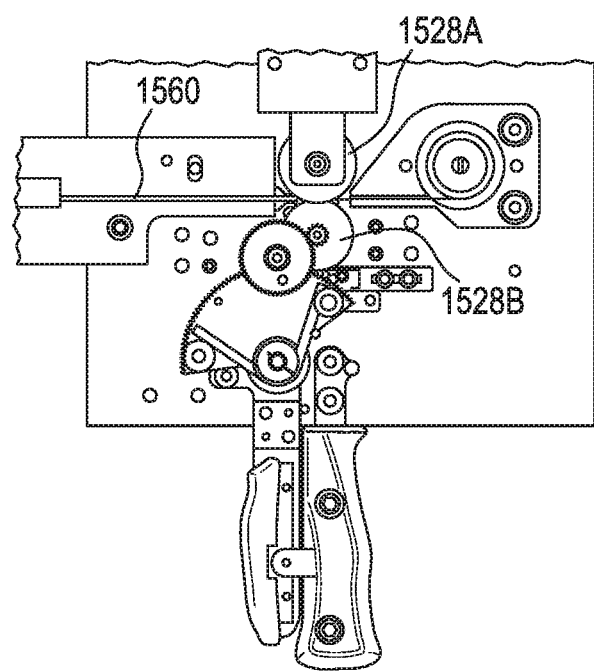

Referring to FIG. 46B, in one embodiment, as the user squeezes the trigger 1512, one end of the torsion spring is held in place by a latch 1515 and the other end is rotated, compressing the torsion spring and storing potential energy. Referring to FIG. 46C, near the conclusion of the trigger compression stroke, a latch 1515 releases the energy that has been previously stored in the torsion spring 1572. In turn, the energy from the torsion spring 1572 drives the gear train 1524. Referring to FIG. 46D, in one embodiment, the stored energy is transmitted through the gear train 1524 for rotating the upper drive wheel 1528A in a clockwise direction and the lower drive wheel 1528B in a counterclockwise direction. Referring to FIG. 46E, in one embodiment, the rotating drive wheels 1528A and 1528B, which may be friction wheels or cogged wheels, drive the flexible member 1560 toward a distal end of a cannula for delivering a surgical fastener from the distal end of the cannula.

In one embodiment, an applicator instrument for dispensing surgical fasteners may have a firing system that incorporates the "coiled snake" concept disclosed herein whereby the firing system uses energy stored in a spring that is located distal to the gear train. In one embodiment, an applicator instrument for dispensing surgical fasteners may have a firing system that incorporates the "coiled snake" concept disclosed herein whereby the firing system uses energy stored in a spring located prior or proximal to the gear train, with the energy being released through the drive train to drive the flexible member. In one embodiment, a user squeezes a trigger, handle and/or actuator for compressing a torsion spring. At the conclusion of the compression stroke, a latch is disengaged for releasing the energy stored in the torsion spring. In one embodiment, the energy stored in the compression spring is transmitted through a gear train to a set of drive wheels. The released energy rotates the drive wheels, which, in turn, drive the flexible member down a cannula to deliver the surgical fastener from the distal end of the cannula.

In one embodiment, the applicator instruments disclosed herein may be used during surgical procedures such as hernia repair procedures. In one embodiment, the patient is prepared for surgery in administering anesthesia. Abdominal access is prepared by inserting two or more ports through the abdominal wall and insufflating the abdominal cavity. The hernia site is assessed under direct visualization using a laparoscopic camera. Adhesions are reduced and the peritoneum sac is excised if appropriate. A mesh is placed into the abdominal cavity. The surgeon selects from a variety of cartridges to identify one appropriate for the type of hernia repair being performed. The variety may include different fastener designs, materials, or quantities. The cartridge is attached to the applicator instrument. The distal end of an elongated shaft is advanced through one of the port openings. During a surgical procedure, the distal end of the elongated shaft may be articulated if necessary to access areas requiring fixation, such as the ipsilateral side of the mesh, nearest the port. When the elongated shaft is passed through a port, the reconfigurable handle may be pivoted into a variety of configurations to improve the ergonomics and maneuverability of the surgeon, depending on the location of the target fixation site relative to the port. The applicator instrument may be used to dispense surgical fasteners for securing surgical mesh to tissue. Cartridges can be changed for reloading or changing the type of surgical fastener being dispensed by the applicator instrument. The articulated distal end is straightened before removing the device through the port.

In one embodiment, the applicator instruments disclosed herein may be used during robotic surgical procedures such as hernia repair procedures. In one embodiment, the patient is prepared for surgery in administering anesthesia. Abdominal access is prepared by inserting two or more ports through the abdominal wall and insufflating the abdominal cavity. A surgical robot is attached to the pre-placed ports. The hernia site is assessed under direct visualization using a laparoscopic camera. Adhesions are reduced and the peritoneum sac is excised if appropriate. A mesh is placed into the abdominal cavity. The surgeon selects from a variety of cartridges to identify one appropriate for the type of hernia repair being performed. The variety may include different fastener designs, materials, or quantities. The cartridge is attached to the applicator instrument. The distal end of an elongated shaft is advanced through one of the port openings. The housing assembly is attached to the arm of a surgical robot. During a surgical procedure, the distal end of the elongated shaft may be articulated if necessary to access areas requiring fixation, such as the ipsilateral side of the mesh, nearest the port. The applicator instrument may be used to dispense surgical fasteners for securing surgical mesh to tissue. Cartridges can be changed for reloading or changing the type of surgical fastener being dispensed by the applicator instrument. The articulated distal end is straightened before removing the device through the port.

In one embodiment, the applicator instruments and surgical tools disclosed herein may be coupled with and/or be in communication with a robotic surgical system, such as the systems and devices disclosed in US 2014/0005662 to Shelton, the disclosure of which is hereby incorporated by reference herein. In one embodiment, the robotic surgical system may have a sterile barrier located between the applicator instruments and surgical tools and the robotic part of the robotic surgical system, whereby the applicator instruments and surgical tools are located in the sterile environment.

In one embodiment, a robotic surgical system may have a master controller and control systems such as the systems and devices disclosed in U.S. Pat. No. 7,524,320, the disclosure of which is hereby incorporated by reference herein. The master controller may have control elements (e.g., knobs, actuators) that are engaged by a surgeon and manipulated in space while the surgeon views a surgical site through a video monitor and/or stereo display. The master controller may include manual input devices that move with multiple degrees of freedom. In one embodiment, the master control has an actuator for actuating surgical tools (e.g., dispensing a surgical fastener).

In one embodiment, the robotic surgical system may include a robotic cart that is configured to actuate a plurality of surgical tools and/or instruments. Various robotic surgery systems and methods employing master controller and robotic cart arrangements are disclosed in U.S. Pat. No. 6,132,368, the disclosure of which is hereby incorporated by reference herein. In one embodiment, a robotic cart may include a base from which surgical tools are supported. In one embodiment, the surgical tools may be supported by a series of manually articulatable linkages, generally referred to as set-up joints, and a robotic manipulator. These structures may have protective covers extending over much of the robotic linkage. The protective covers may be optional, and may be limited in size or entirely eliminated to minimize the inertia that is encountered by servomotors used to manipulate such devices, to limit the volume of moving components so as to avoid collisions, and to limit the overall weight of the robotic cart. In one embodiment, the robotic cart may have dimensions suitable for transporting the cart between operating rooms. The robotic cart is preferably configured to pass through standard operating room doors and onto standard hospital elevators. The robotic cart preferably has a weight and includes one or more wheels that allow the cart to be easily moved and positioned adjacent an operating table.

Other embodiments may incorporate a wide variety of alternative robotic structures, including those described in U.S. Pat. No. 5,878,193, the disclosure of which is hereby incorporated by reference herein. Additionally, while the data communication between a robotic component and the processor of the robotic surgical system is described with reference to communication between the surgical tool and the master controller, similar communication may take place between circuitry of a manipulator, a set-up joint, an endoscope or other image capture device, or the like, and the processor of the robotic surgical system for component compatibility verification, component-type identification, component calibration communication, and confirmation of coupling of the component to the robotic surgical system.

In one embodiment, during a surgical procedure, a surgeon may input control commands to the master controller or a control unit of the robotic surgical system, which "robotically-generates" output motions that are ultimately transferred to the applicator instruments disclosed herein. As used herein, the terms "robotically-generates" or "robotically-generated" refer to motions that are created by powering and controlling the motors of the robotic surgical system and other power driven components. These terms are distinguishable from the terms "manually-actuatable" or "manually generated" which refer to actions taken by a surgeon that result in control motions that are generated independent from those motions that are generated by powering the motors of the robotic surgical system.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. An applicator instrument having a reconfigurable handle for dispensing surgical fasteners comprising:
   a housing;
   an elongated shaft extending from a distal end of said housing;
   a handle coupled with a proximal end of said housing;
   a trigger coupled with said handle;
   a firing system disposed within said housing, said firing system including an energy storing assembly;
   a gear train disposed within said handle and coupled with said trigger, wherein said trigger is squeezable for storing energy in said energy storing assembly;

a handle reconfiguration actuator having a first position for locking said handle in place relative to said housing while enabling said trigger to be squeezed toward said handle for commencing a firing cycle of said firing system, and a second position for enabling said handle to rotate relative to said housing between a pistol configuration and an in-line configuration while preventing said trigger from being squeezed toward said handle for blocking commencement of a firing cycle of said firing system.

2. The applicator instrument as claimed in claim 1, wherein said elongated shaft has a proximal end secured to said distal end of said housing, a distal end, and a longitudinal axis extending between said proximal and distal ends thereof, wherein said handle has a longitudinal axis that is orthogonal to the longitudinal axis of said elongated shaft when said handle is in the pistol configuration and generally parallel to the longitudinal axis of said elongated shaft when said handle is in the in-line configuration.

3. The applicator instrument as claimed in claim 1, wherein when said handle reconfiguration actuator is in the first position, said gear train in said handle is coupled with said firing system in said housing, and wherein when said handle reconfiguration actuator is in the second position, said gear train in said handle is decoupled from said firing system in said housing for enabling said handle to rotate relative to said housing.

4. The applicator instrument as claimed in claim 1, wherein said trigger is coupled with said handle and moves simultaneously with said handle as said handle rotates between the pistol configuration and the in-line configuration.

5. The applicator instrument as claimed in claim 1, wherein said proximal end of said housing has a concave surface and a distal end of said handle has a convex surface that matches the curve of said concave surface for guiding rotation of said handle between the pistol and in-line configurations.

6. The applicator instrument as claimed in claim 5, wherein said proximal end of said housing comprises a series of spaced reconfiguration notches that are arrayed in an arc-shaped pattern and that are utilized for positioning said handle at different angles relative to said housing.

7. The applicator instrument as claimed in claim 6, further comprising a slider that extends between said handle reconfiguration actuator and said reconfiguration notches at said proximal end of said housing, wherein said slider has a proximal end that is engaged by said handle reconfiguration actuator and a distal end that is adapted to be seated in said reconfiguration notches.

8. The applicator instrument as claimed in claim 7, wherein when said handle reconfiguration actuator is in the second position an underside of said handle reconfiguration actuator applies a force on said slider that move said distal end of said slider away from one of said reconfiguration notches for enabling said handle to be rotated relative to said housing, and wherein when said handle reconfiguration actuator is in the first position said underside of said handle reconfiguration actuator removes the force on said slider so that said distal end of said slider may be seated within one of said reconfiguration notches for locking the position of said handle relative to said housing.

9. The applicator instrument as claimed in claim 8, further comprising a slider return spring in contact with said slider that normally urges said distal end of said slider to be seated within one of said reconfiguration notches, wherein said slider return spring is compressed by the force applied by said underside of said handle reconfiguration actuator when said handle reconfiguration actuator is in the second position.

10. The applicator instrument as claimed in claim 1, wherein said gear train comprises a drive gear having a major face, a raised ring on said major face, and a ring opening formed in said raised ring to define a non-continuous portion of said raised ring and a closed portion of said raised ring.

11. The applicator instrument as claimed in claim 10, wherein said handle reconfiguration actuator further comprises a locking projection that extends from an underside of said handle reconfiguration actuator.

12. The applicator instrument as claimed in claim 11, wherein when said handle reconfiguration actuator is in the second position for rotating said handle relative to said housing, said locking projection of said handle reconfiguration actuator extends into said ring opening of said raised ring on said drive gear for blocking rotation of said drive gear, which, in turn, prevents further squeezing of said trigger toward said handle.

13. The applicator instrument as claimed in claim 11, wherein when said trigger is squeezed for commencing a firing cycle, said closed portion of said raised ring on said drive gear blocks said handle reconfiguration actuator from being moved into the second position so that said handle may not be rotated relative to said housing after commencement of the firing cycle.

14. The applicator instrument as claimed in claim 1, further comprising:
  a cartridge containing a plurality of stacked surgical fasteners inserted into said housing for providing surgical fasteners adapted to be dispensed from a distal end of said elongated shaft; and
  an articulating lever provided on said housing and coupled with said elongated shaft for moving said distal end of said elongated shaft between a straight configuration and an articulated configuration.

15. An applicator instrument having a reconfigurable handle for dispensing surgical fasteners comprising:
  a housing having a proximal end and a distal end;
  an elongated shaft extending from said distal end of said housing;
  a handle coupled with said proximal end of said housing;
  a trigger coupled with said handle;
  a firing system disposed within said housing, said firing system including an energy storing assembly;
  a gear train disposed within said handle and coupled with said trigger, wherein said trigger is squeezable for storing energy in said energy storing assembly;
  said proximal end of said housing having a concave surface and a series of spaced reconfiguration notches that are utilized for positioning said handle relative to said proximal end of said housing;
  a distal end of said handle having a convex surface that matches the curve of said concave surface for guiding rotation of said handle relative to said proximal end of said housing;
  a handle reconfiguration actuator provided on said handle, said handle reconfiguration actuator having a first position for locking said handle in place in one of said reconfiguration notches while enabling said trigger to be squeezed toward said handle for commencing a firing cycle of said firing system and a second position for enabling said handle to rotate to the different angles relative to said housing while preventing said trigger from being squeezed toward said handle for blocking commencement of a firing cycle of said firing system.

16. The applicator instrument as claimed in claim 15, wherein when said handle reconfiguration actuator is in the second position said handle is rotatable between a pistol configuration and an in-line configuration.

17. The applicator instrument as claimed in claim 15, further comprising:
said gear train including a drive gear having a major face, a raised ring on said major face, and a ring opening formed in said raised ring to define a non-continuous portion of said raised ring and a closed portion of said raised ring;
said handle reconfiguration actuator including a locking projection that extends from an underside of said handle reconfiguration actuator, wherein when said handle reconfiguration actuator is in the second position for rotating said handle relative to said housing, said locking projection of said handle reconfiguration actuator extends into said ring opening of said raised ring on said drive gear for blocking rotation of said drive gear, which, in turn, prevents further squeezing of said trigger toward said handle, and wherein when said trigger is squeezed for commencing the firing cycle, said closed portion of said raised ring on said drive gear blocks said handle reconfiguration actuator from being moved into the second position so that said handle may not be rotated relative to said housing after the commencement of the firing cycle.

18. An applicator instrument having a reconfigurable handle for dispensing surgical fasteners comprising:
a housing;
an elongated shaft extending from a distal end of said housing;
a handle coupled with a proximal end of said housing;
a trigger coupled with said handle;
a firing system disposed within said housing, said firing system including an energy storing assembly;
a gear train disposed within said handle and coupled with said trigger, wherein said trigger is squeezable for storing energy in said energy storing assembly;
a handle reconfiguration actuator having a first position for locking said handle in place relative to said housing and a second position for enabling said handle to rotate relative to said housing between a pistol configuration and an in-line configuration,
wherein when said handle reconfiguration actuator is in the first position, said gear train in said handle is coupled with said firing system in said housing, and wherein when said handle reconfiguration actuator is in the second position, said gear train in said handle is decoupled from said firing system in said housing for enabling said handle to rotate relative to said housing.

19. An applicator instrument having a reconfigurable handle for dispensing surgical fasteners comprising:
a housing;
an elongated shaft extending from a distal end of said housing;
a handle coupled with a proximal end of said housing;
a trigger coupled with said handle;
a firing system disposed within said housing, said firing system including an energy storing assembly;
a gear train disposed within said handle and coupled with said trigger, wherein said trigger is squeezable for storing energy in said energy storing assembly;
a handle reconfiguration actuator having a first position for locking said handle in place relative to said housing and a second position for enabling said handle to rotate relative to said housing between a pistol configuration and an in-line configuration,
wherein said gear train comprises a drive gear having a major face, a raised ring on said major face, and a ring opening formed in said raised ring to define a non-continuous portion of said raised ring and a closed portion of said raised ring.

* * * * *